(12) United States Patent
Cox et al.

(10) Patent No.: US 8,002,771 B2
(45) Date of Patent: Aug. 23, 2011

(54) SURGICAL SYSTEM AND PROCEDURE FOR TREATMENT OF MEDICALLY REFRACTORY ATRIAL FIBRILLATION

(75) Inventors: James L. Cox, St. Louis, MO (US); Stephen W. Boyd, San Mateo, CA (US); Hanson S. Gifford, Woodside, CA (US); Matthias Vaska, Palo Alto, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1076 days.

(21) Appl. No.: 11/785,392

(22) Filed: Apr. 17, 2007

(65) Prior Publication Data

US 2007/0191714 A1 Aug. 16, 2007

Related U.S. Application Data

(63) Continuation of application No. 10/171,411, filed on Jun. 12, 2002, now Pat. No. 7,387,126, which is a continuation of application No. 09/606,742, filed on Jun. 29, 2000, now abandoned, which is a continuation of application No. 08/943,683, filed on Oct. 15, 1997, now Pat. No. 6,161,543.

(51) Int. Cl.
*A61B 18/18* (2006.01)
(52) U.S. Cl. .......... 606/51; 606/21; 606/52; 606/45
(58) Field of Classification Search ............ 606/45–52
See application file for complete search history.

(56) References Cited

U.S. PATENT DOCUMENTS

| 984,756 A | 2/1911 | Frisch |
| 3,369,550 A | 2/1968 | Armao et al. |
| 3,862,627 A | 1/1975 | Hans, Sr. |
| 4,022,215 A | 5/1977 | Benson |
| 4,072,152 A | 2/1978 | Linehan |
| 4,207,874 A | 6/1980 | Choy |
| 4,353,371 A * | 10/1982 | Cosman ................. 606/42 |
| 4,375,818 A | 3/1983 | Suwaki et al. |
| 4,655,216 A | 4/1987 | Tischer |

(Continued)

FOREIGN PATENT DOCUMENTS

AU  A-70522/96  11/1994

(Continued)

OTHER PUBLICATIONS

AFx, inc., "FLEX Surgical Ablation Device: Instructions for Use," Document No. 900044 Rev A; Mar. 28, 2000: 1-9.

(Continued)

*Primary Examiner* — Linda Dvorak
*Assistant Examiner* — Amanda Scott
(74) *Attorney, Agent, or Firm* — Wiley Rein LLP

(57) ABSTRACT

The invention provides surgical systems and methods for ablating heart tissue within the interior and/or exterior of the heart. A plurality of probes is provided with each probe configured for introduction into the chest for engaging the heart. Each probe includes an elongated shaft having an elongated ablating surface of a predetermined shape. The elongated shaft and the elongated ablating surface of each probe are configured to ablate a portion of the heart. A sealing device affixed to the heart tissue forms a hemostatic seal between the probe and the penetration in the heart to inhibit blood loss therethrough.

31 Claims, 36 Drawing Sheets

U.S. PATENT DOCUMENTS

| | | | |
|---|---|---|---|
| 4,736,749 A | 4/1988 | Lundback | |
| 4,786,155 A | 11/1988 | Fantone et al. | |
| 4,802,475 A | 2/1989 | Weshahy | |
| 4,815,470 A | 3/1989 | Curtis et al. | |
| 4,872,346 A | 10/1989 | Kelly-Fry et al. | |
| 4,889,137 A | 12/1989 | Kolobow | |
| 4,917,095 A | 4/1990 | Fry et al. | |
| 4,936,281 A | 6/1990 | Stasz | |
| 4,985,030 A | 1/1991 | Melzer et al. | |
| 5,013,312 A | 5/1991 | Parins et al. | |
| 5,080,102 A | 1/1992 | Dory | |
| 5,108,390 A | 4/1992 | Potocky et al. | |
| 5,109,830 A | 5/1992 | Cho | |
| 5,147,355 A | 9/1992 | Friedman et al. | |
| 5,190,541 A | 3/1993 | Abele et al. | |
| 5,197,964 A | 3/1993 | Parins | |
| 5,222,501 A | 6/1993 | Ideker et al. | |
| 5,224,943 A | 7/1993 | Goddard | |
| 5,231,995 A | 8/1993 | Desai | |
| 5,254,116 A | 10/1993 | Baust et al. | |
| 5,263,493 A | 11/1993 | Avitall | |
| 5,269,291 A | 12/1993 | Carter | |
| 5,277,201 A | 1/1994 | Stern | |
| 5,281,215 A | 1/1994 | Milder | |
| 5,290,286 A * | 3/1994 | Parins | 606/50 |
| 5,295,484 A | 3/1994 | Marcus et al. | |
| 5,323,781 A | 6/1994 | Ideker et al. | |
| 5,324,255 A | 6/1994 | Passafaro et al. | |
| 5,324,284 A | 6/1994 | Imran | |
| 5,334,181 A | 8/1994 | Rubinsky et al. | |
| 5,341,807 A | 8/1994 | Nardella | |
| 5,348,554 A | 9/1994 | Imran et al. | |
| 5,353,783 A | 10/1994 | Nakao et al. | |
| 5,354,258 A | 10/1994 | Dory | |
| 5,366,443 A | 11/1994 | Eggers et al. | |
| 5,370,675 A | 12/1994 | Edwards et al. | |
| 5,385,148 A | 1/1995 | Lesh et al. | |
| 5,396,887 A | 3/1995 | Imran | |
| 5,400,783 A | 3/1995 | Pomeranz et al. | |
| 5,405,376 A | 4/1995 | Mulier et al. | |
| 5,406,946 A | 4/1995 | Imran | |
| 5,423,807 A | 6/1995 | Milder | |
| 5,423,811 A | 6/1995 | Imran et al. | |
| 5,427,119 A | 6/1995 | Swartz et al. | |
| 5,431,649 A | 7/1995 | Mulier et al. | |
| 5,433,708 A | 7/1995 | Nichols et al. | |
| 5,435,308 A | 7/1995 | Gallup et al. | |
| 5,437,651 A | 8/1995 | Todd et al. | |
| 5,437,664 A | 8/1995 | Cohen et al. | |
| 5,443,463 A | 8/1995 | Stern et al. | |
| 5,443,470 A | 8/1995 | Stern et al. | |
| 5,450,843 A | 9/1995 | Moll et al. | |
| 5,452,733 A | 9/1995 | Sterman et al. | |
| 5,462,521 A | 10/1995 | Brucker et al. | |
| 5,462,545 A | 10/1995 | Wang et al. | |
| 5,465,717 A | 11/1995 | Imran et al. | |
| 5,469,853 A | 11/1995 | Law et al. | |
| 5,478,330 A | 12/1995 | Imran et al. | |
| 5,487,385 A | 1/1996 | Avitall | |
| 5,487,757 A | 1/1996 | Truckai et al. | |
| 5,496,312 A | 3/1996 | Klicek | |
| 5,497,774 A | 3/1996 | Swartz et al. | |
| 5,500,012 A | 3/1996 | Brucker et al. | |
| 5,501,698 A | 3/1996 | Roth et al. | |
| 5,505,730 A | 4/1996 | Edwards | |
| 5,520,682 A | 5/1996 | Baust et al. | |
| 5,536,251 A * | 7/1996 | Evard et al. | 604/93.01 |
| 5,536,267 A | 7/1996 | Edwards et al. | |
| 5,540,679 A | 7/1996 | Fram et al. | |
| 5,540,681 A | 7/1996 | Strul et al. | |
| 5,545,195 A | 8/1996 | Lennox et al. | |
| 5,545,200 A | 8/1996 | West et al. | |
| 5,549,661 A | 8/1996 | Kordis et al. | |
| 5,555,883 A | 9/1996 | Avitall | |
| 5,558,644 A | 9/1996 | Boyd et al. | |
| 5,560,362 A | 10/1996 | Sliwa, Jr. et al. | |
| 5,562,720 A | 10/1996 | Stern et al. | |
| 5,569,241 A | 10/1996 | Edwards | |
| 5,571,088 A | 11/1996 | Lennox et al. | |
| 5,571,215 A | 11/1996 | Sterman et al. | |
| 5,575,766 A | 11/1996 | Swartz et al. | |
| 5,575,788 A | 11/1996 | Baker et al. | |
| 5,575,810 A | 11/1996 | Swanson et al. | |
| 5,578,007 A | 11/1996 | Imran | |
| 5,582,609 A | 12/1996 | Swanson et al. | |
| 5,584,803 A | 12/1996 | Stevens et al. | |
| 5,588,432 A | 12/1996 | Crowley | |
| 5,590,657 A | 1/1997 | Cain et al. | |
| 5,595,183 A | 1/1997 | Swanson et al. | |
| 5,607,462 A | 3/1997 | Imran | |
| 5,617,854 A | 4/1997 | Munsif | |
| 5,626,607 A * | 5/1997 | Malecki et al. | 606/205 |
| 5,630,837 A | 5/1997 | Crowley | |
| 5,637,090 A | 6/1997 | McGee et al. | |
| 5,643,197 A | 7/1997 | Brucker et al. | |
| 5,656,029 A | 8/1997 | Imran et al. | |
| 5,658,278 A | 8/1997 | Imran et al. | |
| 5,671,747 A | 9/1997 | Connor | |
| 5,673,695 A | 10/1997 | McGee et al. | |
| 5,676,662 A | 10/1997 | Fleischhacker et al. | |
| 5,676,692 A | 10/1997 | Sanghvi et al. | |
| 5,676,693 A | 10/1997 | LaFontaine | |
| 5,678,550 A | 10/1997 | Bassen et al. | |
| 5,680,860 A | 10/1997 | Imran | |
| 5,681,278 A | 10/1997 | Igo et al. | |
| 5,681,308 A | 10/1997 | Edwards et al. | |
| 5,687,723 A | 11/1997 | Avitall | |
| 5,687,737 A | 11/1997 | Branham et al. | |
| 5,688,267 A | 11/1997 | Panescu et al. | |
| 5,690,611 A | 11/1997 | Swartz et al. | |
| 5,697,925 A | 12/1997 | Taylor | |
| 5,697,927 A | 12/1997 | Imran et al. | |
| 5,697,928 A | 12/1997 | Walcott et al. | |
| 5,697,949 A | 12/1997 | Giurtino et al. | |
| 5,713,942 A | 2/1998 | Stern | |
| 5,716,389 A | 2/1998 | Walinsky et al. | |
| 5,718,241 A | 2/1998 | Ben-Haim et al. | |
| 5,718,701 A | 2/1998 | Shai et al. | |
| 5,720,775 A | 2/1998 | Lanard | |
| 5,722,402 A | 3/1998 | Swanson et al. | |
| 5,728,094 A | 3/1998 | Edwards et al. | |
| 5,730,074 A | 3/1998 | Peter | |
| 5,730,127 A | 3/1998 | Avitall | |
| 5,730,704 A | 3/1998 | Avitall | |
| 5,733,280 A | 3/1998 | Avitall | |
| 5,735,280 A | 4/1998 | Sherman et al. | |
| 5,735,290 A | 4/1998 | Sterman et al. | |
| 5,746,224 A | 5/1998 | Edwards | |
| 5,755,760 A | 5/1998 | Maguire et al. | |
| 5,782,828 A | 7/1998 | Chen et al. | |
| 5,782,899 A | 7/1998 | Imran | |
| 5,785,706 A | 7/1998 | Bednarek | |
| 5,788,636 A | 8/1998 | Curley | |
| 5,797,960 A | 8/1998 | Stevens et al. | |
| 5,800,428 A | 9/1998 | Nelson et al. | |
| 5,800,482 A | 9/1998 | Pomeranz et al. | |
| 5,810,721 A | 9/1998 | Mueller et al. | |
| 5,810,802 A | 9/1998 | Panescu et al. | |
| 5,817,021 A | 10/1998 | Reichenberger | |
| 5,827,216 A | 10/1998 | Igo et al. | |
| 5,827,281 A | 10/1998 | Levin | |
| 5,830,214 A | 11/1998 | Flom et al. | |
| 5,836,947 A | 11/1998 | Fleischman et al. | |
| 5,840,030 A | 11/1998 | Ferek-Petric et al. | |
| 5,844,349 A | 12/1998 | Oakley et al. | |
| 5,849,028 A | 12/1998 | Chen | |
| 5,863,291 A | 1/1999 | Schaer | |
| 5,871,523 A | 2/1999 | Fleischman et al. | |
| 5,871,525 A | 2/1999 | Edwards et al. | |
| 5,873,845 A | 2/1999 | Cline et al. | |
| 5,876,399 A | 3/1999 | Chia et al. | |
| 5,879,295 A | 3/1999 | Li et al. | |
| 5,879,296 A | 3/1999 | Ockuly et al. | |
| 5,882,346 A | 3/1999 | Pomeranz et al. | |
| 5,885,278 A | 3/1999 | Fleischman | |
| 5,891,134 A | 4/1999 | Goble et al. | |
| 5,893,848 A | 4/1999 | Negus et al. | |

| | | |
|---|---|---|
| 5,895,417 A | 4/1999 | Pomeranz et al. |
| 5,897,554 A | 4/1999 | Chia et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,927,284 A | 7/1999 | Borst et al. |
| 5,928,191 A | 7/1999 | Houser et al. |
| 5,931,810 A | 8/1999 | Grabek |
| 5,931,848 A | 8/1999 | Saadat |
| 5,954,661 A | 9/1999 | Greenspon et al. |
| 5,971,980 A | 10/1999 | Sherman |
| 5,971,983 A | 10/1999 | Lesh |
| 5,993,447 A | 11/1999 | Blewett et al. |
| 6,007,499 A | 12/1999 | Martin et al. |
| 6,012,457 A | 1/2000 | Lesh |
| 6,016,811 A | 1/2000 | Knopp et al. |
| 6,023,638 A | 2/2000 | Swanson |
| 6,042,556 A | 3/2000 | Beach et al. |
| 6,068,629 A | 5/2000 | Haissaguerre et al. |
| 6,071,274 A | 6/2000 | Thompson et al. |
| 6,071,279 A | 6/2000 | Whayne et al. |
| 6,071,282 A | 6/2000 | Fleischman |
| 6,088,894 A | 7/2000 | Oakley |
| 6,096,037 A * | 8/2000 | Mulier et al. .................. 606/49 |
| 6,113,592 A | 9/2000 | Taylor |
| 6,117,101 A | 9/2000 | Diederich et al. |
| 6,120,496 A | 9/2000 | Whayne et al. |
| 6,139,563 A * | 10/2000 | Cosgrove et al. ............. 606/205 |
| 6,142,993 A | 11/2000 | Whayne et al. |
| 6,142,994 A | 11/2000 | Swanson et al. |
| 6,146,379 A | 11/2000 | Fleischman et al. |
| 6,152,920 A | 11/2000 | Thompson et al. |
| 6,161,543 A | 12/2000 | Cox et al. |
| 6,164,283 A | 12/2000 | Lesh |
| 6,206,831 B1 | 3/2001 | Suorsa et al. |
| 6,212,426 B1 | 4/2001 | Swanson |
| 6,214,754 B1 | 4/2001 | Stein |
| 6,217,528 B1 | 4/2001 | Koblish et al. |
| 6,217,576 B1 | 4/2001 | Tu et al. |
| 6,231,518 B1 | 5/2001 | Grabek et al. |
| 6,235,024 B1 | 5/2001 | Tu |
| 6,237,605 B1 | 5/2001 | Vaska et al. |
| 6,238,347 B1 | 5/2001 | Nix et al. |
| 6,241,722 B1 | 6/2001 | Dobak et al. |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,128 B1 | 6/2001 | Knopp et al. |
| 6,270,471 B1 | 8/2001 | Hechel et al. |
| 6,293,943 B1 | 9/2001 | Panescu et al. |
| 6,296,619 B1 | 10/2001 | Brisken et al. |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,325,797 B1 | 12/2001 | Stewart et al. |
| 6,325,798 B1 | 12/2001 | Edwards et al. |
| 6,332,881 B1 | 12/2001 | Carner et al. |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,720 B1 | 6/2002 | Hissong et al. |
| 6,413,254 B1 | 7/2002 | Hissong et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,447,507 B1 | 9/2002 | Bednarek et al. |
| 6,454,758 B1 | 9/2002 | Thompson et al. |
| 6,461,314 B1 | 10/2002 | Pant et al. |
| 6,461,356 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,477,396 B1 | 11/2002 | Mest et al. |
| 6,484,727 B1 | 11/2002 | Vaska et al. |
| 6,514,249 B1 | 2/2003 | Maguire et al. |
| 6,517,536 B2 | 2/2003 | Hooven et al. |
| 6,527,767 B2 | 3/2003 | Wang et al. |
| 6,544,262 B2 | 4/2003 | Fleischman |
| 6,546,934 B1 | 4/2003 | Ingle et al. |
| 6,582,423 B1 | 6/2003 | Thapliyal et al. |
| 6,605,084 B2 | 8/2003 | Acker et al. |
| 6,610,055 B1 | 8/2003 | Swanson et al. |
| 6,645,199 B1 | 11/2003 | Jenkins et al. |
| 6,645,202 B1 | 11/2003 | Pless et al. |
| 6,689,128 B2 | 2/2004 | Sliwa, Jr. et al. |
| 6,692,450 B1 | 2/2004 | Coleman |
| 6,701,931 B2 | 3/2004 | Sliwa, Jr. et al. |
| 6,740,080 B2 | 5/2004 | Jain et al. |
| 6,745,080 B2 | 6/2004 | Koblish |
| 6,771,996 B2 | 8/2004 | Bowe et al. |
| 6,805,128 B1 | 10/2004 | Pless et al. |
| 6,805,129 B1 | 10/2004 | Pless et al. |
| 6,840,936 B2 | 1/2005 | Sliwa et al. |
| 6,858,026 B2 | 2/2005 | Sliwa et al. |
| 6,942,661 B2 | 9/2005 | Swanson |
| 6,942,662 B2 | 9/2005 | Goble et al. |
| 7,052,493 B2 | 5/2006 | Vaska et al. |
| 7,213,601 B2 | 5/2007 | Stevens et al. |
| 7,338,486 B2 | 3/2008 | Sliwa et al. |
| 7,387,126 B2 | 6/2008 | Cox et al. |
| 7,674,257 B2 | 3/2010 | Pless et al. |
| 2002/0019627 A1 | 2/2002 | Maguire et al. |
| 2002/0022839 A1 | 2/2002 | Stewart et al. |
| 2002/0026183 A1 | 2/2002 | Simpson |
| 2002/0042610 A1 | 4/2002 | Sliwa et al. |
| 2002/0062124 A1 | 5/2002 | Keane |
| 2002/0087151 A1 | 7/2002 | Mody et al. |
| 2002/0087208 A1 | 7/2002 | Koblish et al. |
| 2002/0111567 A1 | 8/2002 | Vanden Hoek et al. |
| 2002/0128639 A1 | 9/2002 | Pless et al. |
| 2002/0143326 A1 | 10/2002 | Foley et al. |
| 2003/0078571 A1 | 4/2003 | Sliwa, Jr. et al. |
| 2004/0106918 A1 | 6/2004 | Cox et al. |
| 2004/0260278 A1 | 12/2004 | Anderson et al. |
| 2005/0033274 A1 | 2/2005 | Pless et al. |
| 2005/0245918 A1 | 11/2005 | Sliwa, Jr. et al. |
| 2005/0251125 A1 | 11/2005 | Pless et al. |
| 2006/0135954 A1 | 6/2006 | Sliwa, Jr. et al. |
| 2006/0184167 A1 | 8/2006 | Vaska et al. |
| 2006/0200119 A1 | 9/2006 | Vaska et al. |
| 2007/0066974 A1 | 3/2007 | Vaska et al. |
| 2007/0255276 A1 | 11/2007 | Sliwa et al. |
| 2007/0282324 A1 | 12/2007 | Vaska et al. |
| 2007/0293855 A1 | 12/2007 | Sliwa et al. |
| 2007/0299496 A1 | 12/2007 | Podmore et al. |
| 2008/0045946 A1 | 2/2008 | Vaska |
| 2009/0192603 A1 | 7/2009 | Ryan |

FOREIGN PATENT DOCUMENTS

| | | |
|---|---|---|
| EP | 1181896 A1 | 2/2002 |
| GB | 2 094 636 | 9/1982 |
| GB | 2 289 510 A | 11/1995 |
| WO | WO 95/10318 | 4/1995 |
| WO | WO 95/10319 | 4/1995 |
| WO | WO 95/10321 | 4/1995 |
| WO | WO 95/10978 | 4/1995 |
| WO | WO 95/15115 | 6/1995 |
| WO | WO 95/17222 | 6/1995 |
| WO | WO 95/30380 A | 11/1995 |
| WO | WO 96/10961 | 4/1996 |
| WO | WO 96/26675 | 9/1996 |
| WO | WO 96/39966 | 12/1996 |
| WO | WO 97/06727 | 2/1997 |
| WO | WO 97/17904 | 5/1997 |
| WO | WO 97/18853 | 5/1997 |
| WO | WO 97/25916 | 7/1997 |

| | | |
|---|---|---|
| WO | WO 97/25918 | 7/1997 |
| WO | WO 97/25919 | 7/1997 |
| WO | WO-97/29699 | 8/1997 |
| WO | WO 97/32525 | 9/1997 |
| WO | WO 97/33526 | 9/1997 |
| WO | WO 97/37607 | 10/1997 |
| WO | WO-97/38748 | 10/1997 |
| WO | WO 97/41793 | 11/1997 |
| WO | WO 97/43970 | 11/1997 |
| WO | WO 97/45156 | 12/1997 |
| WO | WO 98/17187 | 4/1998 |
| WO | WO 98/24488 | 6/1998 |
| WO | WO 98/26724 | 6/1998 |
| WO | WO 98/37822 | 9/1998 |
| WO | WO 98/48881 | 11/1998 |
| WO | WO 98/49957 | 11/1998 |
| WO | WO 99/02096 | 1/1999 |
| WO | WO-99/02096 | 1/1999 |
| WO | WO 99/04696 | 2/1999 |
| WO | WO 99/48421 A1 | 9/1999 |
| WO | WO 99/49788 | 10/1999 |
| WO | WO 99/56812 | 11/1999 |
| WO | WO 99/59486 | 11/1999 |
| WO | WO 00/45706 | 8/2000 |
| WO | WO 00/57495 | 9/2000 |
| WO | WO 01/03594 A1 | 1/2001 |
| WO | WO 01/05305 A1 | 1/2001 |
| WO | WO-01/05306 | 1/2001 |
| WO | WO 01/28623 A2 | 4/2001 |
| WO | WO 01/45550 A2 | 6/2001 |
| WO | WO 01/66189 A1 | 9/2001 |
| WO | WO 01/70112 A1 | 9/2001 |
| WO | WO 01/72234 A1 | 10/2001 |
| WO | WO 01/72373 A2 | 10/2001 |
| WO | WO-01/80708 | 11/2001 |
| WO | WO 01/82778 A2 | 11/2001 |
| WO | WO 02/05720 A1 | 1/2002 |
| WO | WO 02/05722 A1 | 1/2002 |
| WO | WO 02/05868 A2 | 1/2002 |
| WO | WO 02/30310 A1 | 1/2002 |
| WO | WO 02/09610 A1 | 2/2002 |
| WO | WO 02/21995 A2 | 3/2002 |
| WO | WO 02/24050 | 3/2002 |
| WO | WO 02/26142 A1 | 4/2002 |
| WO | WO 02/40093 | 5/2002 |
| WO | WO 02/45608 A2 | 6/2002 |
| WO | WO 02/077774 A2 | 10/2002 |
| WO | WO-02/102231 | 12/2002 |

OTHER PUBLICATIONS

AFx, inc., "AFx Microwave Generator, Series 1000; User's Manual," Document No. 900067/A/1310, (2000): 1-13.
AFx, inc., "FLEX10™: Accessory for the Afx Microwave Ablation Aystem; Instructions for Use," Document No. 900077/C/1638, (2001): 1-8. Supplemental Document No. 900106/A/1586.
AFx, inc., "LYNX Surgical Ablation Device: Instructions for Use," Document No. 900024/K/1114: 1-4.
Boston Scientific, EP Technologies, "Cobra® Electrosurgical Unit, Operator's Manual: 4810 & 4811," Document No. 11292-001 EAW Ver AC, Feb. 2000; pp. 1-1 thru 9-2.
Boston Scientific, EP Technologies, "Cobra® Surgical Probe; Directions for Use," Document No. 13954-001 Rev A, Oct. 2001: p. 3.
Boston Scientific, EP Technologies, "Cobra® RF System: The first surgical system for creating linear lesions." Document No. DEP-225 Rev A, Jan. 2002.
Caccitolo et al., "Open-Heart Endocardial Radiofrequency Ablation: . . . " *J of Surgical Research*, (2001); 97: 27-33.
Chevalier, et al., "Thoracoscopic Epicardial Radiofrequency Ablation for Vagal Atrial Fibrillation in Dogs," *PACE* Jun. 1999; 22 (Part l), 880-886.
Cox et al., "The Surgical Treatment of Atrial Fibrillation, IV Surgical Technique, " *J Thorac Cardiovasc Surg*, 1991; 101: 584-592.
Cox et al., "The Maze III Procedure for Treatment of Atrial Fibrillation," *Cardiac Arrhythmias*, 78: 460-475.
Demazumder et al., "Comparison of Irrigated Electrode Designs for Radiofrequency Ablation of Myocardium," *J of Interventional Cardiac Electrophvsiology5*, (2001): 391-400.

Elvan et al., "Radiofrequency Catheter Ablation of the Atria Eliminates Pacing-Induced Sustained Atrial Fibrillation and Reduces Connexin in 43 Dogs," *Circulation*, 1997;96(5):1675-1685.
Fieguth et al., "Inhibition of Atrial Fibrillation by Pulmonary Vein Isolation and Auricular Resection—Experimental Study in a Sheep Model," *European Journal of Cardio-Thoracic Surgery*, 1997;11:714-721.
He et al., "Preliminary Results Using Ultrasound Energy for Ablation of the Ventricular Myocardium in Dogs," *Am J Card*, 1994;73:1029-1031.
He et al., "Application of Ultrasound Energy for Intracardiac Ablation of Arrhythmias," *The European Society of Cardiology*, 1995;16:961-966.
Hunt, John W., "Application of Microwave, Ultrasound and Radiofrequency Heating," *Natl Cancer Inst Monogr*, (1982); 61: 447-456.
Hynynen et al., "Cylindrical Ultrasonic Transducers for Cardiac Catheter Ablation," *IEEE Transactions on Biomedical Engineering*, 1997;44(2):144-151.
Inoue et al., "Video Assisted Thoracoscopic and Cardioscopic Radiofrequency Maze Ablation," *ASAIO Journal*, 1997;43:334-337.
Jumrussirikul et al., "Prospective Comparison of Temperature Guided Microwave and Radiofrequency Catheter Ablation in the Swine Heart," *PACE* (1998); 21: 1364-1374.
Lee, et al., "High Intensity Focused Ultrasound Effect on Cardiac Tissues: Potential for Clinical Application," *Echocardiography*, (2000) vol. 17, No. 6, Part 1: 563-566.
Liem et al. "Microwave Catheter Ablation Using a Clinical Prototype System with a Lateral Firing Antenna Design," *PACE*, (1998); 21 [pt 1]: 714-721.
McRury, Ian D., Haines, David E., "Ablation for the Treatment of Arrhythmais," *Proceedings of the IEEE*, (1996); vol. 84, No. 3: 404-415.
Mitchell et al., "Morphological and Physiological Characterictics of Discontinuous Linear Atrial Ablations During Atrial Pacing and Atrial Fibrillation," *J Cardiovas Electrophysiol*, (1999); vol. 10: 378-386.
Mittleman et al., "Use of the Saline Electrode Catheter for Improved Energy Delivery and Increased Lesion Size in Radiofrequency Catherter Ablation," *PACE*, (1995); 18[Pt 1]: 1022-1027.
Ohkubo et al., "Experimental Study of Catheter Ablation Using Ultrasound Energy in Canine and Porcine Hearts," *Jpn Heart J*, (1998); 39: 399-409.
Olgin et al., "Electrophysical Effects of Long. Linear Atrial Lesions Placed Under Intracardiac Ultrasound Guidance," *Circulation*, 1997;96(8):2715-2721.
Petersen et al., "Tissue Temperatures and Lesion Size During Irrigated Tip Catheter Radiofrequency Ablation: . . . ," *PACE*, (2000); 23: 8-17.
Pfeiffer et al., "Epicardial Neodymium . . . ," *Am Heart J*, 1996;94(12):3221-3225.
Righetti et al., "Elastographic Characterization of HIFU-Induced Lesions in Canine Livers," *Ultrasound in Med. & Biol.*, (1999), vol. 25 No. 7; 1099-1113.
Sibille et al., "Characterization of Extracorporeal Ablation of Normal and Tumor-Bearing Liver Tissue by High Intensity Focused Ultrasound," *Ultrasound in Med. & Biol.*, (1993); vol. 19, No. 9: 803-813.
Sosa et al., "Radiofrequency Catheter Ablation of Ventricular Tachycardia Guided by Nonsurgical Epicardial Mapping in Chronic Chagasic heart Disease," *PACE*, Jan. 1999; 22 (Part I), 128-130.
Strickberger et al., "Extracardiac Ablation of the Canine Atrioventricular Junction by Use of High-Intensity Focused Ultrasound," *Circulation*, (1999); 100: 203-208.
Stone et al., "Ablation of Atrial Fibrillation by the Maze Procedure," *Surgical Forum, Cardiothoracic Surgery*, date unknown, 213-215.
Thomas et al., "Microwave Ablation of Myocardial Tissue: . . . " *J Cardiovasc Electrophysiol*, (1999); vol. 10: 72-78.
Vanderbrink et al., "Safety and Efficacy of a Steerable Temperature Monitoring Microwave Catheter System for Ventriculat Myocardial Ablation," *J Cardiovasc Electrophysiol*, (2000); vol. 11: 305-310.

Von Oppell et al., "Effectiveness of two radiofrequency ablation systems in atrial tissue," *Euro J of Cardio-thoracic Surg*, (2001); 20: 956-960.

Watanabe et al., "Experimental Application of Microwave Tissue Coagulation to Ventricular Myocardium," *Ann Thorac Surg*, (1999); 67: 666-671.

Weber, "Laser versus Radiofrequency Catheter Ablation of Ventricular Myocardium in Dogs: A Comparative Test," *Cardiology*, 1997: 88:346-352.

Whayne et al., "Microwave Catheter Ablation of Myocardium In Vitro . . . " *Circulation* (1994); 89: 2390-2395.

Williams et al., "Surgical Treatment of Atrial Fibrillation Using Radiofrequency Energy," *Ann Thorac Surg*, (2001); 71: 1939-1944.

Wonnell et al., "Evaluation of Microwave and Radio Frequency Catheter Ablation in a Myocardium-Equivalent Phantom Model," *IEEE Transactions on Biomedical Engineering*, 1992;39(10):1086-1095.

Zimmer et al., "The Feasibility of Using Ultrasound for Cardiac Ablation," *IEEE Transactions on Biomedical Engineering*, 1995;42(9):891-897.

Avitall et al., "A Thoracoscopic Approach to Ablate Atrial Fibrillation Via Linear Radiofrequency Lesion Generation on the Epicardium of Both Atria," PACE, Apr. 1996;19(Part II):626,#241.

Jais et al., "Catheter Ablation for Paroxysmal Atrial Fibrillation: High Success Rates with Ablation in the Left Atrium," Circulation (Nov. 1996) 94:I-675,#3946.

Lee et al., "Minimally Invasive Epicardial Atrial Linear Ablation Using Cooled Radiofrequency Energy," Circulation (Nov. 1997) 96:577,I-576,#3221.

Lindsay et al., "Intraoperative Observations and Epicardial Mapping after Attempted Catheter Ablation of Atrial Fibrillation," Circulation (Nov. 1997) 96:450,#2517.

Nakagawa et al, "Use of Atrial Potential Attenuation to Identify Endpoint of Radiofrequency Application for Continuous, Transmural Linear Atrial Ablation," Circulation (Nov. 1997) 96:577,I-451,#2523.

Sharma et al., "A Comparison of Sequential with Simultaneous Delivery of RF Energy Application at Multiple Electrodes to Produce Linear Continuous Lesions," Circulation (Nov. 1997) 96:576,I-576,#3220.

Sie et al., "Radiofrequency Ablation of Atrial Fibrillation in Patients Undergoing Valve Surgery," Circulation (Nov. 1997) 84:1450,#2519.

Sie et al., "Radiofrequency Ablation of Atrial Fibrillation in Patients Undergoing Mitral Valve Surgery. First Experience," Circulation (Nov. 1996) 96:450,I-675,#3946.

U.S. Appl. No. 11/785,427, filed Apr. 17, 2007, Vaska, et al.

U.S. Appl. No. 11/882,072, filed Jul. 30, 2007, Vaska, et al.

U.S. Appl. No. 11/935,582, filed Nov. 6, 2007, Cox et al.

Cox et al., The Surgical Treatment of Atrial Fibrillation. I. Summary of the Current Concepts of the Mechanisms of Atrial Flutter and Atrial Fibrillation, J. Thorac. Cardiovasc. Surgery, vol. 101, 402-05 (Mar. 1991). Published by the American Association for Thoracic Surgery and The Western Thoracic Surgical Association in Beverly, MA.

Cox et al., The Surgical Treatment of Atrial Fibrillation. II. Intraoperative Electrophysiologic Mapping and Description of the Electrophysiologic Basis of Atrial Flutter and Atrial Fibrillation, J. Thorac. Cardiovasc. Surgery, vol. 101, 406-26 (Mar. 1991). Published by the American Association for Thoracic Surgery and The Western Thoracic Surgical Association in Beverly, MA.

Cox et al., The Surgical Treatment of Atrial Fibrillation. III. Development of a Definitive Surgical Procedure, J. Thorac. Cardiovasc. Surgery, vol. 101, 569-83 (Apr. 1991). Published by the American Association for Thoracic Surgery and The Western Thoracic Surgical Association in Beverly, MA.

* cited by examiner

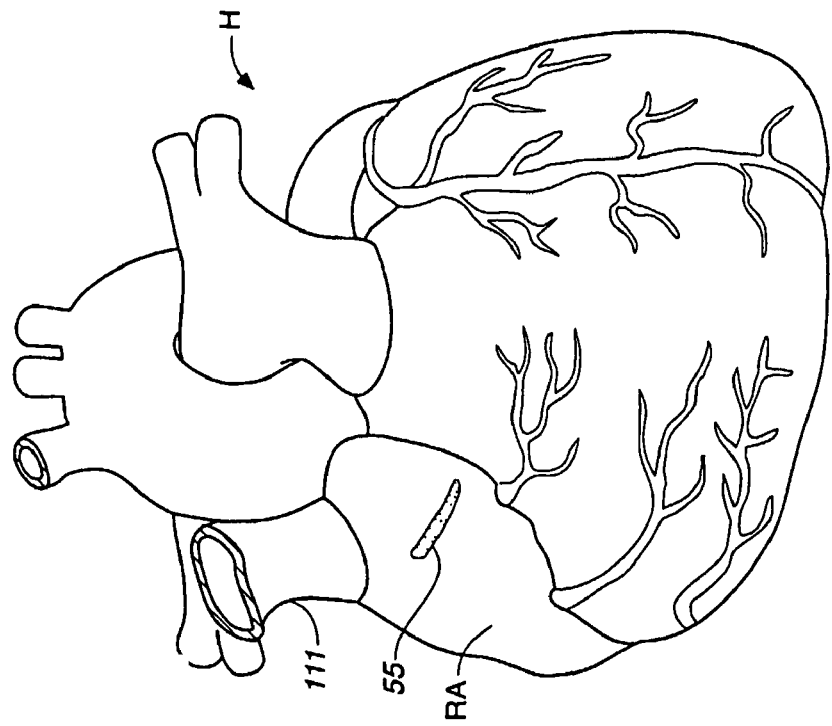
FIG._1
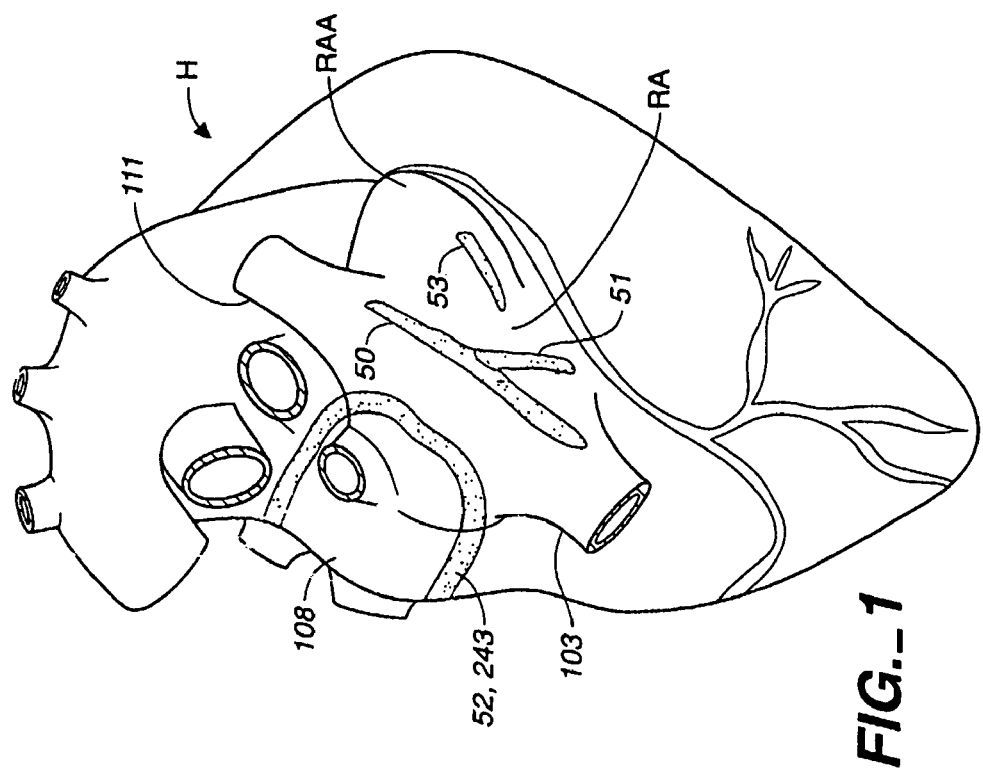
FIG._2

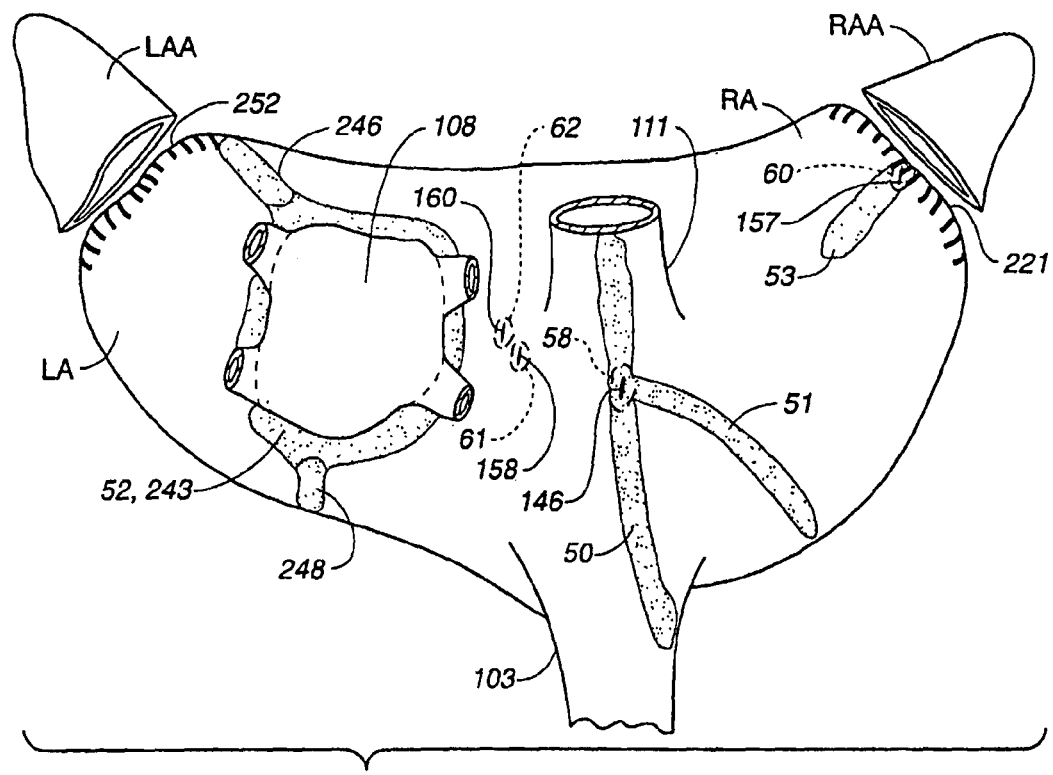
FIG._3A
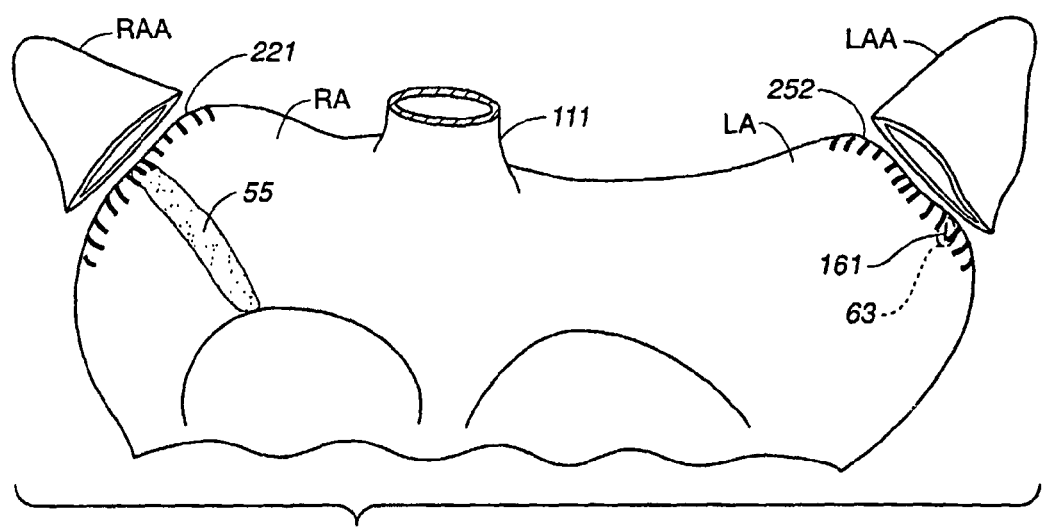
FIG._3B

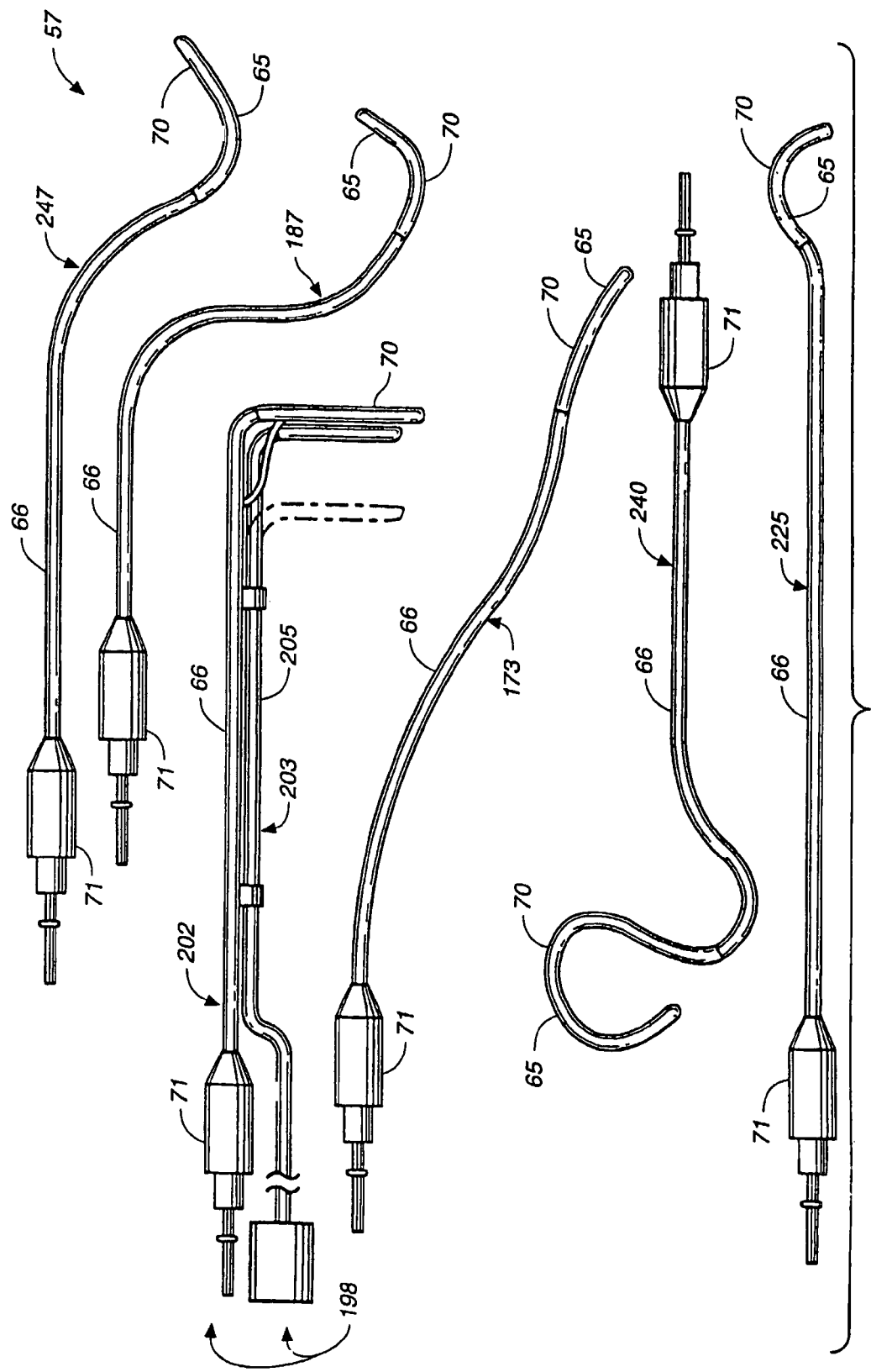
FIG._4

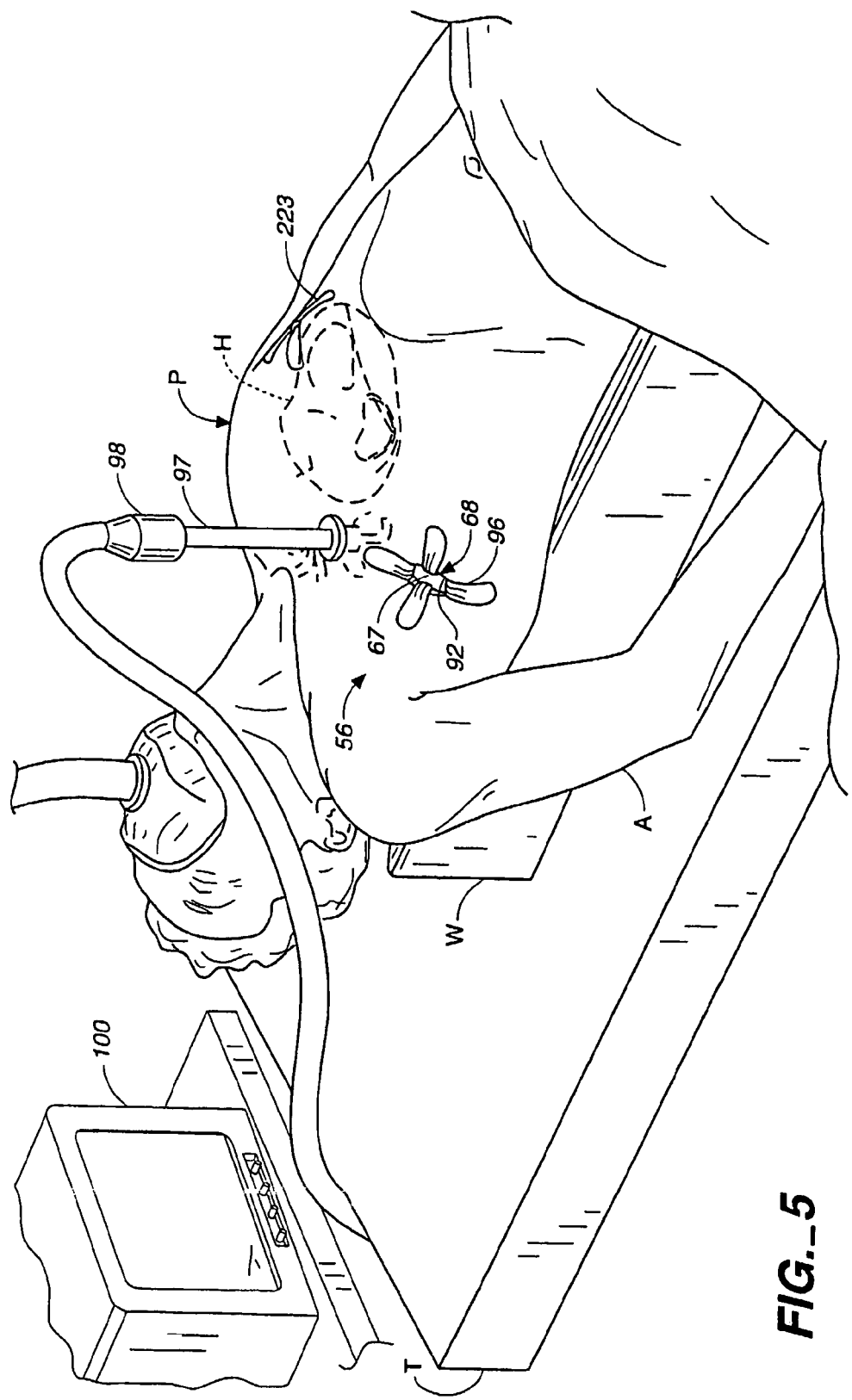
FIG._5

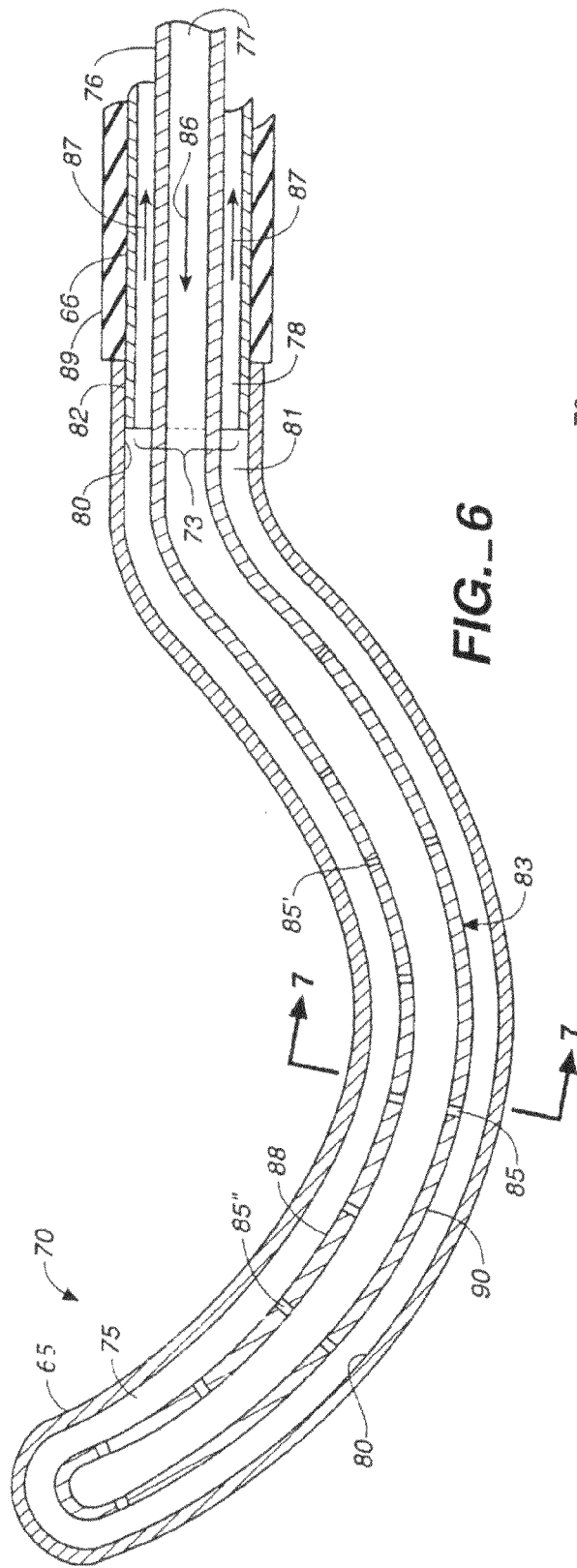
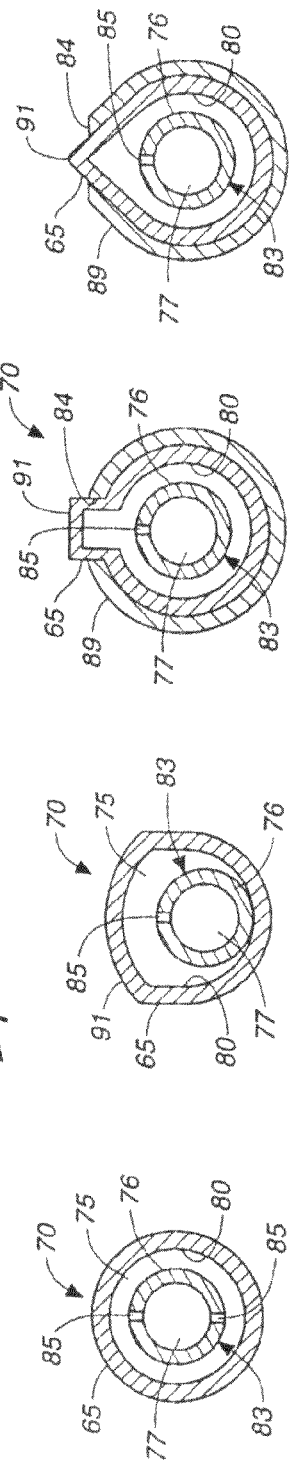

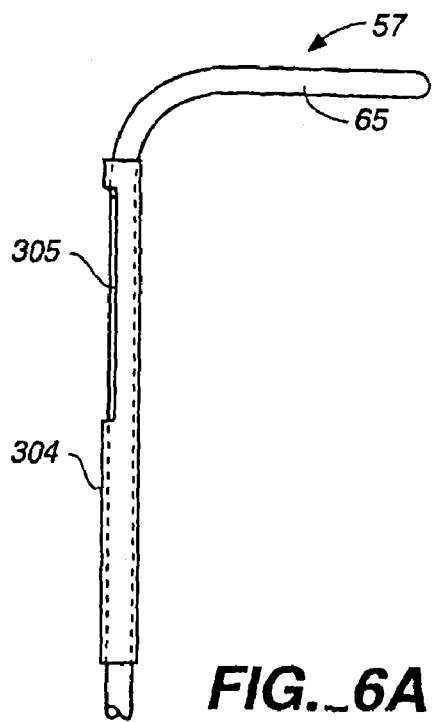
FIG._6A
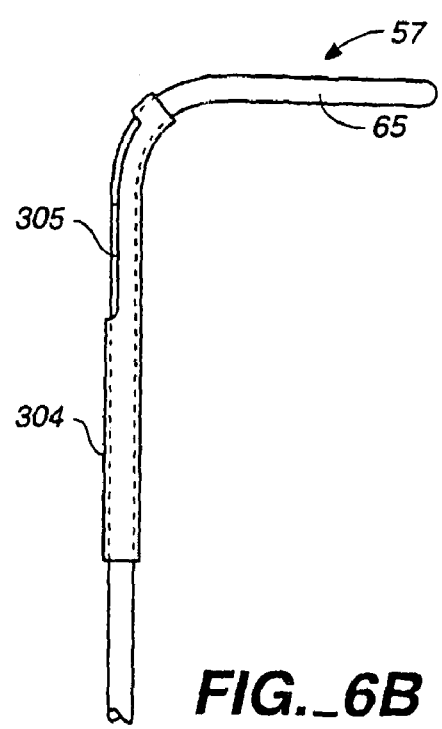
FIG._6B
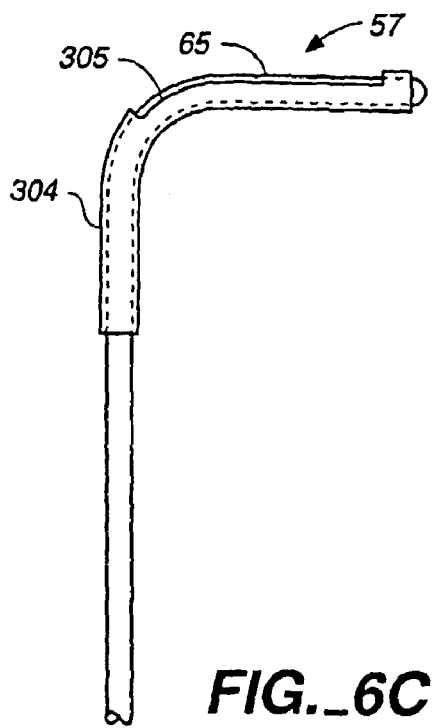
FIG._6C
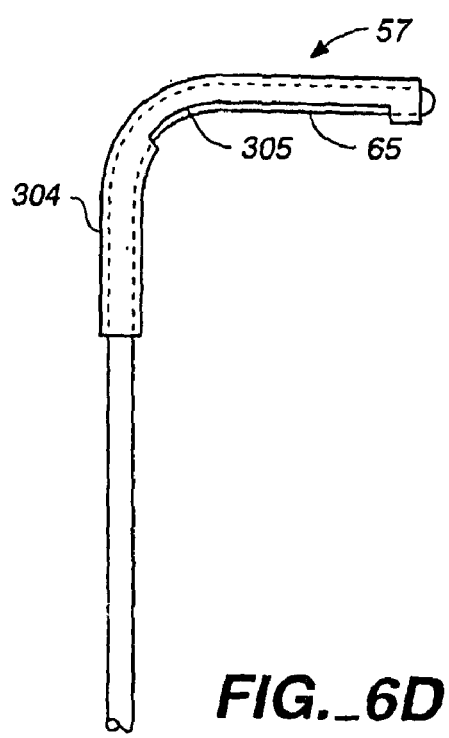
FIG._6D

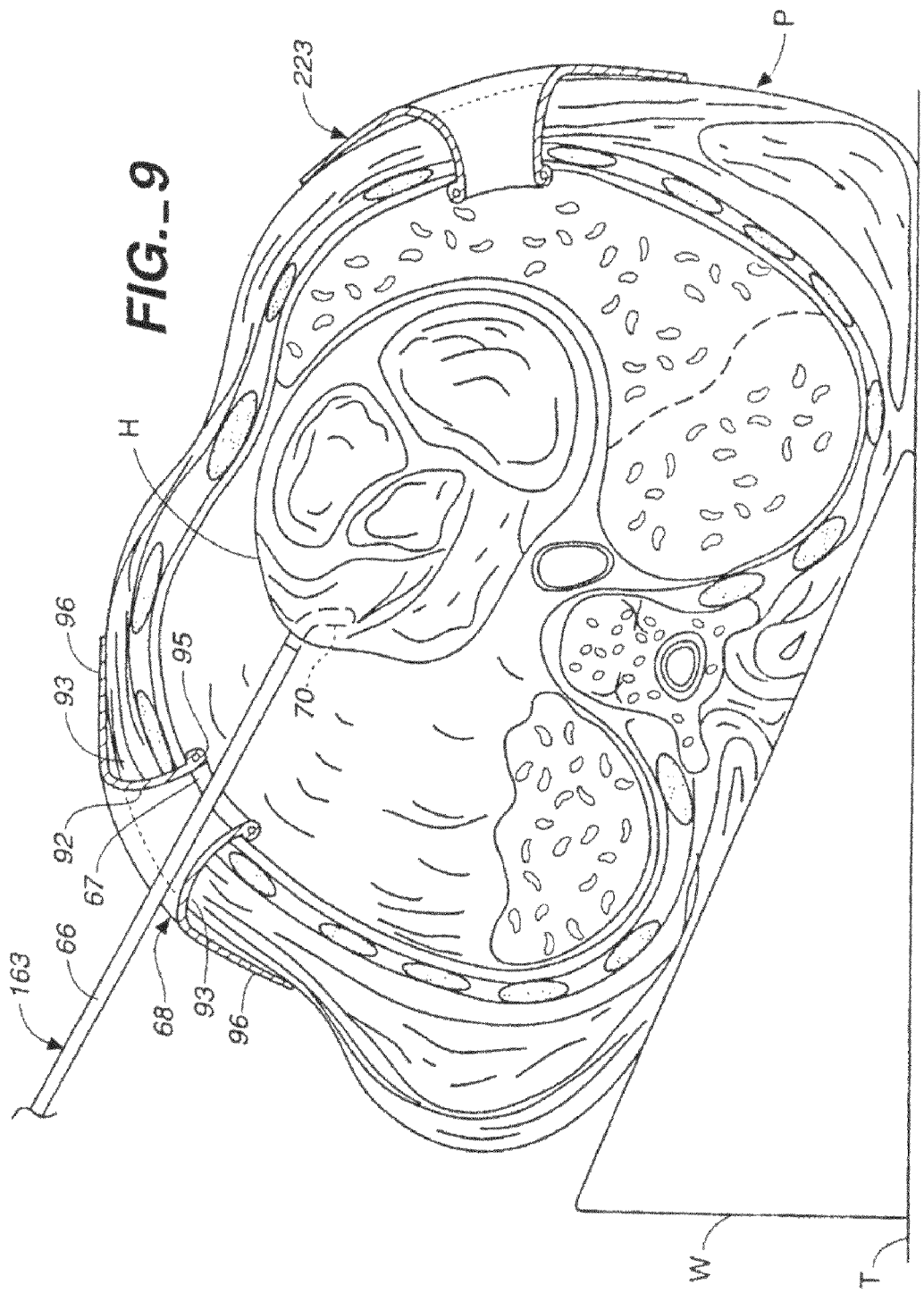

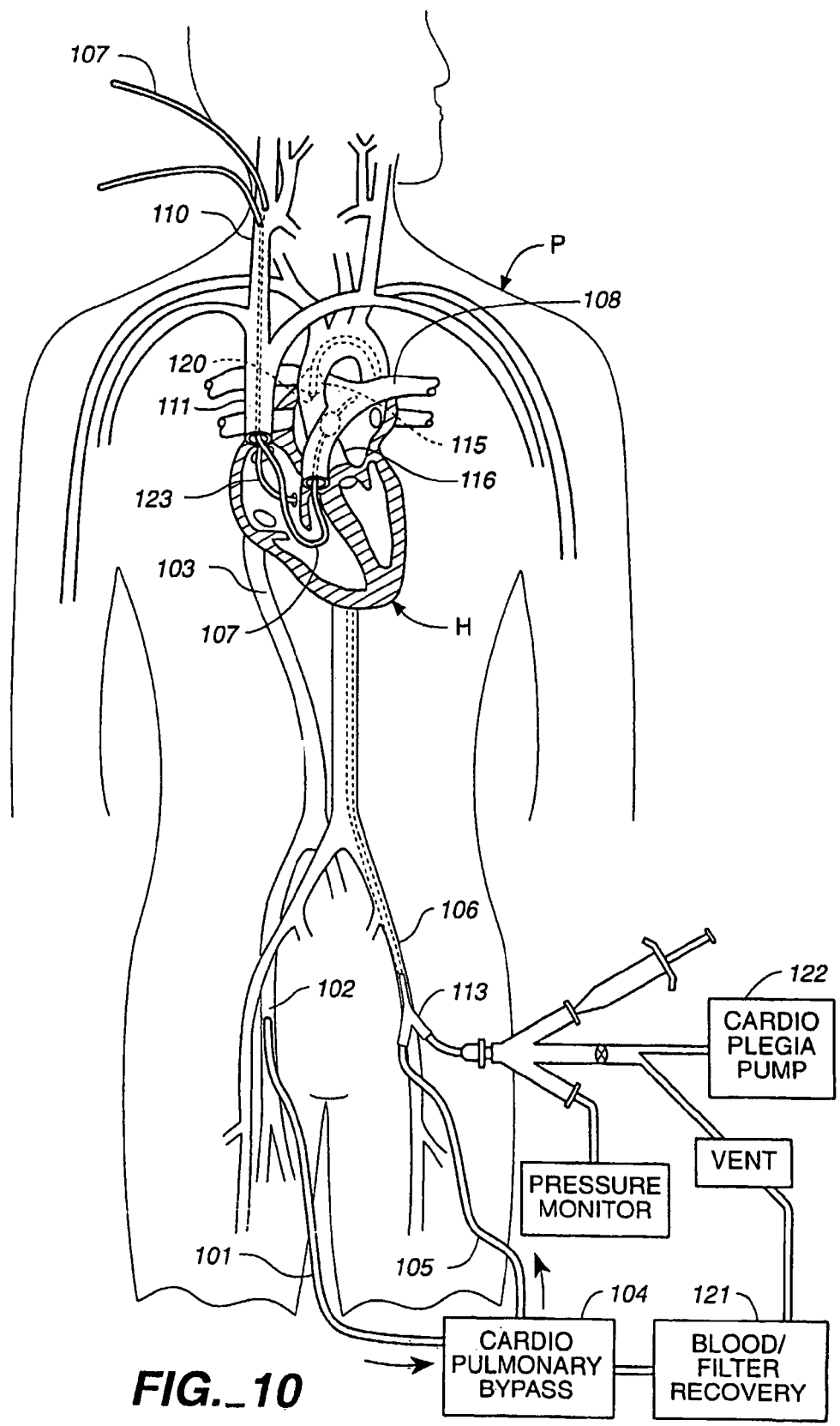
FIG._10

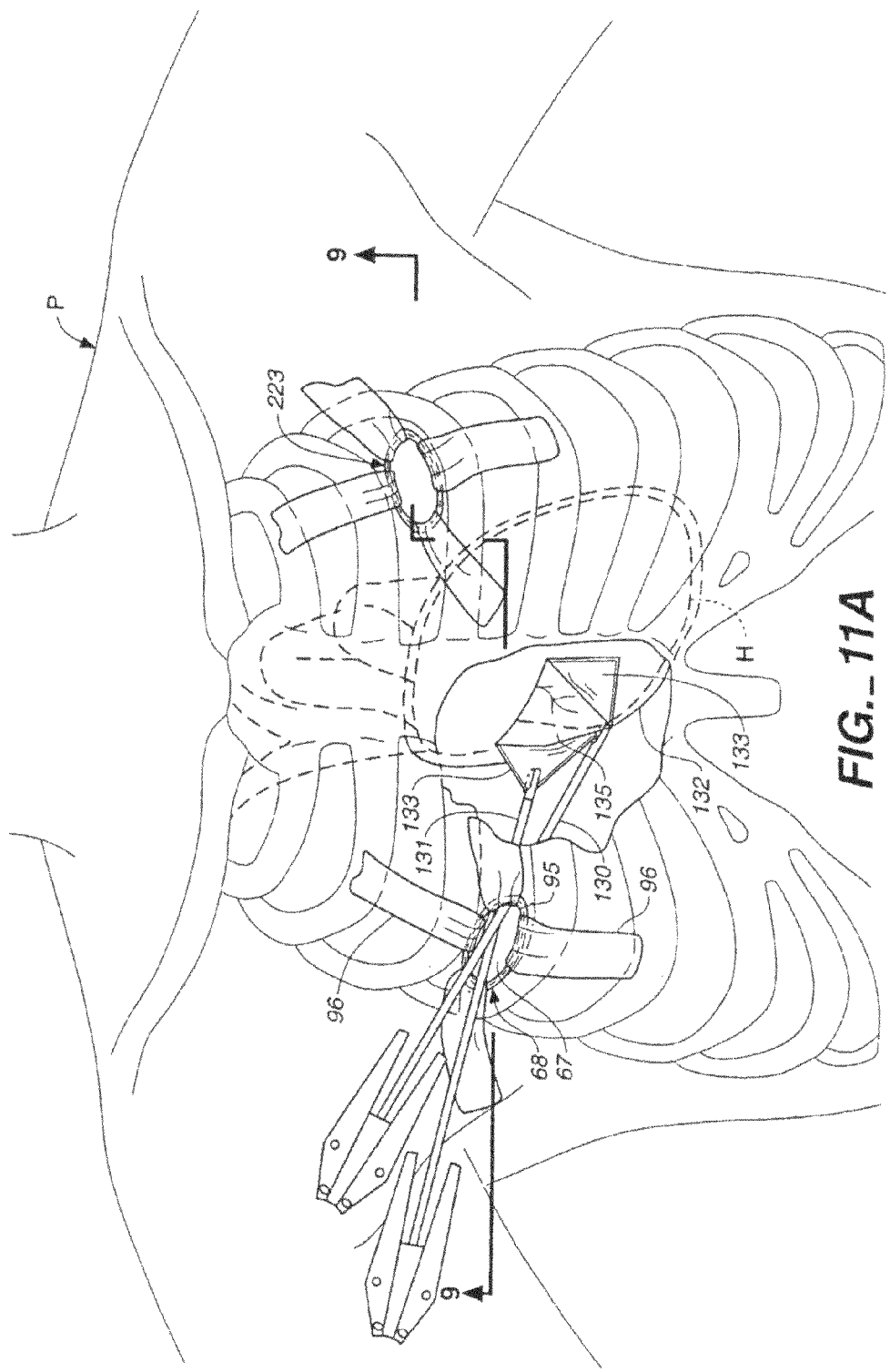
FIG._11A

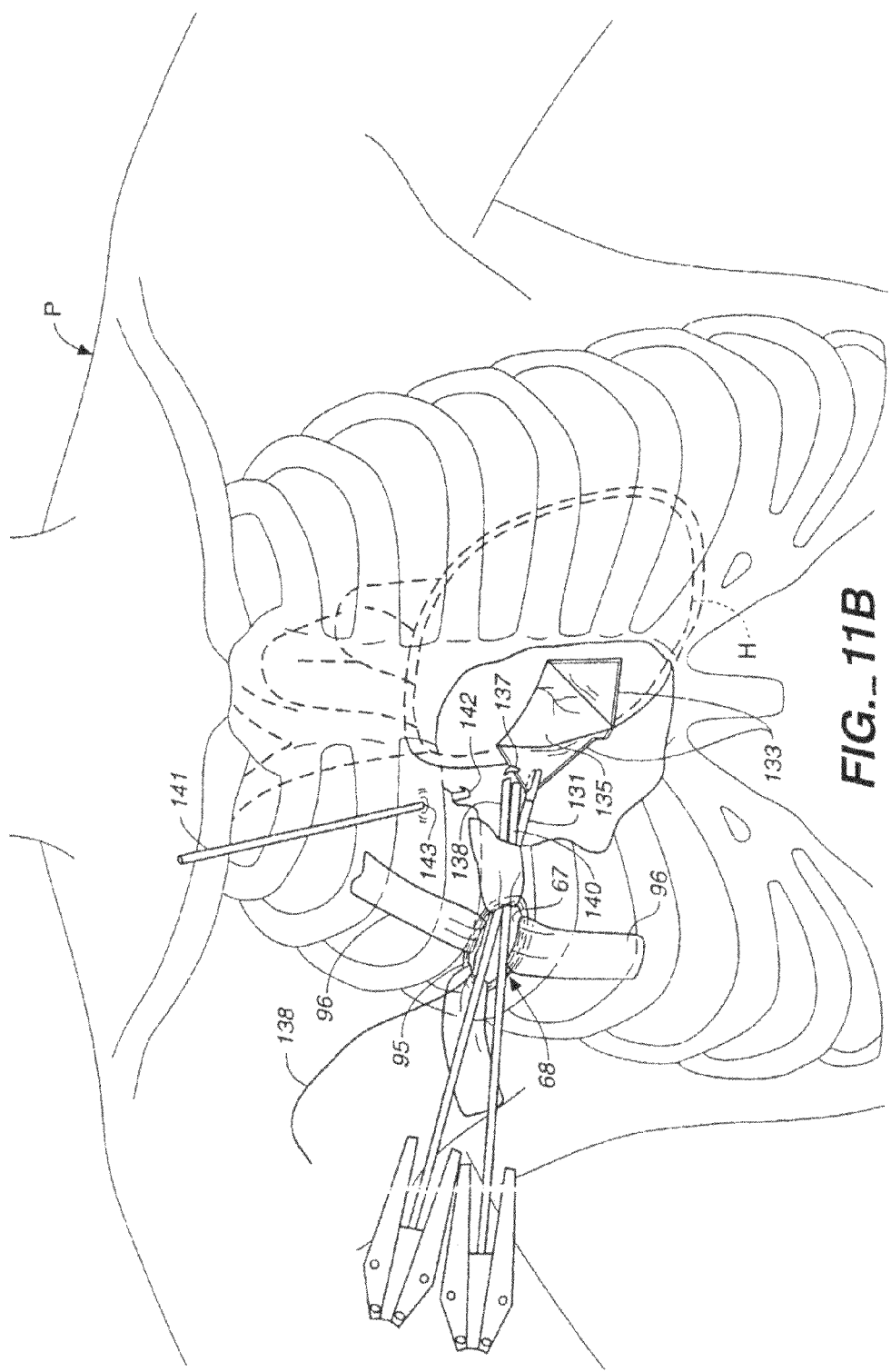
FIG._11B

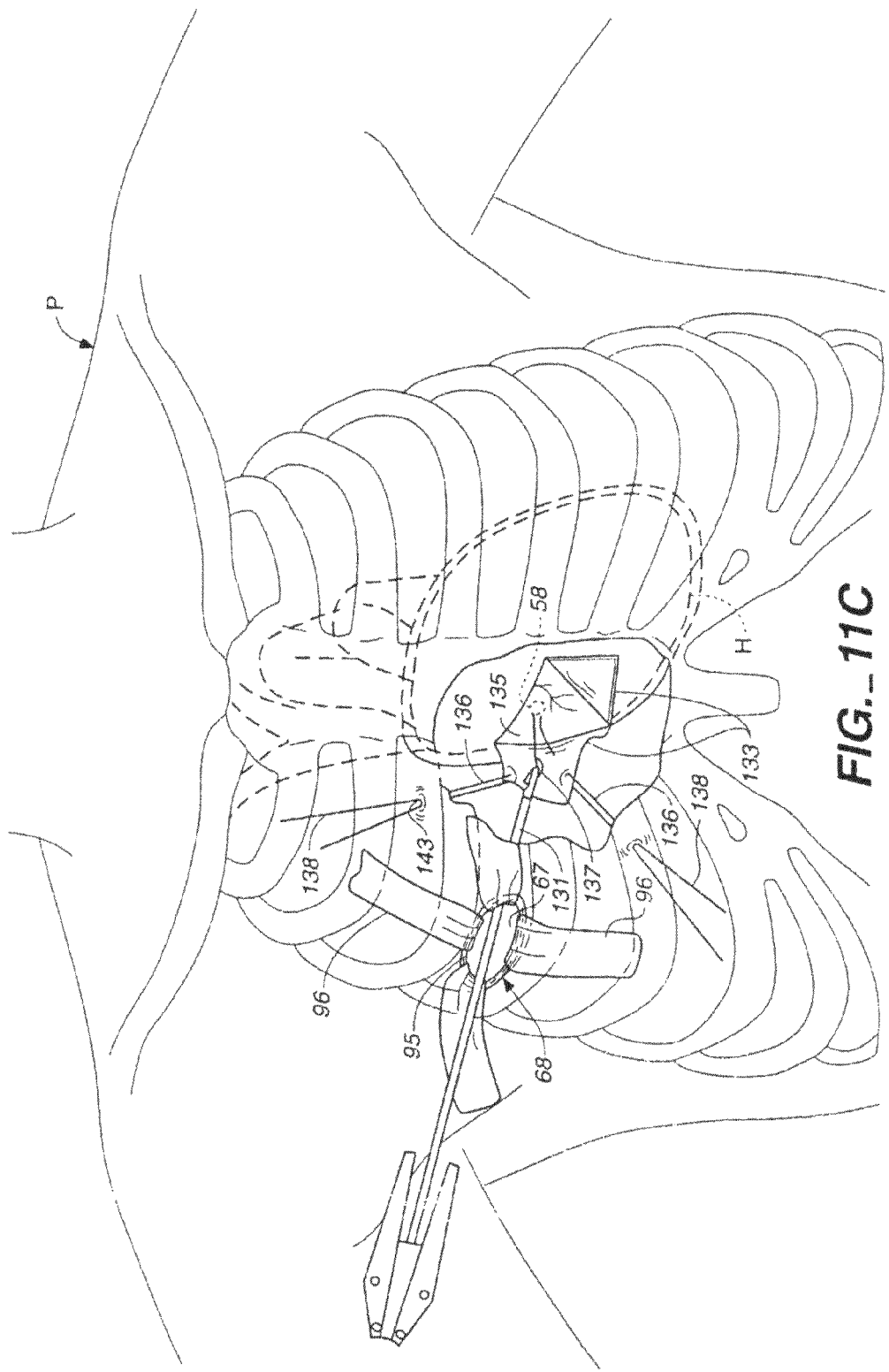
FIG._11C

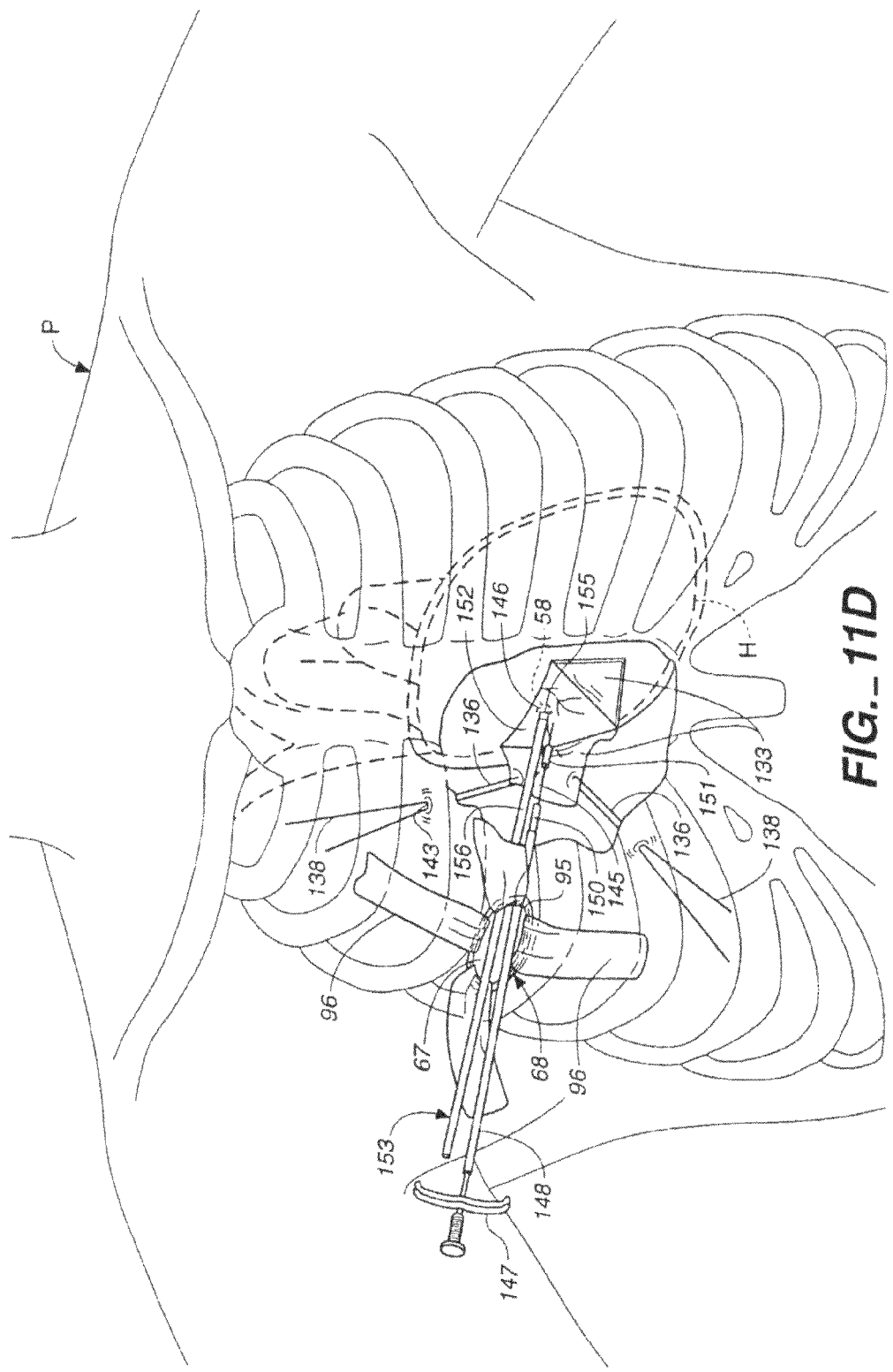
FIG._11D

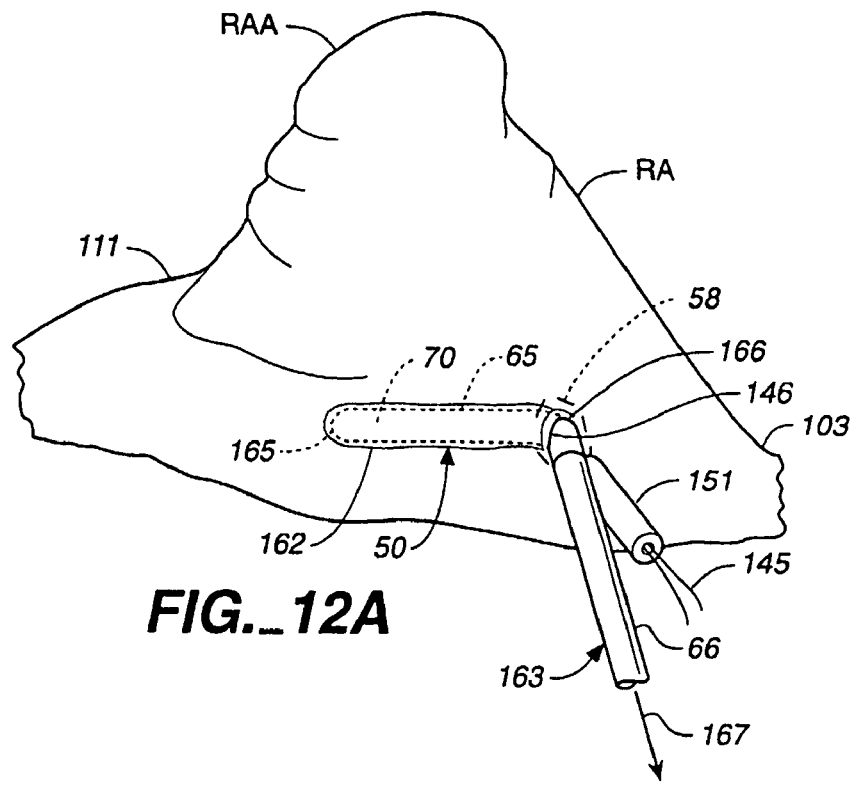
*FIG._12A*
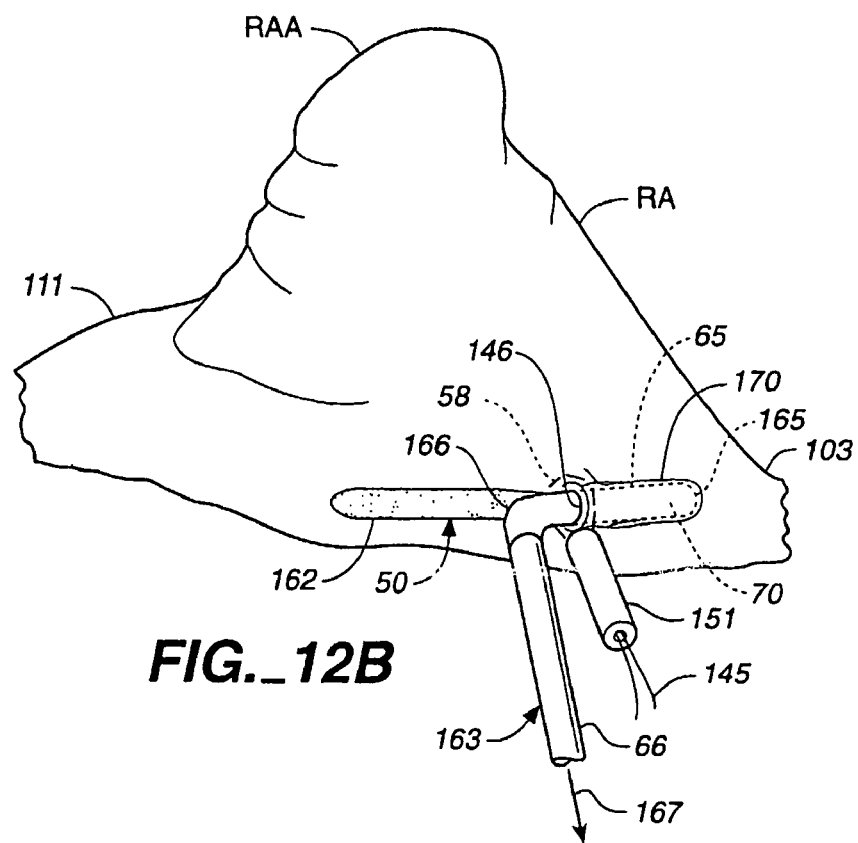
*FIG._12B*

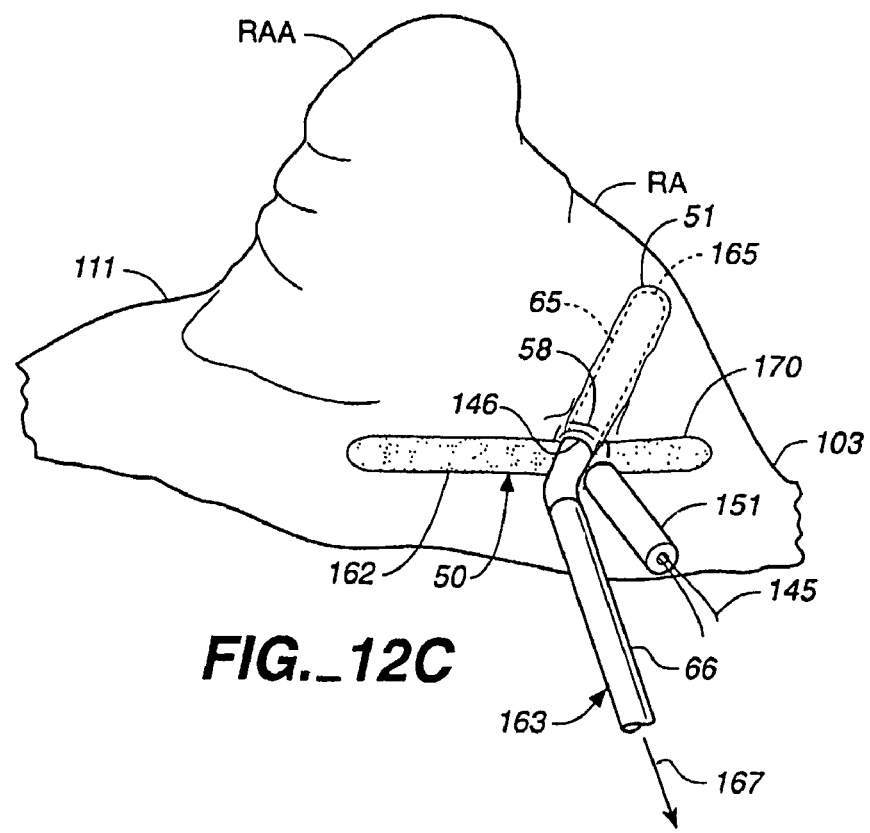
FIG._12C
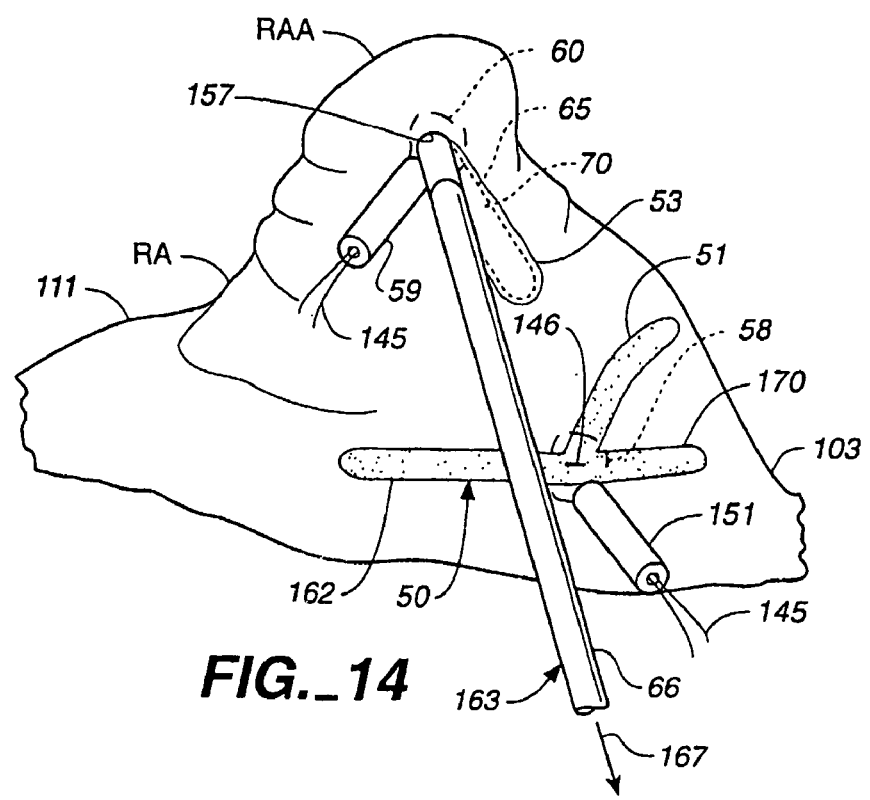
FIG._14

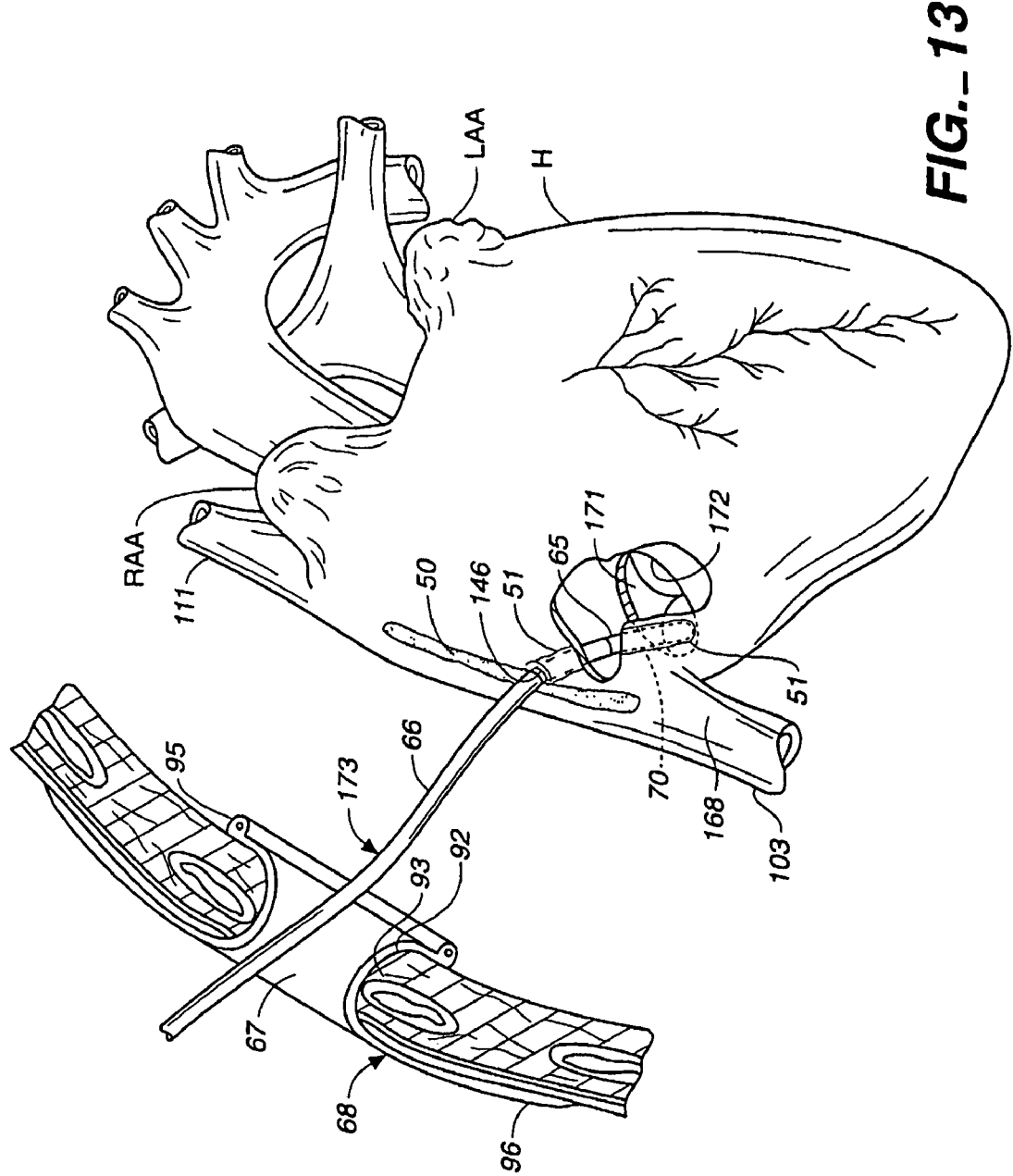
FIG._13

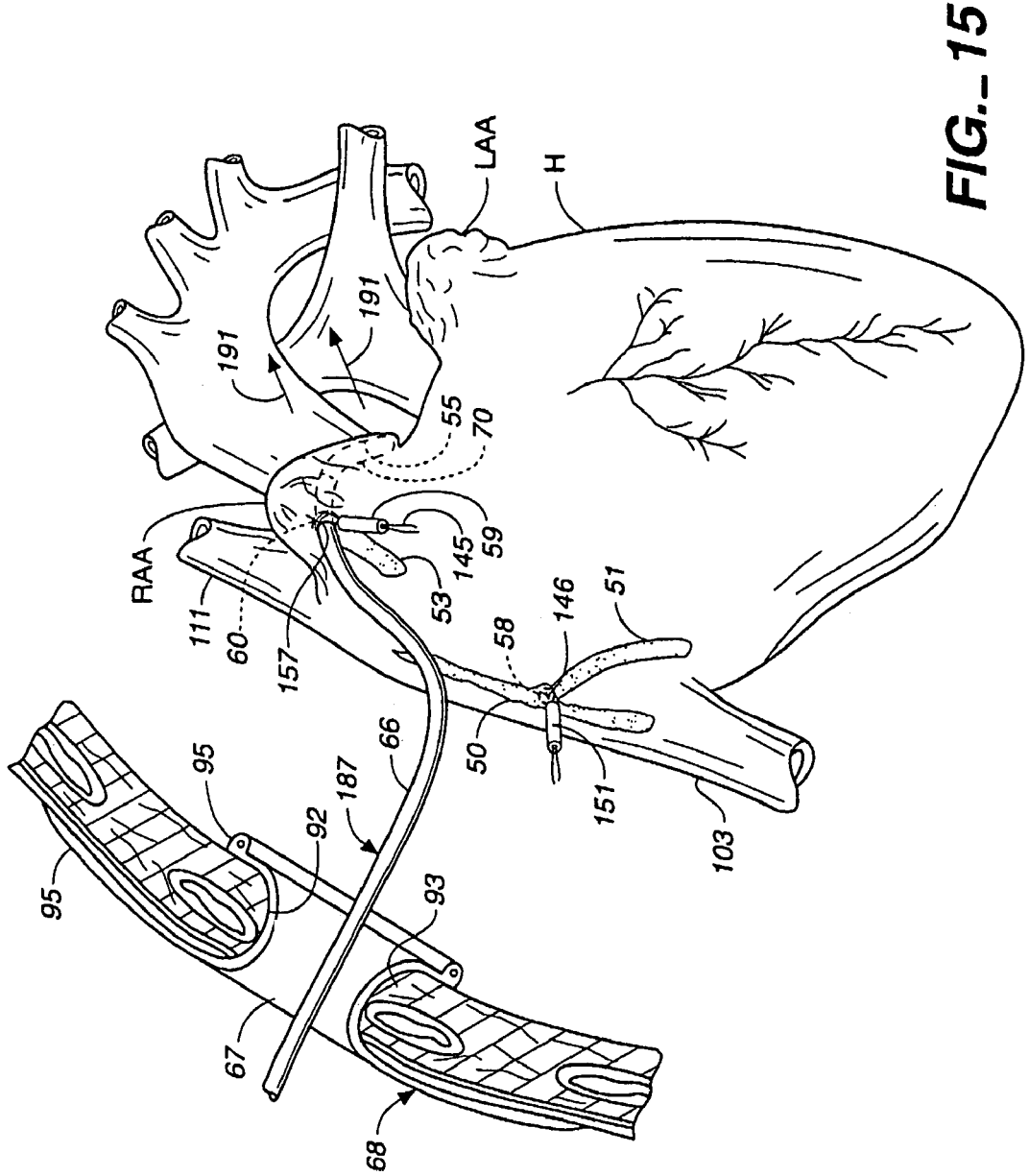
FIG._15

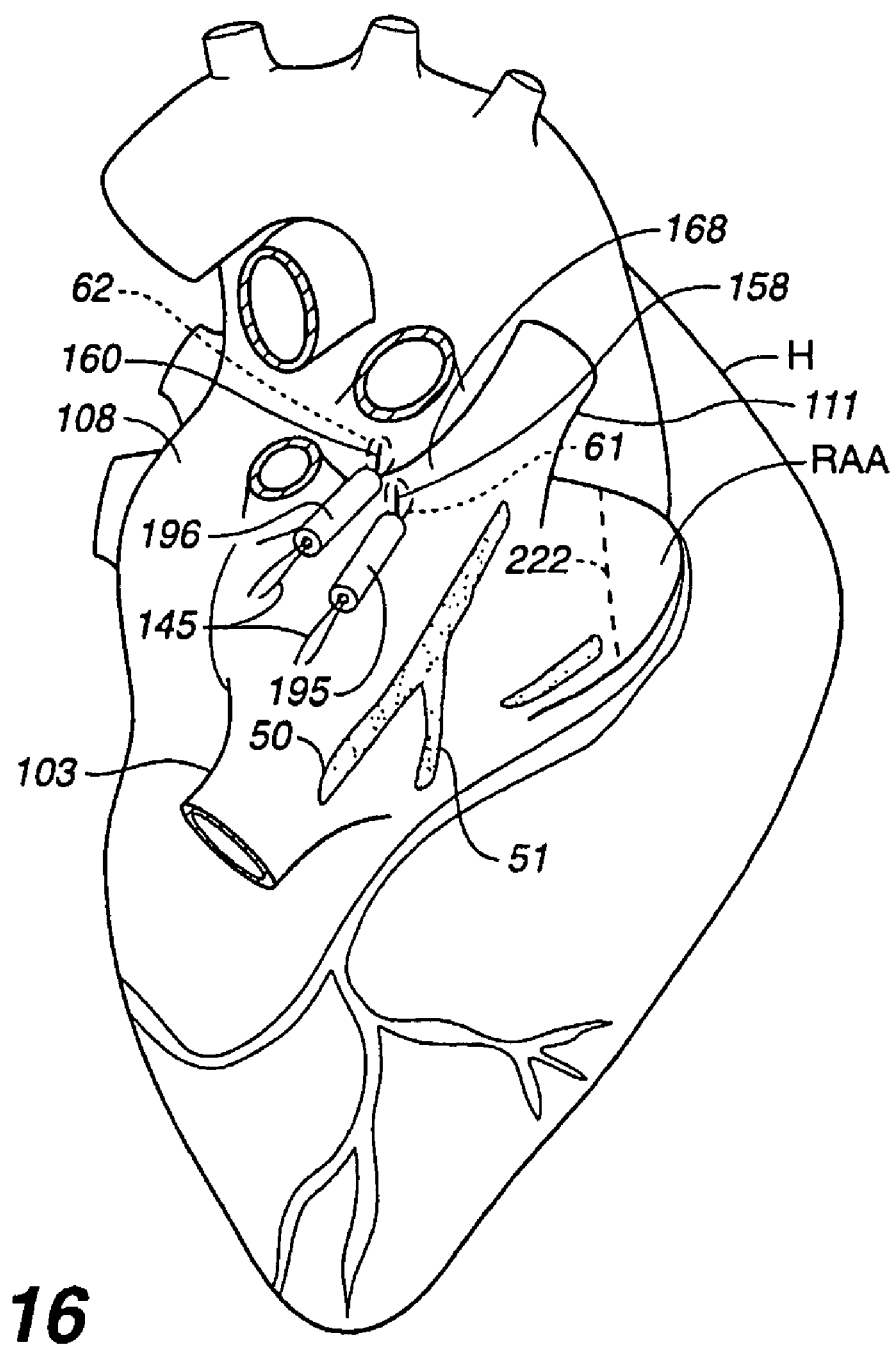
FIG._16

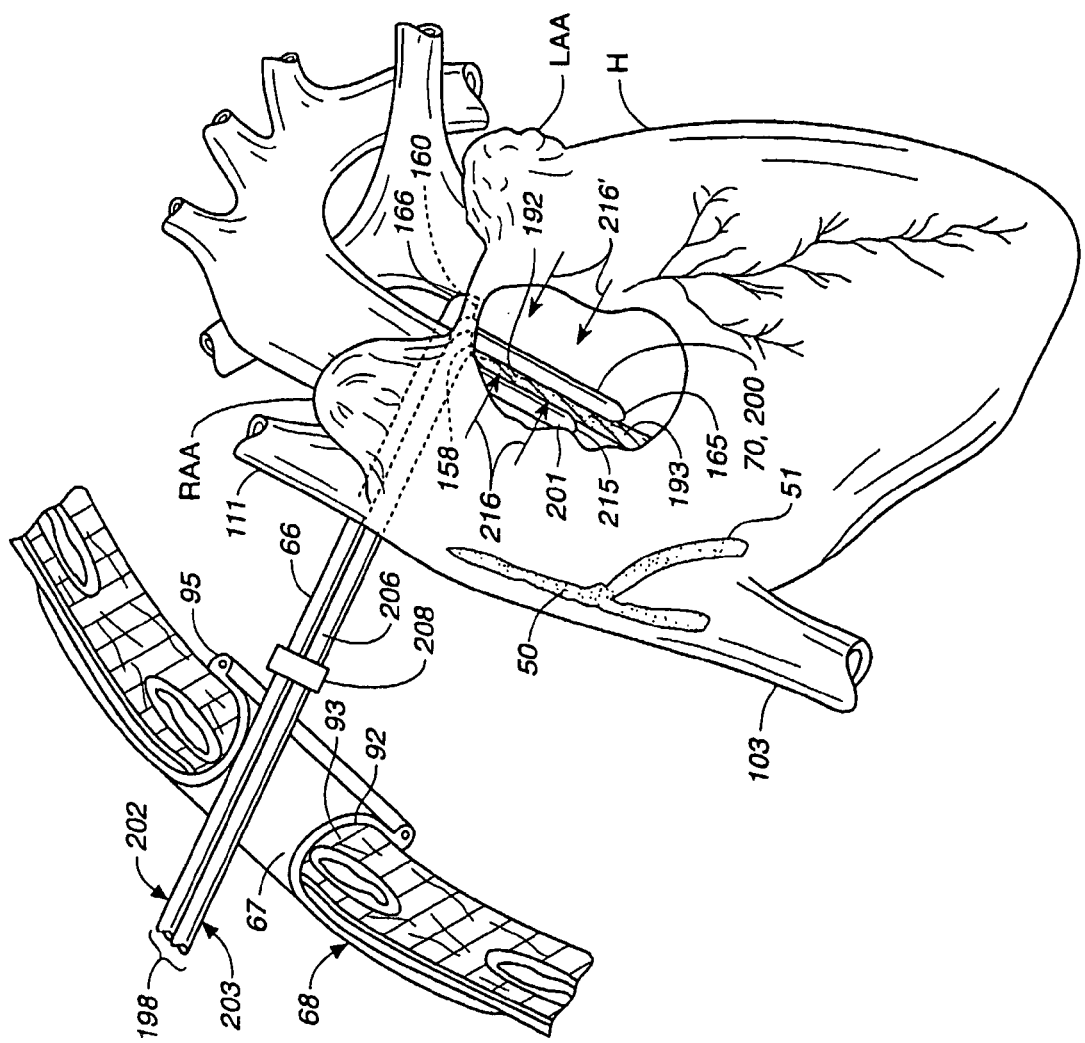
FIG._17

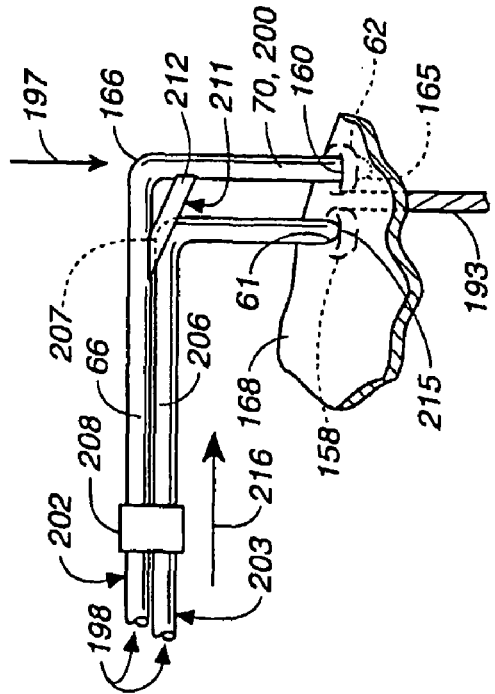
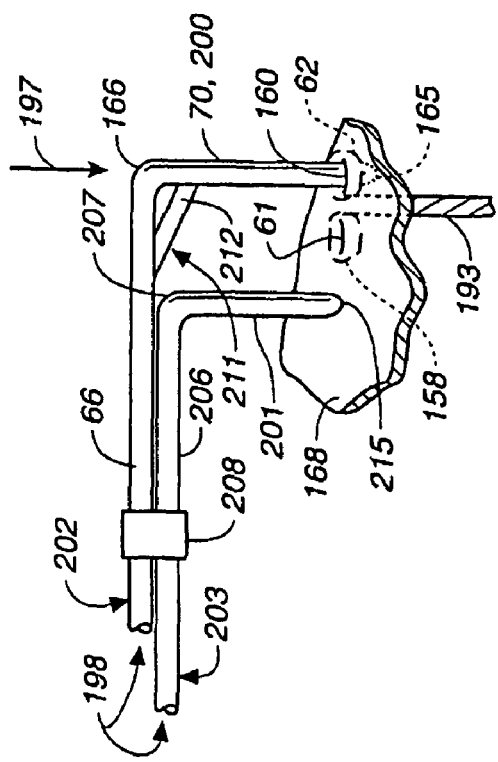

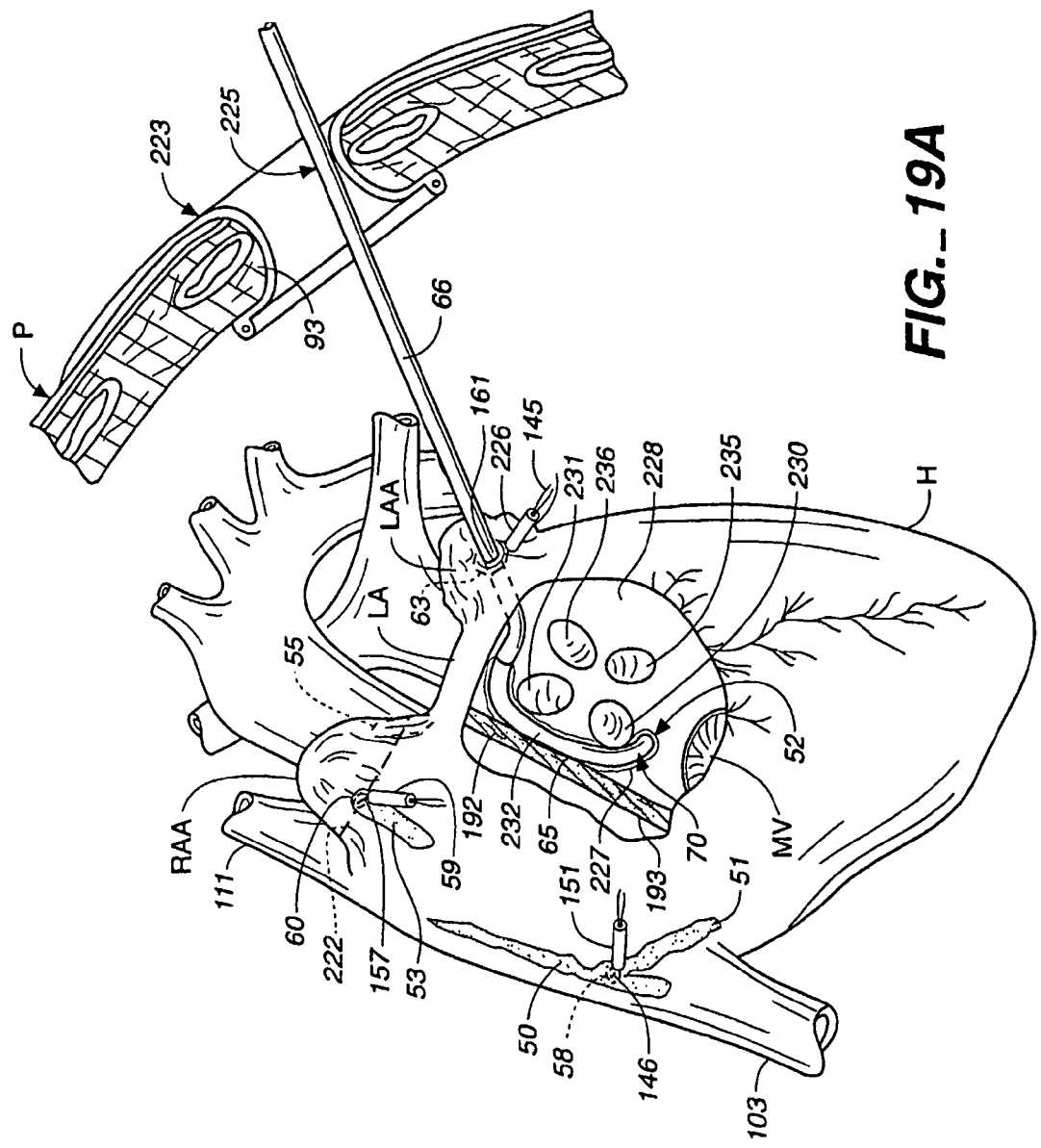
FIG._19A

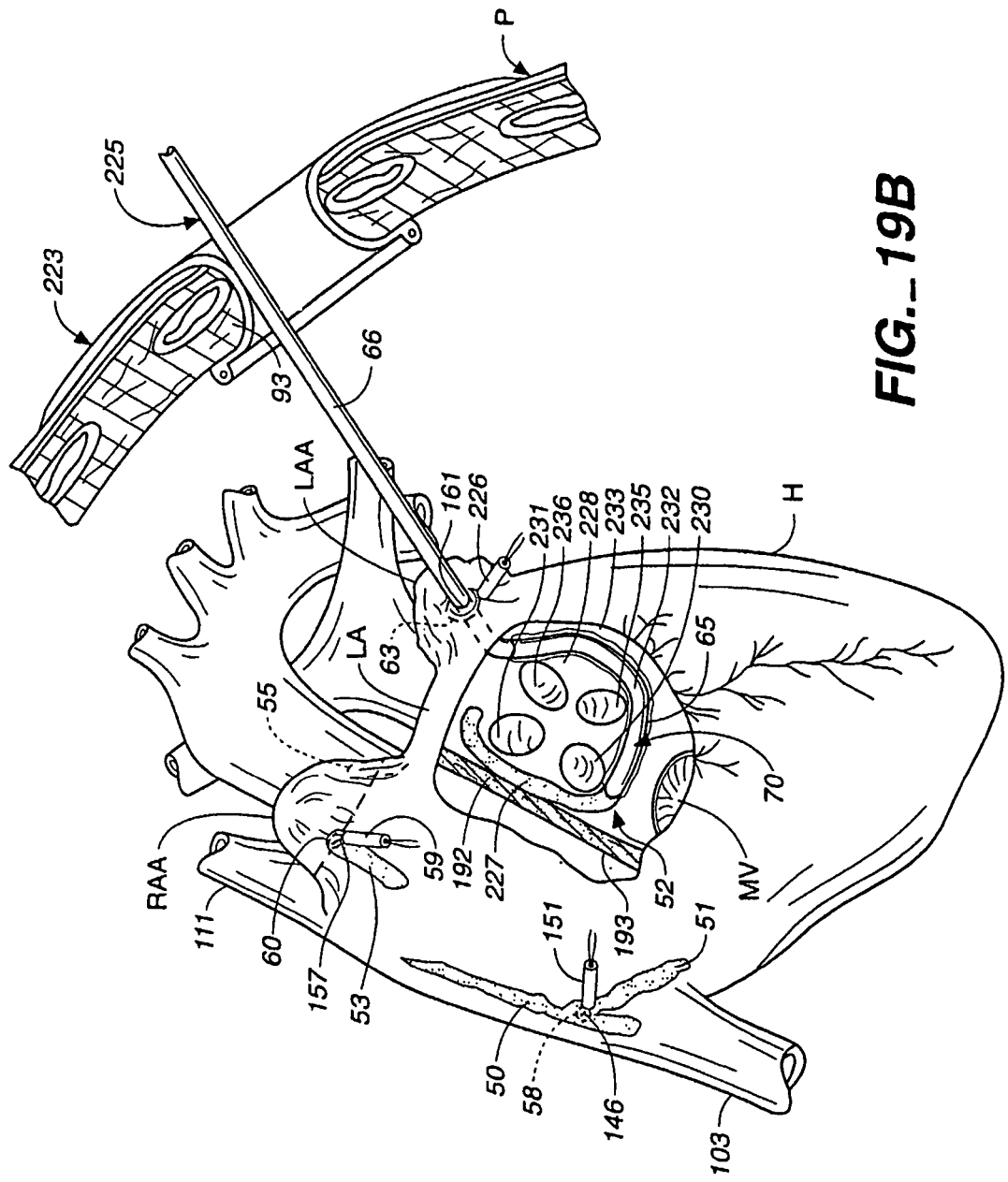
FIG._19B

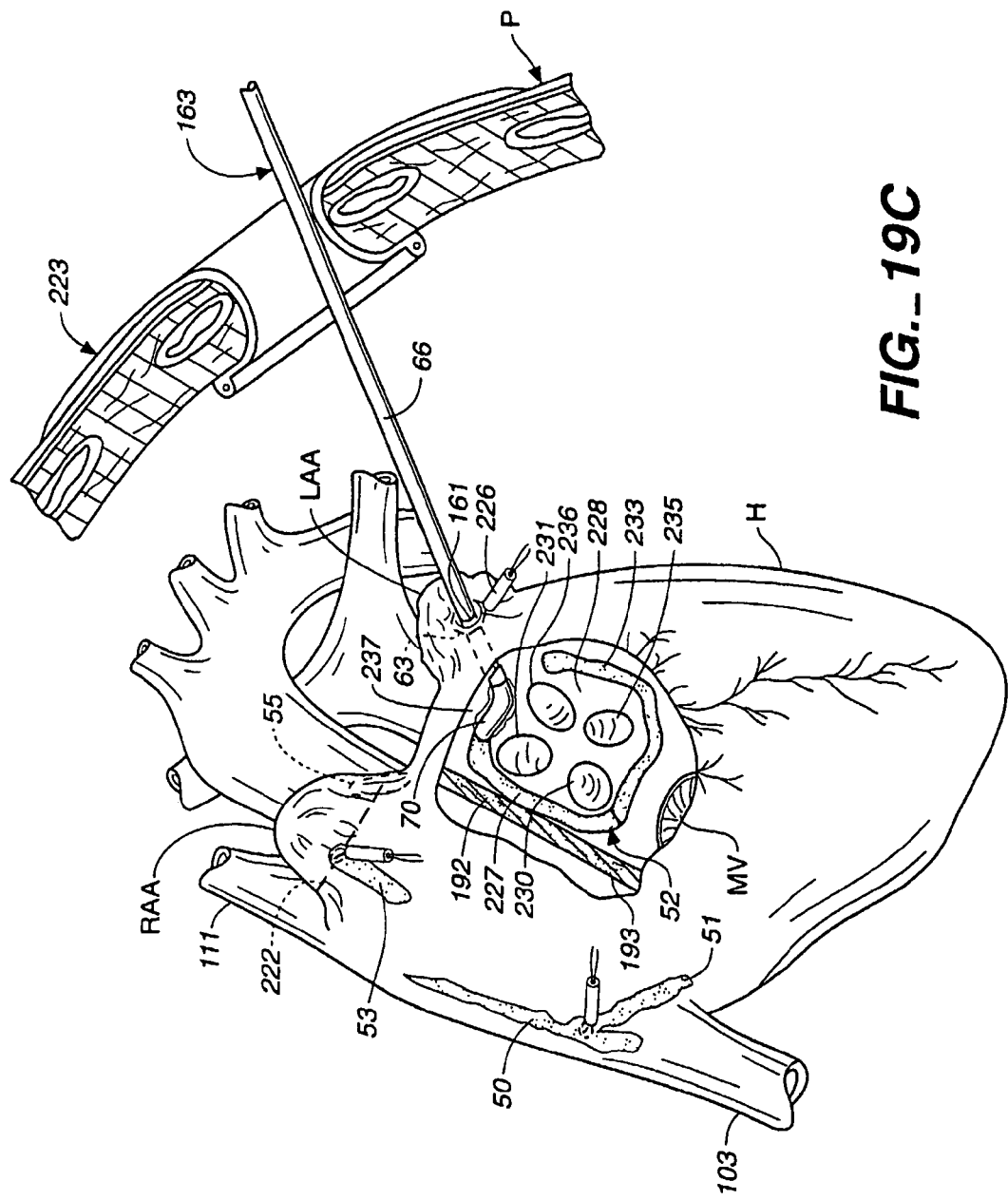
FIG._19C

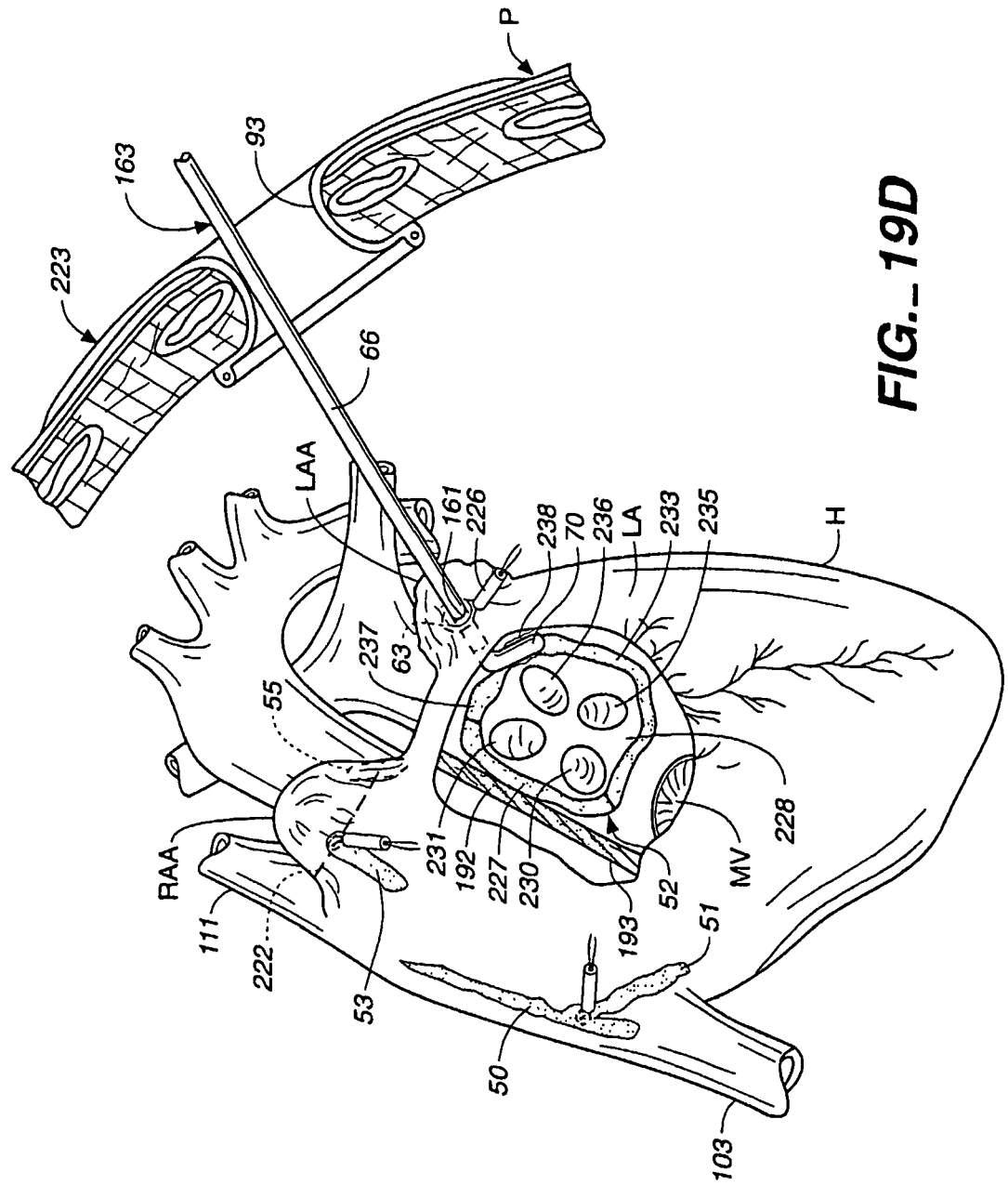
FIG._19D

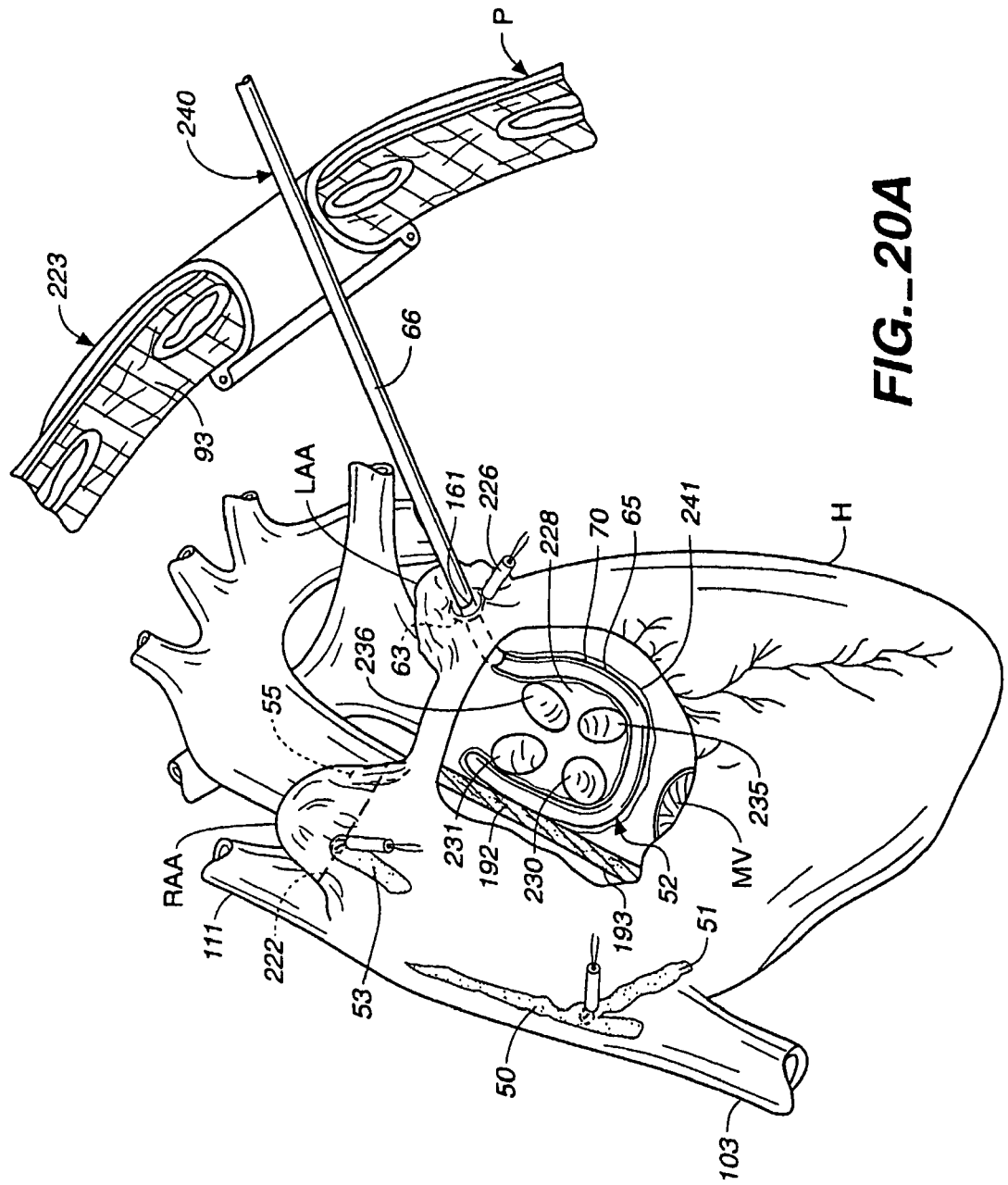
FIG._20A

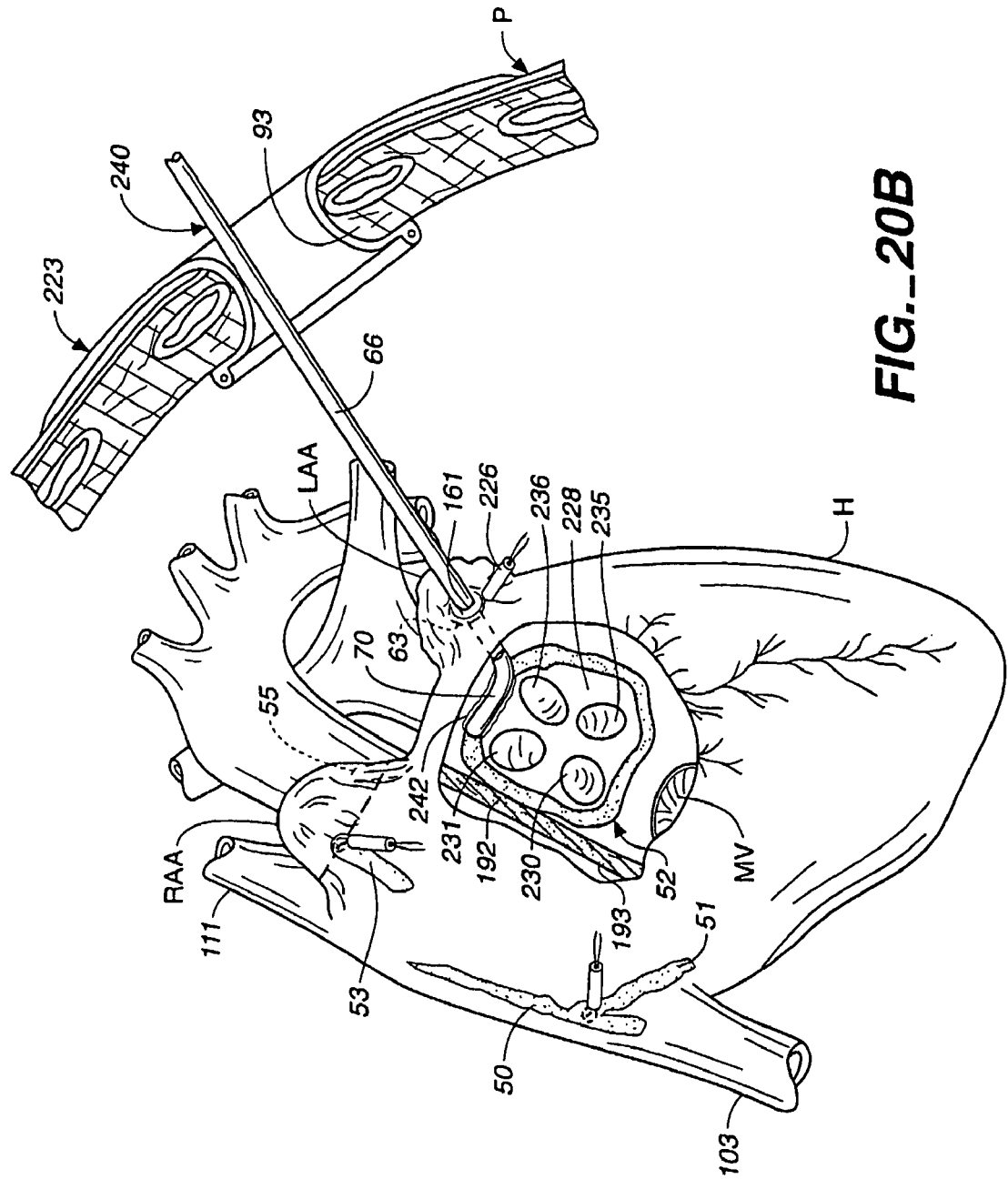
FIG._20B

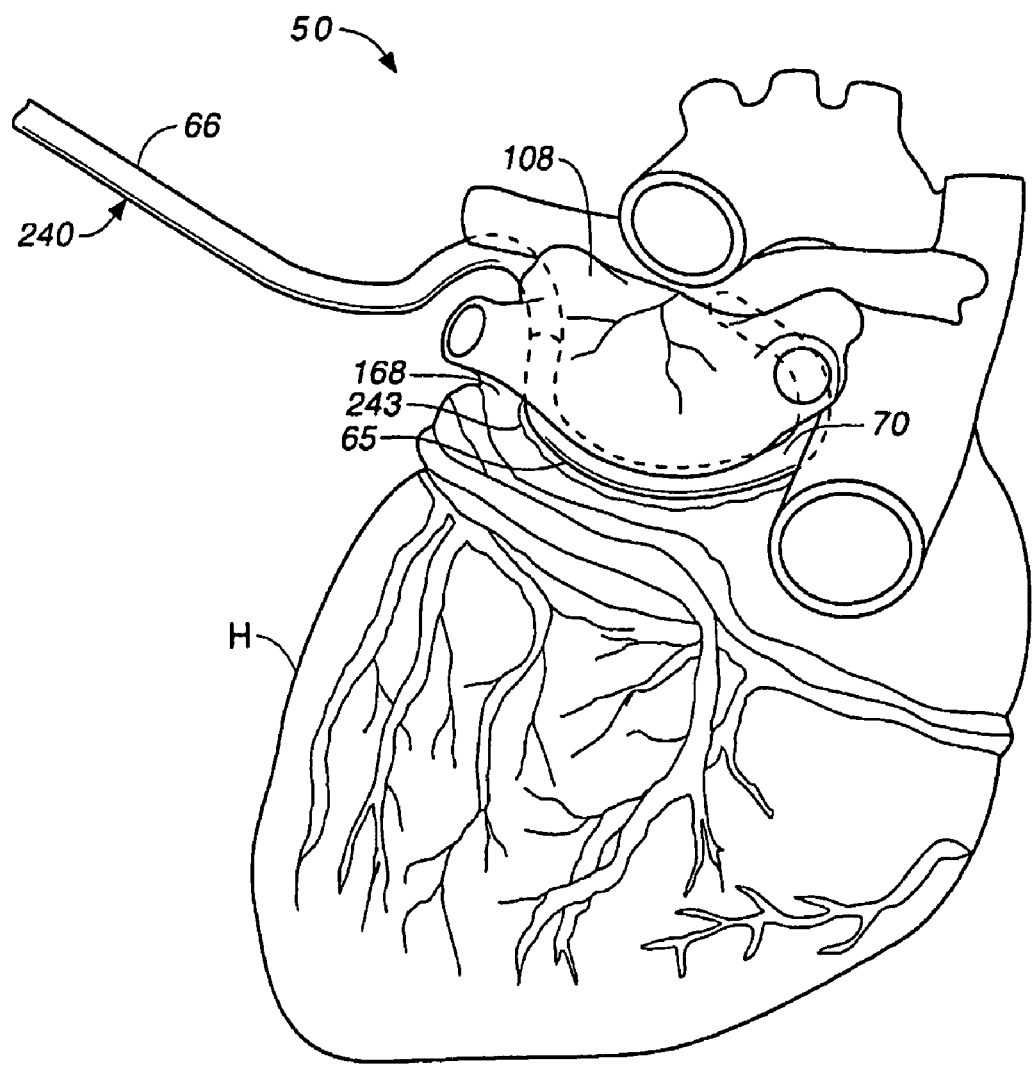
FIG._21

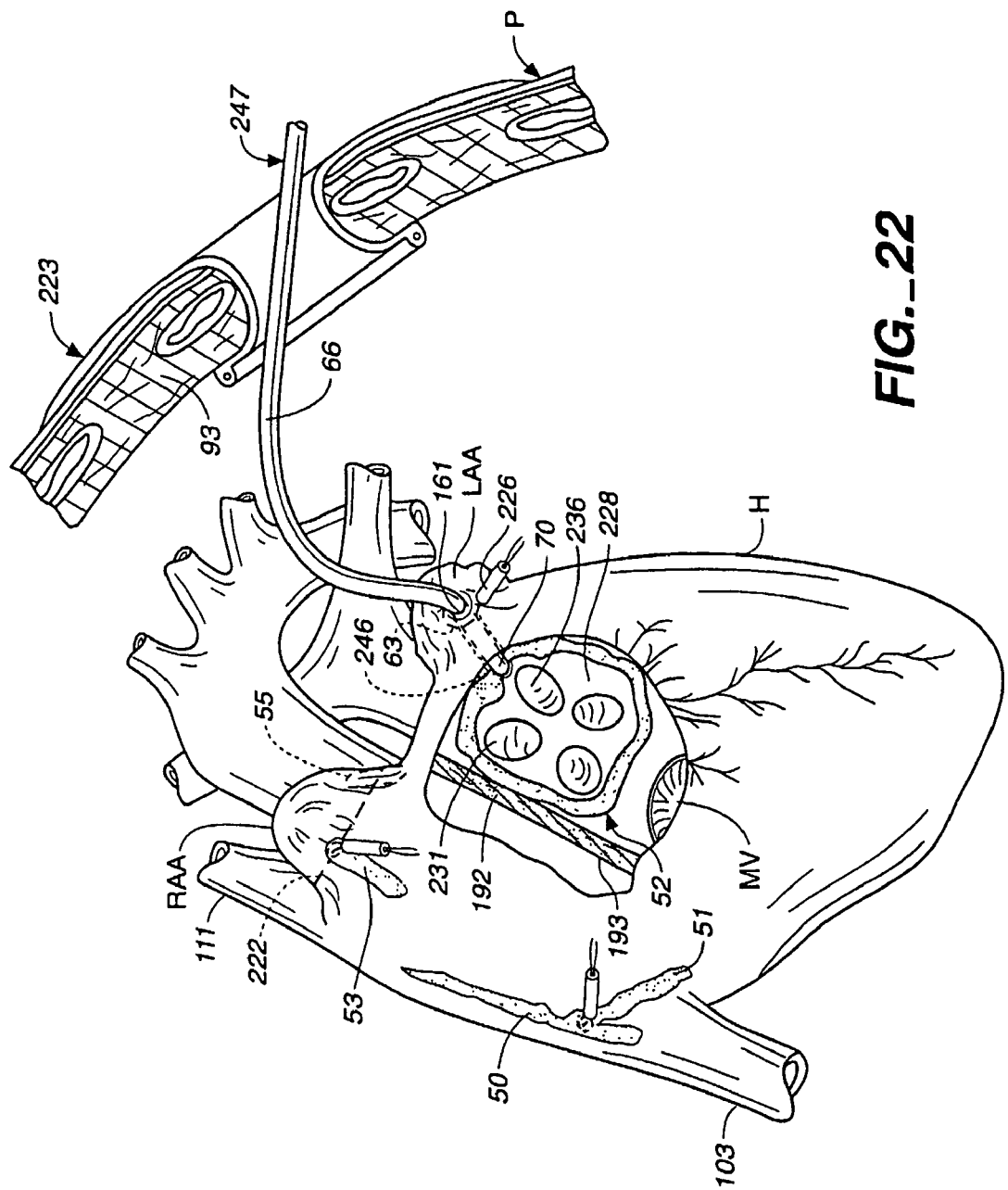
FIG._22

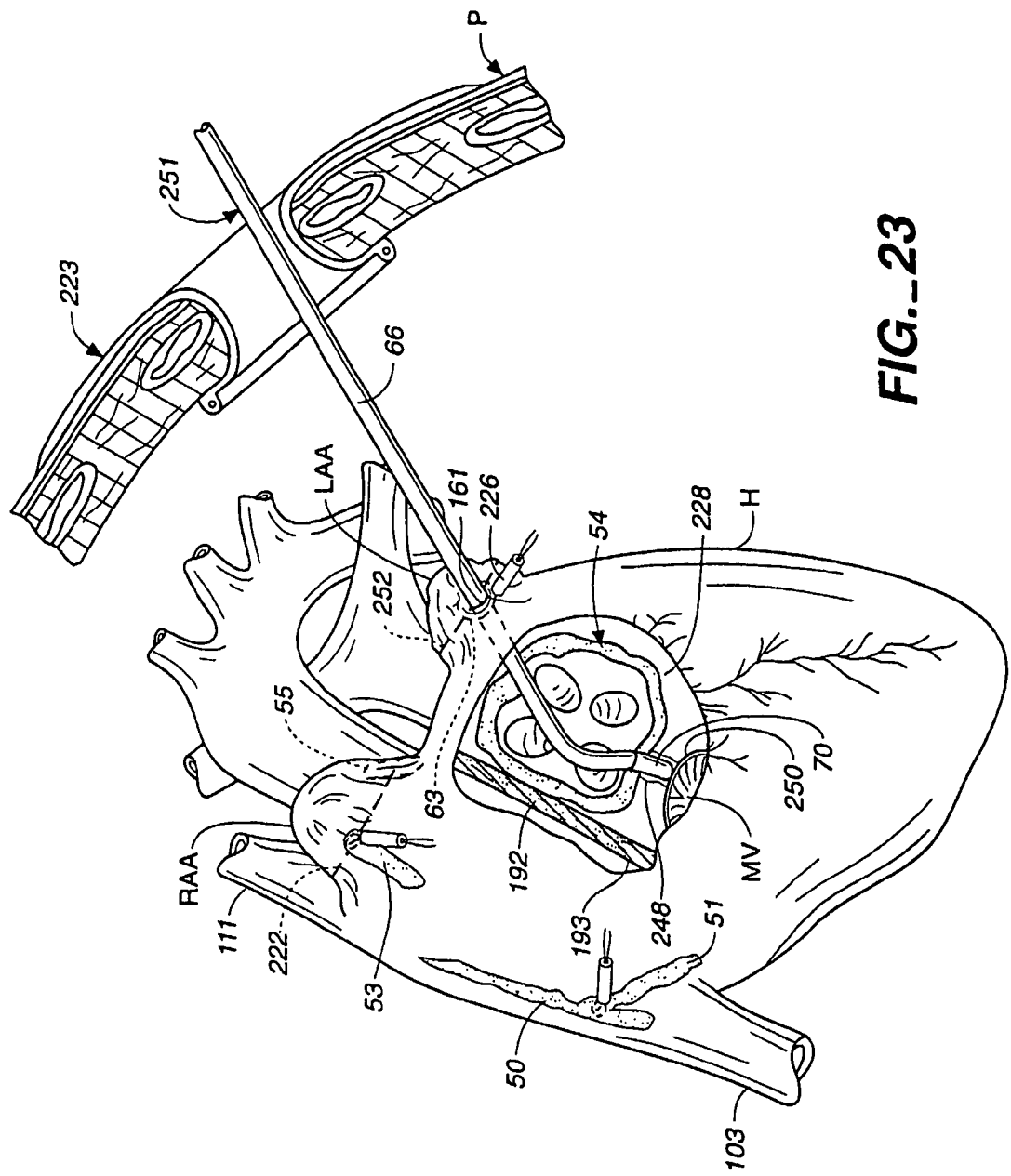
FIG._23

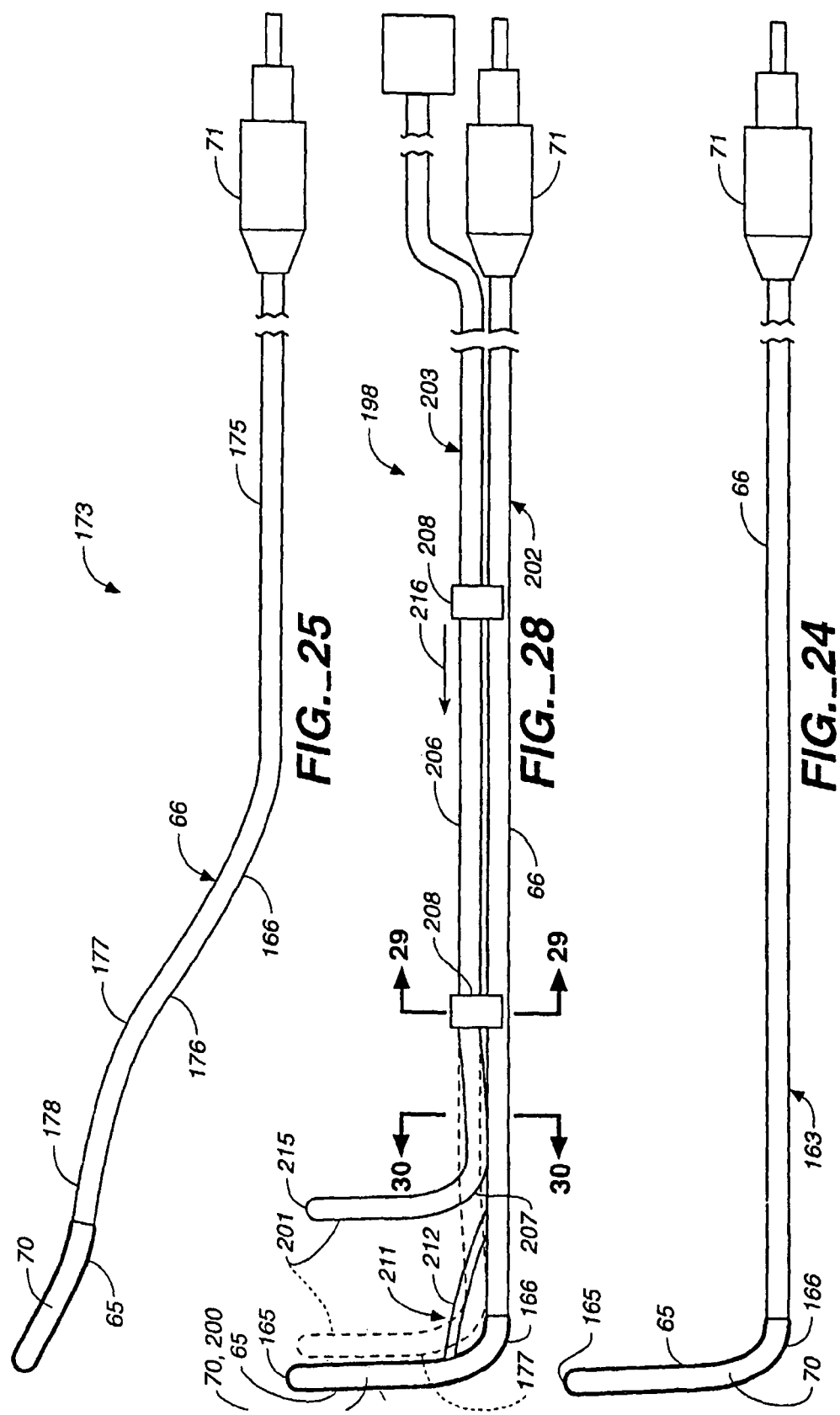

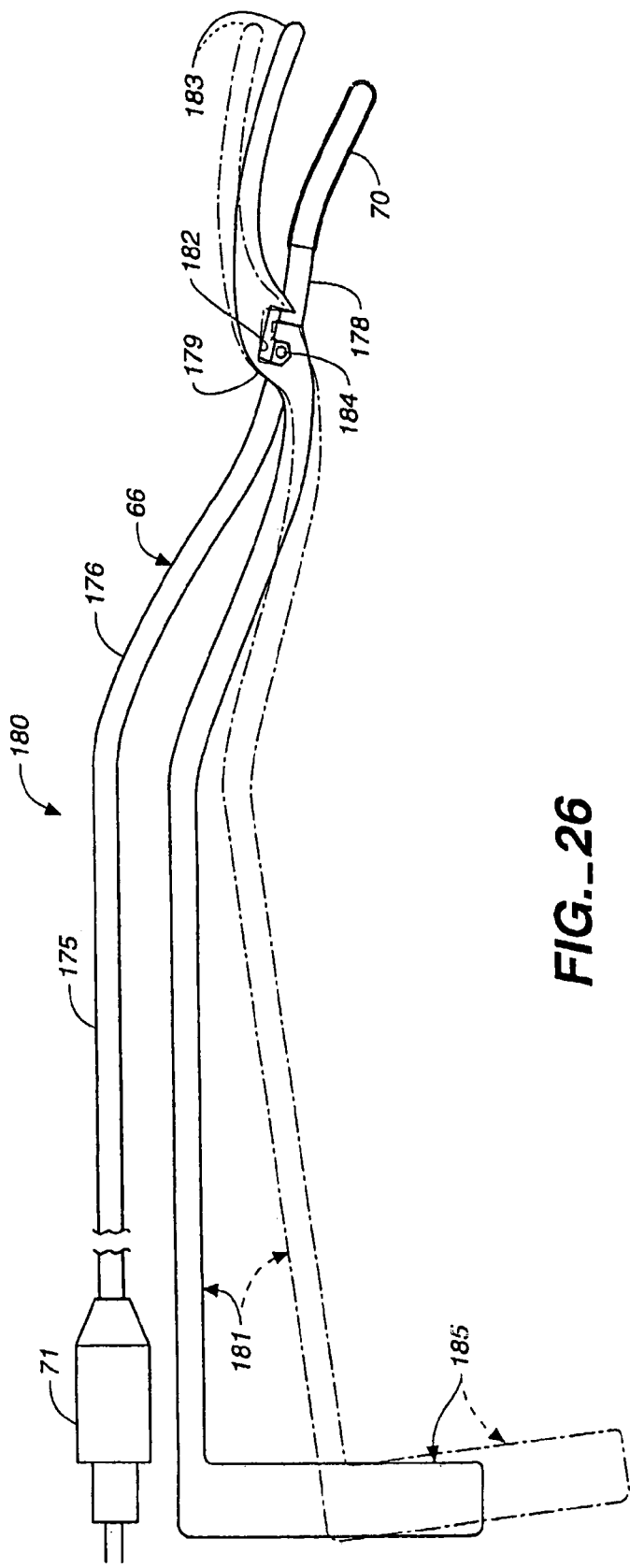
FIG._26

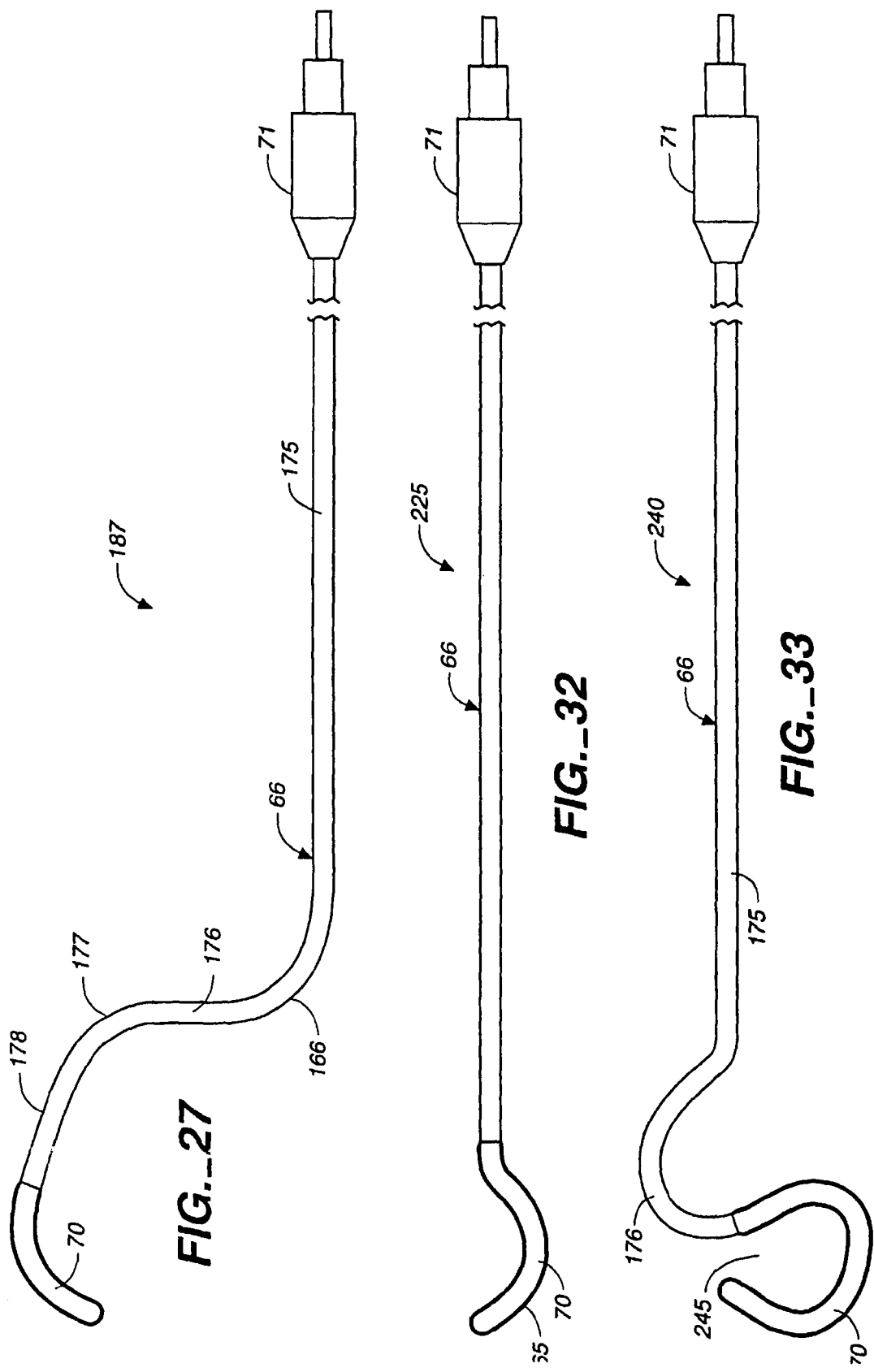

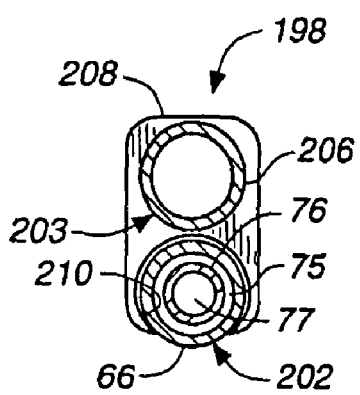
FIG._29
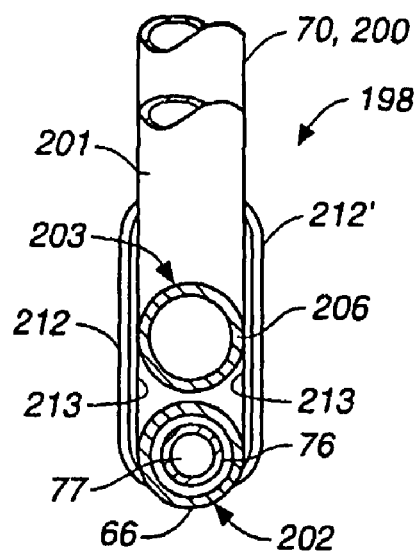
FIG._30
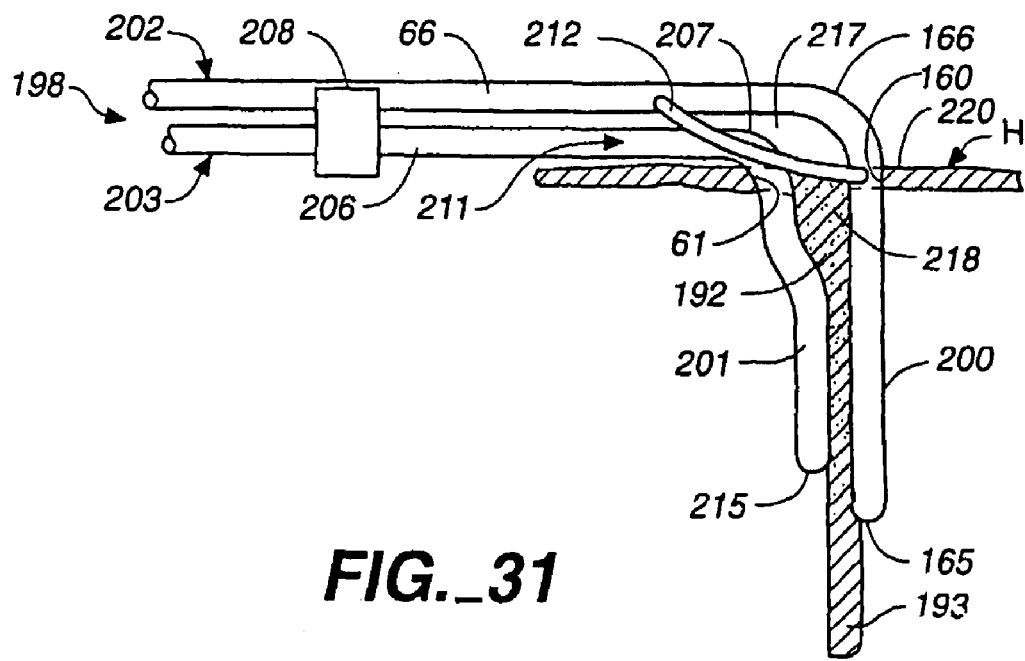
FIG._31

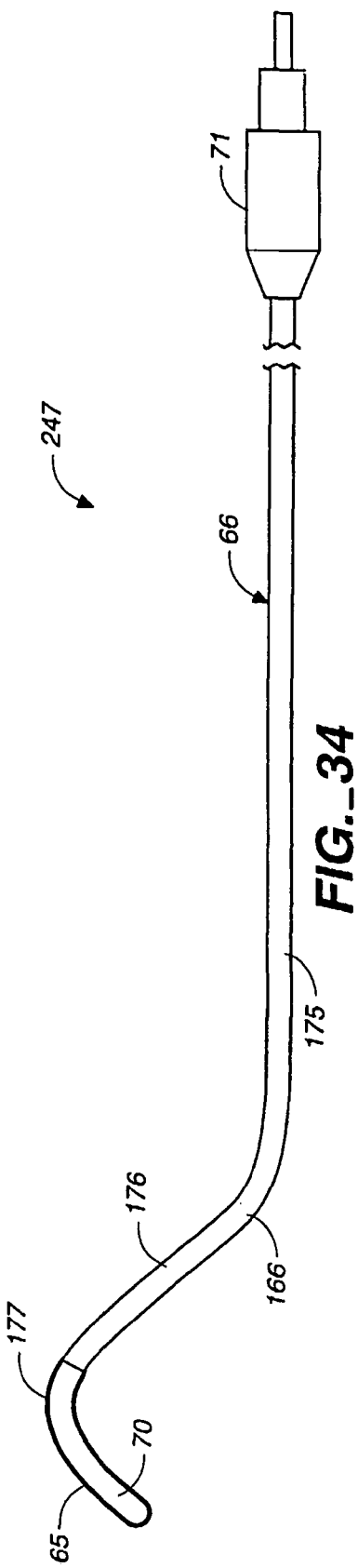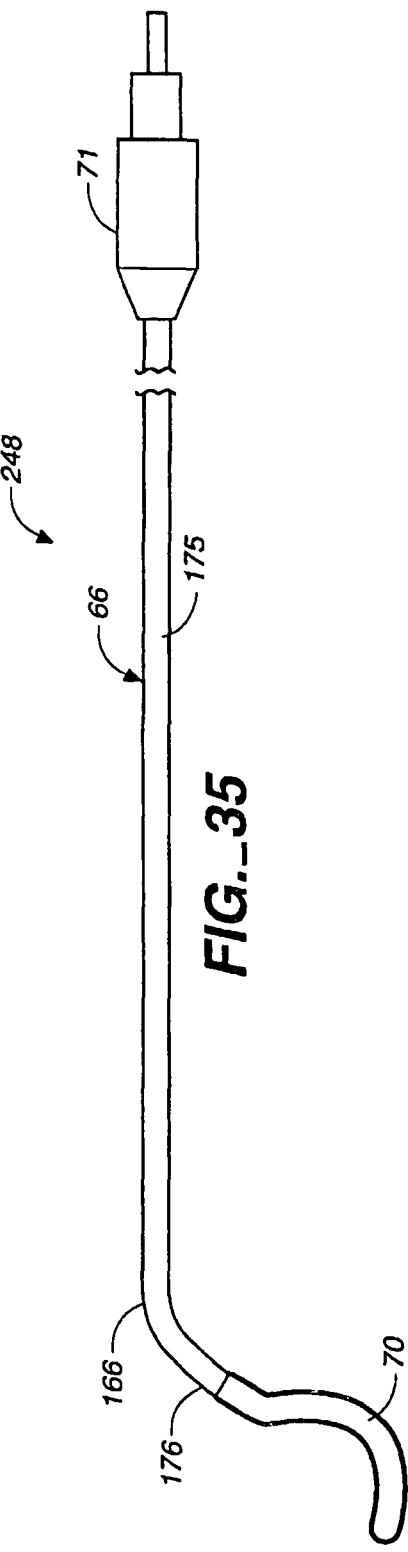

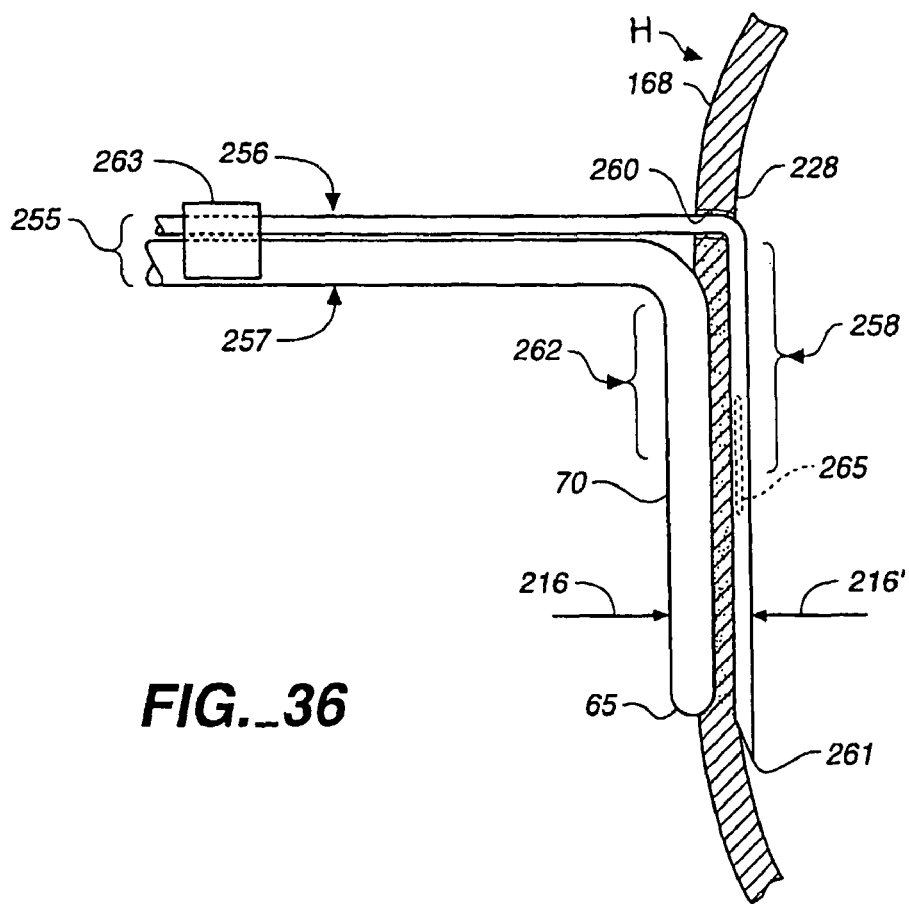
FIG._36
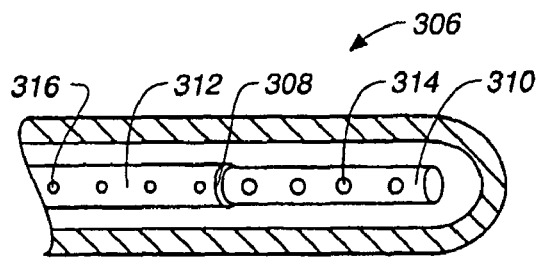
FIG._41
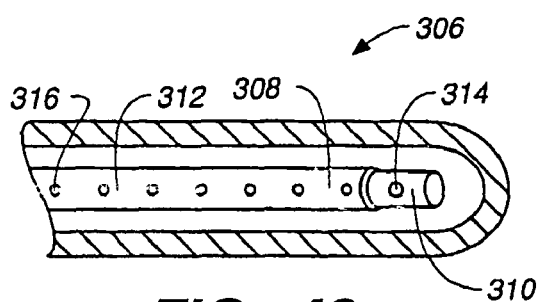
FIG._42

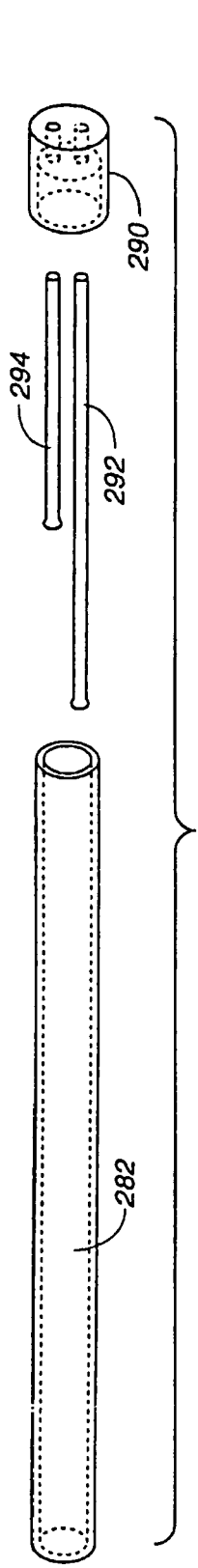
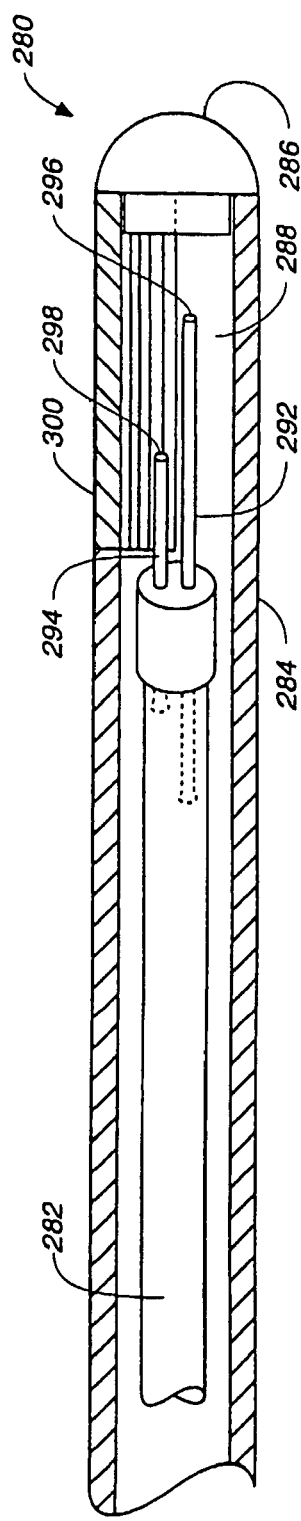
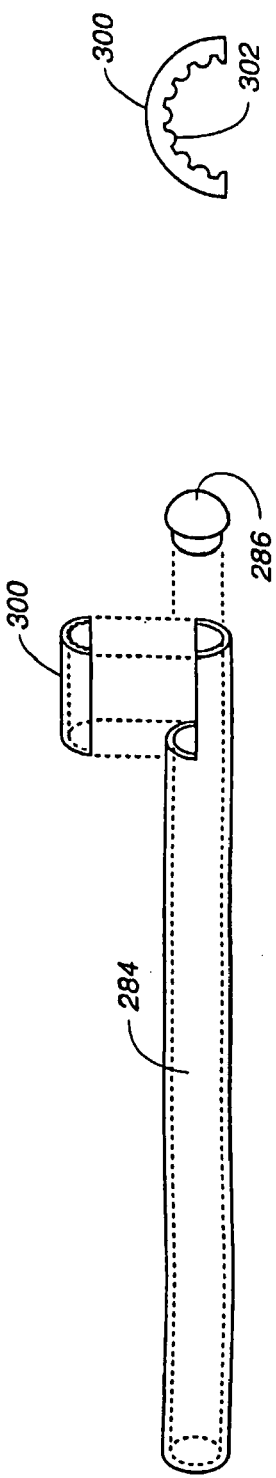
FIG._37
FIG._38
FIG._39
FIG._40

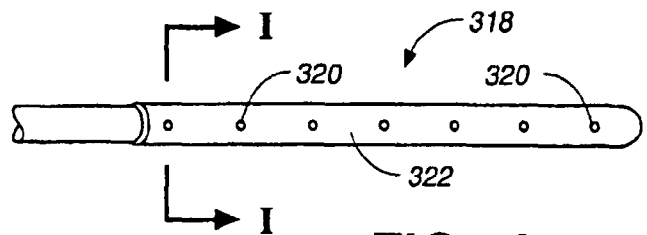
FIG._43
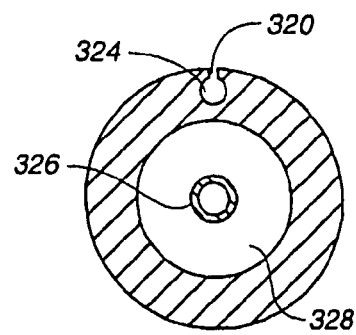
FIG._44
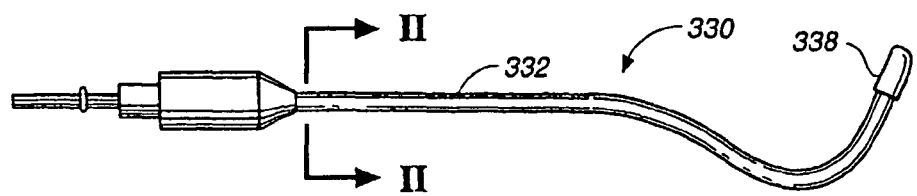
FIG._45
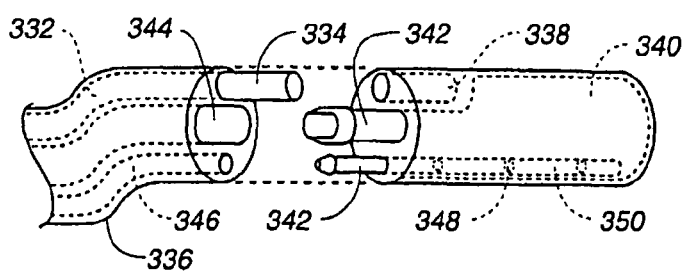
FIG._46
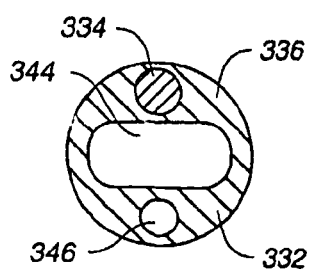
FIG._47

SURGICAL SYSTEM AND PROCEDURE FOR TREATMENT OF MEDICALLY REFRACTORY ATRIAL FIBRILLATION

CROSS-REFERENCE TO RELATED APPLICATIONS

This application is a continuation of U.S. application Ser. No. 10/171,411, filed 12 Jun. 2002 now U.S. Pat. No. 7,387,126, which is a continuation of U.S. application Ser. No. 09/606,742, filed 29 Jun. 2000, now abandoned, which is a continuation of U.S. application Ser. No. 08/943,683, filed 15 Oct. 1997, now U.S. Pat. No. 6,161,543. This application is also related to U.S. application Ser. No. 11/785,428, filed 17 Apr. 2007, and U.S. application Ser. No. 11/785,427, filed 17 Apr. 2007. All of the foregoing are hereby incorporated by reference as though fully set forth herein.

BACKGROUND OF THE INVENTION

It is well documented that atrial fibrillation, either alone or as a consequence of other cardiac disease, continues to persist as the most common cardiac arrhythmia. According to recent estimates, more than one million people in the U.S. suffer from this common arrhythmia, roughly 0.15% to 1.0% of the population. Moreover, the prevalence of this cardiac disease increases with age, affecting nearly 8% to 17% of those over 60 years of age.

Although atrial fibrillation may occur alone, this arrhythmia often associates with numerous cardiovascular conditions, including congestive heart failure, hypertensive cardiovascular disease, myocardial infarction, rheumatic heart disease and stroke. Regardless, three separate detrimental sequelae result: (1) a change in the ventricular response, including the onset of an irregular ventricular rhythm and an increase in ventricular rate; (2) detrimental hemodynamic consequences resulting from loss of atrioventricular synchrony, decreased ventricular filling time, and possible atrioventricular valve regurgitation; and (3) an increased likelihood of sustaining a thromboembolic event because of loss of effective contraction and atrial stasis of blood in the left atrium.

Atrial arrhythmia may be treated using several methods. Pharmacological treatment of atrial fibrillation, for example, is initially the preferred approach, first to maintain normal sinus rhythm, or secondly to decrease the ventricular response rate. While these medications may reduce the risk of thrombus collecting in the atrial appendages if the atrial fibrillation can be converted to sinus rhythm, this form of treatment is not always effective. Patients with continued atrial fibrillation and only ventricular rate control continue to suffer from irregular heartbeats and from the effects of impaired hemodynamics due to the lack of normal sequential atrioventricular contractions, as well as continue to face a significant risk of thromboembolism.

Other forms of treatment include chemical cardioversion to normal sinus rhythm, electrical cardioversion, and RF catheter ablation of selected areas determined by mapping. In the more recent past, other surgical procedures have been developed for atrial fibrillation, including left atrial isolation, transvenous catheter or cryosurgical ablation of His bundle, and the Corridor procedure, which have effectively eliminated irregular ventricular rhythm. However, these procedures have for the most part failed to restore normal cardiac hemodynamics, or alleviate the patient's vulnerability to thromboembolism because the atria are allowed to continue to fibrillate.

Accordingly, a more effective surgical treatment was required to cure medically refractory atrial fibrillation of the heart.

On the basis of electrophysiologic mapping of the atria and identification of macroreentrant circuits, a surgical approach was developed which effectively creates an electrical maze in the atrium (i.e., the MAZE procedure) and precludes the ability of the atria to fibrillate. Briefly, in the procedure commonly referred to as the MAZE m procedure, strategic atrial incisions are performed to prevent atrial reentry and allow sinus impulses to activate the entire atrial myocardium, thereby preserving atrial transport function postoperatively. Since atrial fibrillation is characterized by the presence of multiple macroreentrant circuits that are fleeting in nature and can occur anywhere in the atria, it is prudent to interrupt all of the potential pathways for atrial macroreentrant circuits. These circuits, incidentally, have been identified by intraoperative mapping both experimentally and clinically in patients.

Generally, this procedure includes the excision of both atrial appendages, and the electrical isolation of the pulmonary veins. Further, strategically placed atrial incisions not only interrupt the conduction routes of the most common reentrant circuits, but they also direct the sinus impulse from the sinoatrial node to the atrioventricular node along a specified route. In essence, the entire atrial myocardium, with the exception of the atrial appendages and the pulmonary veins, is electrically activated by providing for multiple blind alleys off the main conduction route between the sinoatrial node to the atrioventricular node. Atrial transport function is thus preserved postoperatively, as generally set forth in the series of articles: Cox, Schuessler, Boineau, Canavan, Cain, Lindsay, Stone, Smith, Corr, Chang, and D'Agostino, Jr., The Surgical Treatment of Atrial Fibrillation (pts. 1-4), 101 THORAC CARDIOVASC SURG., 402-426, 569-592 (1991).

While this MAZE III procedure has proven effective in ablating medically refractory atrial fibrillation and associated detrimental sequelae, this operational procedure is traumatic to the patient since substantial incisions are introduced into the interior chambers of the heart. Moreover, using current techniques, many of these procedures require a gross thoracotomy, usually in the form of a median sternotomy, to gain access into the patient's thoracic cavity. A saw or other cutting instrument is used to cut the sternum longitudinally, allowing two opposing halves of the anterior or ventral portion of the rib cage to be spread apart. A large opening into the thoracic cavity is thus created, through which the surgical team may directly visualize and operate upon the heart for the MAZE III procedure. Such a large opening further enables manipulation of surgical instruments and/or removal of excised heart tissue since the surgeon can position his or her hands within the thoracic cavity in close proximity to the exterior of the heart. The patient is then placed on cardiopulmonary bypass to maintain peripheral circulation of oxygenated blood.

Not only is the MAZE III procedure itself traumatic to the patient, but the postoperative pain and extensive recovery time due to the conventional thoracotomy substantially increase trauma and further extend hospital stays. Moreover, such invasive, open-chest procedures significantly increase the risk of complications and the pain associated with sternal incisions. While heart surgery produces beneficial results for many patients, numerous others who might benefit from such surgery are unable or unwilling to undergo the trauma and risks of current techniques.

BRIEF SUMMARY OF THE INVENTION

Accordingly, it is an object of the present invention to provide a surgical procedure and system for closed-chest, closed heart ablation of heart tissue.

It is another object of the present invention to provide a surgical procedure and system for ablating medically refractory atrial fibrillation.

Yet another object of the present invention is to provide a surgical procedure and surgical devices which are capable of strategically ablating heart tissue from the interior chambers or external cardiac surfaces thereof without substantially disturbing the structural integrity of the atria.

Still another object of the present invention is to enable surgeons to ablate medically refractory atrial fibrillation while the heart is still beating.

In accordance with the foregoing objects of the invention, the present invention provides surgical systems and methods for ablating heart tissue within the interior and/or exterior of the heart. This procedure is particularly suitable for surgeries such as the MAZE III procedure developed to treat medically refractory atrial fibrillation since the need for substantial, elongated, transmural incisions of the heart walls are eliminated. Moreover, this technique is preferably performed without having to open the chest cavity via a median sternotomy or major thoracotomy. The system is configured for being introduced through a small intercostal, percutaneous penetration into a body cavity and engaging the heart wall through purse-string incisions. As a result, the procedure of the present invention reduces potential postoperative complications, recovery time and hospital stays.

A system for transmurally ablating heart tissue is provided including an ablating probe having an elongated shaft positionable through the chest wall and into a transmural penetration extending through a muscular wall of the heart and into a chamber thereof. The shaft includes an elongated ablating surface for ablating heart tissue. The system of the present invention further includes a sealing device fixable to the heart tissue around the transmural penetration for forming a hemostatic seal around the probe to inhibit blood loss therethrough.

A preferred method and device for ablating the heart tissue is with a cryosurgical ablation device. Although cryosurgical ablation is a preferred method, a number of other ablation methods could be used instead of cryoablation. Among these tissue ablation means are Radio Frequency (RF), ultrasound, microwave, laser, heat, localized delivery of chemical or biological agents and light-activated agents to name a few.

More specifically, the system of the present invention enables the formation of a series of strategically positioned and shaped elongated, transmural lesions which cooperate with one another to reconstruct a main electrical conduction route between the sinoatrial node to the atrioventricular node. Atrial transport function is thus preserved postoperatively for the treatment of atrial fibrillation.

The system includes a plurality of surgical probes each having an elongated shaft. Each shaft includes an elongated ablating surface of a predetermined shape for contact with at least one specific surface of the heart and specifically the interior walls of atria chamber. Such contact with the ablating surface for a sufficient period of time causes transmural ablation of the wall. Collectively, a series of strategically positioned and shaped elongated, transmural lesions are formed which cooperate with one another to treat atrial fibrillation. Each transmural penetration includes a purse-string suture formed in the heart tissue around the respective transmural penetration in a manner forming a hemostatic seal between the respective probe and the respective transmural penetration to inhibit blood loss therethrough.

When using a cryosurgical probe, the probe includes a shaft having a delivery passageway for delivery of pressurized cryogen therethrough and an exhaust passageway for exhaust of expended cryogen. The pressurized cryogen is expanded in a boiler chamber thereby cooling the elongated ablating surface for cryogenic cooling of the elongated ablating surface. The elongated shaft is configured to pass through the chest wall and through a penetration in the patient's heart for ablative contact with a selected portion of the heart.

In another aspect of the present invention, a surgical method for ablating heart tissue from the interior and/or exterior walls of the heart is provided including the steps of forming a penetration through a muscular wall of the heart into an interior chamber thereof and positioning an elongated ablating device having an elongated ablating surface through the penetration. The method further includes the steps of forming a hemostatic seal between the device and the heart wall penetration to inhibit blood loss through the penetration and contacting the elongated ablating surface of the ablating device with a first selected portion of an interior and/or exterior surface of the muscular wall for ablation thereof.

More preferably, a method for ablating medically refractory atrial fibrillation of the heart is provided comprising the steps of forming a penetration through the heart and into a chamber thereof positioning an elongated ablating devices having an elongated ablating surface through the penetration and forming a hemostatic seal between the ablating device and the penetration to inhibit blood loss therethrough. The present invention method further includes the steps of strategically contacting the elongated ablating surface of the ablating device with a portion of the muscular wall for transmural ablation thereof to form at least one elongated transmural lesion and repeating these steps for each remaining lesion. Each transmural lesion is formed through contact with the ablating surface of one of the plurality of ablating device and the strategically positioned elongated transmural lesions cooperate to guide the electrical pulse pathway along a predetermined path for the surgical treatment of atrial fibrillation.

The entire procedure is preferably performed through a series of only five purse-strings sutures strategically located in the right and left atria, and pulmonary vein portions. Generally, multiple lesions can be formed through a single purse-string either through the use of assorted uniquely shaped ablating devices or through the manipulation of a single ablating device.

It should be understood that while the invention is described in the context of thoracoscopic surgery on the heart, the systems and methods disclosed herein are equally useful to ablate other types of tissue structures and in other types of surgery such as laparoscopy and pelviscopy.

The procedure and system of the present invention have other objects of advantages which will be readily apparent from the following description of the preferred embodiments.

BRIEF DESCRIPTION OF THE DRAWINGS

FIG. 1 is an upper left, posterior perspective view of a human heart incorporating the system and procedure for treatment of medically refractory atrial fibrillation constructed in accordance with the principles of the present invention.

FIG. 2 is a right, antero-lateral perspective view of the human heart incorporating the present invention system and procedure thereof.

FIGS. 3A and 3B are schematic diagrams of the atria portion of the heart illustrating the pattern of transmural cryolesions to create a predetermined conduction path in the atrium using the system and procedure of the present invention.

FIG. 4 is a top plan view of a set of cryoprobe devices constructed in accordance with the present invention, and utilized in the system and procedure of the present invention.

FIG. 5 is a top perspective view of a patient showing use of the system and procedure on the patient.

FIG. 6 is an enlarged, fragmentary, top plan view, in cross-section, of one of the cryoprobes in the set of cryoprobes of FIG. 4, illustrating the expansion chamber thereof.

FIGS. 6A-6D illustrate use of a slidable insulative tube for insulating portions of the probe.

FIG. 7 is a front elevation view, in cross-section, of the ablating end of a cryoprobe, taken substantially along the plane of the line 7-7 in FIG. 6.

FIG. 8 is a front elevation view, in cross-section, of an alternative embodiment of the ablating end of FIG. 7.

FIG. 9 is a transverse cross-sectional view of the system and patient, taken through the patient's thorax generally along the plane of the line 9-9 in FIG. 11A, showing the relative positioning of the right and left intercostal percutaneous penetrations.

FIG. 10 is a front schematic view of a patient's cardiovascular system illustrating the positioning of a cardiopulmonary bypass system for arresting the heart and establishing cardiopulmonary bypass in accordance with the principles of the present invention.

FIGS. 11A-11D is a series of top plan views of the patient undergoing a pericardiotomy as well as the installation of a purse-string suture and a stay suture to assist in suspending the pericardium.

FIGS. 12A-12C is a series of enlarged, fragmentary side elevation views looking into the patient's thoracic cavity at the right atrium through a soft tissue retractor (not shown) in the system of FIG. 5, and illustrating the introduction of cryoprobes constructed in accordance with the present invention through purse-strings for the formation of a posterior longitudinal right atrial cryolesion and a tricuspid valve annulus cryolesion.

FIG. 13 is an enlarged, fragmentary, transverse cross-sectional view, partially broken away, of the system and patient's heart of FIG. 5, and illustrating the introduction of a tricuspid valve cryoprobe through a purse-string suture in the right atrial freewall to form the elongated, transmural, tricuspid valve annulus cryolesion.

FIG. 14 is a side elevation view peering at the right atrial appendage through the soft tissue retractor passageway (not shown) in the system of FIG. 5, showing the formation of a perpendicular right atrial cryolesion.

FIG. 15 is a fragmentary, transverse cross-sectional view of the system and patient's heart, illustrating the formation of a right atrial anteromedial counter cryolesion.

FIG. 16 is an upper left, posterior perspective view the human heart of FIG. 1, illustrating the location of the purse-string sutures in the right and left atrial walls, to access opposite sides of the atrial septum wall for the introduction of an atrial septum clamping cryoprobe.

FIG. 17 is a fragmentary, transverse cross-sectional view, partially broken away, of the system and patient's heart, showing the atrial septum clamping cryoprobe engaged with the atrial septum wall for the formation of an anterior limbus of the fossa ovalis cryolesion.

FIGS. 18A and 18B is a sequence of enlarged, fragmentary, transverse cross-sectional views, partially broken away, of the system and patient's heart, illustrating the technique employed to enable insertion of the distal ends of the atrial septum clamping cryoprobe through the adjacent purse-string sutures.

FIGS. 19A-19D is a series of fragmentary, transverse cross-sectional views, partially broken away, of the system and patient's heart, showing the formation of an endocardial pulmonary vein isolation cryolesion using a four-step process.

FIGS. 20A and 20B is a sequence of fragmentary, transverse cross-sectional views, partially broken away, of the system and patient's heart, showing the formation of the pulmonary vein isolation cryolesion through an alternative two-step process.

FIG. 21 is an upper left, posterior perspective view of the human heart illustrating the formation of an additional epicardial pulmonary vein isolation cryolesion.

FIG. 22 is a fragmentary, transverse cross-sectional view of the system and patient's heart, showing the formation of a left atrial anteromedial cryolesion.

FIG. 23 is a fragmentary, transverse cross-sectional view of the system and patient's heart, illustrating the formation of a posterior vertical left atrial cryolesion.

FIG. 24 is a top plan view of the right angle cryoprobe of FIGS. 12A and 12B.

FIG. 25 is a top plan view of the tricuspid valve annulus cryoprobe of FIG. 13.

FIG. 26 is a top plan view of an alternative embodiment of the tricuspid valve annulus cryoprobe of FIG. 25.

FIG. 27 is a top plan view of the right atrium counter lesion cryoprobe of FIG. 15.

FIG. 28 is a top plan view of the atrial septum clamping cryoprobe of FIGS. 17 and 18.

FIG. 29 is an enlarged front elevation view, in cross-section, of a coupling device of the septum clamping cryoprobe, taken substantially along the plane of the line 29-29 in FIG. 28.

FIG. 30 is an enlarged rear elevation view, in cross-section, of an aligning device of the septum clamping cryoprobe, taken substantially along the plane of the line 30-30 in FIG. 28.

FIG. 31 is an enlarged, fragmentary, top plan view of an alternative embodiment to the atrial septum clamping cryoprobe of FIG. 28.

FIG. 32 is a top plan view of an all-purpose cryoprobe of FIGS. 19A and 19B.

FIG. 33 is a top plan view of the pulmonary vein loop cryoprobe of FIGS. 20 and 21.

FIG. 34 is a top plan view of the left atrial anteromedical cryoprobe of FIG. 22.

FIG. 35 is a top plan view of an alternative embodiment of the all-purpose cryoprobe of FIG. 23.

FIG. 36 is an enlarged, fragmentary, top plan view of an alternative embodiment to the cryoprobes formed for contact of the ablation surface with the epicardial surface of the heart.

FIG. 37 is an exploded view of a cryogen delivery tube.

FIG. 38 is a partial cross-sectional view of the probe having the delivery tube of FIG. 37.

FIG. 39 is an exploded view of the outer tube of the probe of FIG. 38.

FIG. 40 is an end view of the ablating surface of the probe of FIG. 39.

FIG. 41 shows a probe having a delivery tube with adjustable holes wherein an outer tube is slidably movable relative to an inner tube.

FIG. 42 shows the probe of FIG. 41 with the outer tube moved distally relative to the inner tube.

FIG. 43 shows a probe having vacuum ports for adhering the probe to the tissue to be ablated.

FIG. 44 is a cross-sectional view of the probe of FIG. 43 along line I-I.

FIG. 45 shows a probe having a malleable shaft.

FIG. 46 shows the tip of the probe of FIG. 45.

FIG. 47 is a cross-sectional view of the probe of FIG. 45 along line II-II.

DETAILED DESCRIPTION OF THE INVENTION

Attention is now directed to FIGS. 1-3 where a human heart H is illustrated incorporating a series of strategically positioned transmural lesions throughout the right atrium RA and the left atrium LA formed with the heart treatment procedure and system of the present invention. FIG. 1 represents the desired pattern of lesions created on the right atrium RA, including the posterior longitudinal right atrial lesion 50, the tricuspid valve annulus lesion valve annulus lesion 51, the pulmonary vein isolation lesion vein isolation lesion 52 and the perpendicular lesion 53; while FIG. 2 represents a right, anterior perspective view of the heart H illustrating right atrium RA including a right atrial anteromedial counter lesion 55. The cumulative pattern of lesions reconstruct a main electrical conduction route between the sinoatrial node to the atrioventricular node to postoperatively preserve atrial transport function. Unlike prior surgical treatments, the system and procedure of the present invention, generally designated 56 in FIGS. 4 and 5, employ a closed-heart technique which eliminates the need for gross multiple elongated incisions of the atria to ablate heart tissue in the manner sufficient to preclude electrical conduction of reentrant pathways in the atria.

In accordance with the heart treatment procedure and system of the present invention, a set of uniquely-shaped, elongated tip ablation probes 57 (FIG. 4, to be discussed in detail below) are employed which are formed and dimensioned for insertion through at least one of a plurality of heart wall penetrations, preferably sealed by means of purse-string sutures 58, 60, 61, 62 and 63, strategically positioned about the atria of the heart H. Once the distal end of the probe is inserted through the desired purse-string suture, an elongated ablating surface 65 thereof is maneuvered into contact with the selected endocardial surface of an interior wall of the atria to create an elongated, transmural lesion. As shown in FIGS. 3A and 3B, these individual lesions collectively form a pattern of transmurally ablated heart tissue to surgically treat medically refractory atrial fibrillation.

Briefly, FIG. 4 represents a collection or set of probes 57 constructed in accordance with the present invention which are employed to preclude electrical conduction of reentrant pathways in the atria using closed-heart surgical techniques. Collectively, as will be apparent, the probes enable the surgical formation of a series of lesions which are illustrated in FIGS. 3A and 3B. Each probe (FIGS. 24-28 and 32-35) includes an elongated shaft 66 formed to extend through an access port or passageway 67 in a retractor 68 (FIG. 5) which is mounted in a percutaneous intercostal penetration. The terms "percutaneous intercostal penetration" and "intercostal penetration" as used herein refer to a penetration, in the form or a cut, incision, hole, retractor, cannula, trocar sleeve, or the like, through the chest wall between two adjacent ribs wherein the patient's rib cage and sternum remain generally intact. These terms are intended to distinguish a gross thoracotomy, such as a median sternotomy, wherein the sternum and/or one or more ribs are cut or removed from the rib cage. It should be understood that one or more ribs may be retracted to widen the intercostal space between adjacent ribs without departing from the scope of the invention.

Proximate the distal end of each probe is an elongated ablating end 70 having an ablating surface 65 formed to transmurally ablate heart tissue. Access to the selected portions of the atria of the heart H are provided by the specially shaped shafts 66 and ablating ends 70 which are configured to position the elongated ablating surface 65 through the chest wall of patient P and through a strategically positioned penetration in the muscular wall of the patient's heart H for ablative contact with a selected portion of an interior surface of the muscular wall. Subsequent contact of the ablating surface 65 with specific selected wall portions of the atria enable selected, localized transmural ablation thereof.

In a preferred embodiment the probes 57 form the lesions by freezing the heart tissue. Although freezing is a preferred method of ablating tissue, the probe 57 may use any other method such as RF ablation, ultrasound, microwave, laser, localized delivery of chemical or biological agents, light-activated agents, laser ablation or resistance heating ablation. Regarding the localized delivery of chemical or biological agents, the device may include an injection device capable of injecting the chemical or biological agent onto or into the desired tissue for localized ablation thereof. The source of the chemical or biological agent may be stored in a reservoir contained in the probe or be stored in an external reservoir coupled to the injecting end of the probe.

When the probe freezes tissue during ablation, an opposite end of the probe has a fitting 71 formed for releasable coupling to an end of a delivery hose which in turn is coupled to a source (both of which are not shown) of cryogenic media. A threaded portion 72 of the fitting is formed for removable mounting to the delivery hose and further provides communication with the cryogenic media for both delivery to and exhaust from the probe.

As shown in FIG. 6, each probe includes an elongated shaft 66 sufficiently dimensioned and shaped to enable manual manipulation of the ablating end 70 into contact with the desired heart tissue from outside the thoracic cavity. The shaft 66 is preferably tubular-shaped and defines a communication passageway 73 extending therethrough which provides both delivery and exhaust of the cryogen to and from the ablating end 70. Communication passageway 73 extends fully from the fitting 71 (FIG. 4) to a closed-end boiler chamber 75 where the cryogen exits the ablating end 70. Preferably, the tubular shaft 66 includes an outer diameter in the range of about 2.0 mm to about 5.0 mm, and most preferably about 4.0 mm; while the inner diameter is in the range of about 1.5 mm to about 4.5 mm, and most preferably about 3.0 mm.

Concentrically positioned in the communication passageway 73 of each probe is a delivery tube 76 (FIG. 6) which extends from the fitting 71 to proximate the boiler chamber 75 for communication therebetween enabling delivery and dispersion of the cryogen to the boiler chamber. The proximal end of delivery tube 76 is coupled to the cryogen liquid source through a conventional fitting for delivery of the cryogen through a delivery passageway 77. The outer diameter of delivery tube 76 is dimensioned such that an annular exhaust passageway 78 is formed between the outer diameter of the delivery tube 76 and the inner diameter of the tubular shaft 66. This exhaust passageway 78 provides a port through which the expended cryogen exiting the boiler chamber can be exhausted. Preferably, the delivery tube 76 includes an outer diameter in the range of about 1.4 mm to about 3.0 mm, and most preferably about 2.0 mm; while the inner diameter is in the range of about 1.15 mm to about 2.75 mm, and most preferably about 1.50 mm.

The shaft of each probe 56 is specifically formed and shaped to facilitate performance of one or more of the particular procedures to be described in greater detail below. However, due to the nature of the procedure and the slight anatomical differences between patients, each probe may not always accommodate a particular patient for the designated procedure. Accordingly, it is highly advantageous and desirable to provide an exhaust shaft 66 and delivery tube 76 combination which is malleable. This material property permits reshaping and bending of the exhaust shaft and delivery tube as a unit to reposition the ablating surface for greater ablation precision. Moreover, the shaft must be capable of bending and reshaping without kinking or collapsing. Such properties are especially imperative for the devices employed in the pulmonary vein isolation lesion formation which are particularly difficult to access.

This malleable material, for example, may be provided by certain stainless steels, NiTi or a shape memory alloy in its superelastic state such as a superelastic alloy. Moreover, the shaft portion, with the exception of the ablating surface, may be composed of a polymer material such as plastic which of course exhibits favorable thermoplastic deformation characteristics. Preferably, however, the exhaust and delivery shafts 66 and 76 are composed of bright annealed 304 stainless steel. The delivery tube 76 may also be composed of NiTi or other superelastic alloy.

To prevent or substantially reduce contact between the concentric tubes during operation, due to resonance or the like, the delivery tube 76 may be isolated and separated from contact with the inner walls of the exhaust shaft 66 by placing spacers around the delivery tube. These spacers may be provided by plastic or other polymer material. Alternatively, the delivery tube may be brazed or welded to one side of the inner wall of the exhaust shaft 66 along the longitudinal length thereof to resist vibrational contact, as illustrated in FIG. 8.

In accordance with the present invention, the lesions formed by this system and procedure are generally elongated in nature. The ablating end 70 is thus provided by an elongated ablating surface 65 which extends rearwardly from the distal end a distance of at least about seven (7) times to about thirty (30) times the outer diameter of the ablating end, which incidentally is about the same as the outer diameter of the shaft 66. Hence, the length of the ablating surface is at least three (3) cm long, more preferably at least four (4) cm long, and most preferably at least five (5) cm long. Alternatively, the ablating surface 65 has a length of between about three (3) cm to about eight (8) cm.

In most applications, uniform cryothermic cooling along the full length of the ablating surface is imperative for effective operation. This task, alone, may be difficult to accomplish due primarily to the relatively small internal dimensions of the probe, as well as the generally curved nature of the boiler chambers in most of the cryoprobes (FIG. 4). FIG. 6 represents a typical cross-sectional view of an ablating end 70 of one of the probe devices of the present invention in which the ablating surface 65 is formed to contact the heart tissue for localized, transmural ablation thereof. Ablating end 70 therefore is preferably provided by a material exhibiting high thermal conductivity properties suitable for efficient heat transfer during cryogenic cooling of the tip. Such materials preferably include silver, gold and oxygen free copper or the like.

The ablating end 70 is preferably provided by a closed-end, elongated tube having an interior wall 80 which defines the boiler chamber 75, and is about 1.0 mm to about 1.5 mm thick, and most preferably about 1.25 mm thick. This portion is specifically shaped for use in one or more ablation procedures and is formed for penetration through the muscular walls of the heart. The distal end of exhaust shaft 66 is preferably inserted through an opening 81 into the boiler chamber 75 such that the exterior surface 82 at the tip of the exhaust shaft 66 seatably abuts against the interior wall 80 of the ablating end 70 for mounting engagement therebetween. Preferably, silver solder or the like may be applied to fixably mount the ablating end to the end of the exhaust shaft. Alternatively, the proximal end of ablating end 70 can be mounted directly to the distal end of exhaust shaft 66 (i.e., in an end-to-end manner) using electron-beam welding techniques. In either mounting technique, a hermetic seal must be formed to eliminate cryogen leakage.

Proximate the distal end of delivery tube 76 is a delivery portion 83 which extends through the opening 81 and into boiler chamber 75 of the ablating end 70. This closed-end delivery portion includes a plurality of relatively small diameter apertures 85 which extend through the delivery portion 83 into delivery passageway 77 to communicate the pressurized cryogen between the delivery passageway and the boiler chamber 75. Using the Joule-Thompson effect, the cryogen flows through the delivery passageway in the direction of arrow 86 and into the delivery portion 83 where the cryogen expands through the apertures from about 600-900 psi to about 50-200 psi in the boiler chamber. As the cryogen expands, it impinges upon the interior wall 80 of the ablating end cooling the ablating surface 65. Subsequently, the expended cryogen flows in the direction of arrow 87 passing through the exhaust passageway 78 and out through the delivery hose.

The number of apertures required to uniformly cool the ablating end is primarily dependent upon the length of the boiler chamber 75, the diameter of the apertures, the type of cryogen employed and the pressure of the cryogen. Generally, for the preferred cryogen of nitrous oxide ($N_2O$), these delivery apertures 85 are equally spaced-apart at about 5 mm to about 12 mm intervals, and extend from the proximal end of the boiler chamber to the distal end thereof. The preferred diameters of the apertures 85 range from about 0.004 inch to about 0.010 inch. These diameters may vary of course.

For most probes, three to four apertures or sets of apertures spaced-apart longitudinally along delivery end portion are sufficient. Only one aperture 85 may be required at each longitudinal spaced location along the delivery portion 83 (FIG. 8). This one aperture may be strategically positioned radially about the delivery portion to direct the stream of cryogen onto the portion of the interior wall 80 directly beneath or near the predetermined portion of the ablating surface 65 which is to contact the heart wall tissue for a particular procedure. Hence, the spaced-apart apertures may be strategically positioned to collectively direct the cryogen onto particular surfaces of the ablating end to assure maximum cooling of those portions. In some instances, however (as shown in FIG. 7), more than one aperture 85 may be radially positioned about the delivery portion 83 at any one longitudinal spaced location, proximate a plane extending transversely therethrough, for additional cryogenic cooling of the ablating surface. This may be especially important where the probe is to be employed in more than one procedure.

Due to the elongated and curved nature of the ablating surface 65, it is difficult to maintain a generally uniform temperature gradient along the desired portions of the ablating surface during cryogenic cooling. This may be due in part to the pressure decrease in the delivery passageway 77 of the delivery portion 83 as the cryogen passes therethrough. To compensate for this pressure loss as the cryogen passes through the delivery portion, the diameters of the apertures 85, 85', 85" etc., may be slightly increased from the proximal end of the delivery portion 83 to the distal end thereof. Thus, as the cryogen travels through the delivery portion 83 of the delivery tube, a more uniform volume of cryogen may be distributed throughout the boiler chamber 75 even though the cryogenic pressure incrementally decreases from the proximal end of the delivery portion 83.

Moreover, the delivery volume of the cryogenic cooling also may be controlled by varying the number of apertures at particular portions of the ablating end i.e., increasing or decreasing the number of apertures at a particular location. This directed cooling will have a localized cooling effect, and is exemplified in the ablating end 70 of FIG. 4. In this embodiment, the increased number of apertures along the inner bight portion 88 of delivery portion 83 delivers a more direct and greater volume of cryogen against the inner bight portion 88, as compared to the outer bight portion 90.

An insulative coating or tubing 89 is preferably included extending circumferentially around portions of the cryoprobe shaft 66 near the ablation end 70. This insulative tubing provides an insulatory barrier around shaft 66 to prevent inadvertent direct contact between the shaft, which will be cooled by the expended cryogen flowing through the exhaust passageway 75, and any organs or tissue of the percutaneous penetration. The insulative tubing is preferably spaced from the shaft 66 to define an air gap between the inner surface of the tubing and the outer surface of the shaft.

The insulative tubing 89 preferably extends around the elongated shaft 66 from the base of the ablation end 70 to the fitting 71. In some instances, however, the tubing may only need to extend from the base of the ablation end to a midportion of the elongated shaft. The insulative tubing 89 is preferably provided by heat shrink polyolefin tubing, silicone, TEFLON®, or the like.

In the preferred form, as shown in FIG. 7, the transverse, cross-sectional dimension of the ablating end 70 is circular-shaped having a substantially uniform thickness. However, it will be understood that the ablating surface 65 may include a generally flat contact surface 91 formed for increased area contact with the heart tissue without requiring a substantial increase in the diameter of the ablating surface. As best viewed in FIGS. 8A-8C, contact surface 91 may be generally flat or have a much larger radius than that of the ablating end. Moreover, the spaced-apart apertures 85 are preferably oriented and formed to deliver the cryogen into direct impingement with the underside of the contact surface 91 of ablating end 70. In this arrangement, the delivery portion 83 of the delivery tube 76 may be mounted to one side of the interior wall 80, as set forth above.

Alternatively, the contact surface can be provided by a blunted edge or the like to create a relatively narrow lesion. Although not illustrated, the transverse cross-sectional dimension of this embodiment would appear teardrop-shaped.

FIGS. 6A-6D illustrate an embodiment of the probe 57 in which an insulative jacket or sleeve 304 is disposed on the probe so as to be movable relative thereto. The sleeve 304 has a window or cut-out portion 305 which exposes a selected area of the probe 57. FIG. 6A shows the sleeve 304 located around the probe shaft, while FIG. 6B shows the sleeve after it has been slid over part of the probe ablating surface 65. FIG. 6C shows the sleeve 304 after it has been slid completely over the ablating surface 65 to a position where the window 305 exposes one area of the surface 65 for ablating tissue. FIG. 6D shows the sleeve 304 rotated to a different position where the window 305 exposes a different area of the surface 65 for ablating tissue. The sleeve 304 may be slidable and rotatable relative to the probe as show in FIGS. 6A-6D. Alternatively, the sleeve 304 may be fixed axially with respect to the probe 57 but rotatable relative thereto so that the window is able to expose different areas of the ablating surface. Further still, the sleeve 304 may be fixed on the probe 57 such that only a selected area of ablation surface 65 is exposed through window 305. The sleeve 304 may be formed of any suitable material, for example, a flexible polymer having low thermal conductivity.

The preferred cryogen employed in the devices of the present invention is nitrous oxide ($N_2O$) which is normally stored in a compressed gas cylinder (not shown). Other cryogenic fluids may be employed which include liquid nitrogen or liquefied air stored in a Dewar vessel (not shown), Freon 13, Freon 14, Freon 22, and normally gaseous hydrocarbons.

To cool the ablating end of the cryoprobe, cryogen is selectively delivered through the delivery passageway 77 of delivery tube 76 into the delivery conduit thereof. As the cryogen flows through delivery apertures 85, the gas expands into the boiler chamber 75, cooling the ablating surface using the well known Joule-Thompson effect. The elongated ablating surface 65 is then immediately cooled to a temperature of preferably between about −50.degree. C. to about −80.degree. C., when nitrous oxide is employed. Direct conductive contact of the cooled, elongated ablating surface 65 with the selected heart tissue causes cryogenic ablation thereof. Subsequently, a localized, elongated, transmural lesion is formed at a controlled location which sufficiently prevents or is resistant to electrical conduction therethrough.

To assure preclusion of electrical conduction of reentrant pathways in the atria, the lesions must be transmural in nature. Hence, the minimum length of time for conductive contact of the ablating surface with the selected heart tissue necessary to cause localized, transmural ablation thereof is to a large degree a function of the thickness of the heart wall tissue, the heat transfer loss due do the convective and conductive properties of the blood in fluid contact with the ablating surface, as well as the type of cryogen employed and the rate of flow thereof. In most instances, when employing nitrous oxide as the cryogen, tissue contact is preferably in the range of about 2-4 minutes.

As mentioned, while the closed-heart surgical system and procedure of the present invention may be performed through open-chest surgery, the preferred technique is conducted through closed-chest methods. FIGS. 5 and 9 illustrate system 56 for closed-chest, closed-heart surgery positioned in a patient P on an operating table T. The patient is prepared for cardiac surgery in the conventional manner, and general anesthesia is induced. To surgically access the right atrium, the patient is positioned on the patient's left side so that the right lateral side of the chest is disposed upward. Preferably, a wedge or block W having a top surface angled at approximately 20.degree. to 45.degree. is positioned under the right side of the patient's body so that the right side of the patient's body is somewhat higher than the left side. It will be understood, however, that a similar wedge or block W is positioned under the left side of patient P (not shown) when performing the surgical procedure on the left atrium In either position, the patient's right arm A or left arm (not shown) is allowed to rotate downward to rest on table T, exposing either the right lateral side or the left lateral side of the patient's chest.

Initially one small incision 2-3 cm in length is made between the ribs on the right side of the patient P, usually in the third, fourth, or fifth intercostal spaces, and most preferably the fourth as shown in FIG. 11A. When additional maneuvering space is necessary, the intercostal space between the ribs may be widened by spreading of the adjacent ribs. A thoracoscopic access device 68 (e.g. a retractor, trocar sleeve or cannulae), providing an access port 67, is then positioned in the incision to retract away adjacent tissue and protect it from trauma as instruments are introduced into the chest cavity. This access device 68 has an outer diameter preferably less than 14 mm and an axial passage of a length less than about 12 mm. It will be understood to those of ordinary skill in the art that additional thoracoscopic trocars or the like may be positioned within intercostal spaces in the right lateral chest inferior and superior to the retractor 68, as well as in the right anterior (or ventral) portion of the chest if necessary. In other instances, instruments may be introduced directly through small, percutaneous intercostal incisions in the chest.

Referring again to FIGS. 5 and 9, the retractor 68, such as that described in detail in commonly assigned U.S. patent application Ser. No. 08/610,619 filed Mar. 4, 1996, surgical access to the body cavity of patient P through the first intercostal percutaneous penetration 92 in the tissue 93. Briefly, retractor 68 includes an anchoring frame 95 having a passageway 67 therethrough which defines a longitudinal retractor axis. The anchoring frame 95 is positionable through the intercostal percutaneous penetration 92 into the body cavity. A flexible tensioning member 96 is attached to anchoring frame 95 and extendible from the anchoring frame out of the body through intercostal penetration 92 to deform into a non-circular shape when introduced between two ribs. The tensioning member 96 is selectively tensionable to spread the tissue radially outward from the longitudinal axis. Hence, it is the tension imposed on the flexible tensioning member 96 which effects retraction of the tissue, rather than relying on the structural integrity of a tubular structure such as a trocar sheath.

Once the retractor 68 has been positioned and anchored in the patient's chest, visualization within the thoracic cavity may be accomplished in any of several ways. An endoscope 97 (FIG. 5) of conventional construction is positioned through a percutaneous intercostal penetration into the patient's chest, usually through the port of the soft tissue retractor 68. A video camera 98 is mounted to the proximal end of endoscope 97, and is connected to a video monitor 100 for viewing the interior of the thoracic cavity. Endoscope 97 is manipulated so as to provide a view of the right side of the heart, and particularly, a right side view of the right atrium. Usually, an endoscope of the type having an articulated distal end such as the Distalcam 360, available from Welch-Allyn of Skameateles Falls, N.Y., or a endoscope having a distal end disposed at an angle between 30.sub.i and 90.sub.i will be used, which is commercially available from, for example, Olympus Corp., Medical Instruments Division, Lake Success, N.Y. A light source (not shown) is also provided on endoscope 97 to illuminate the thoracic cavity.

Further, the surgeon may simply view the chest cavity directly through the access port 67 of the retractor 68. Moreover, during the closed heart procedure of the present invention, it may be desirable to visualize the interior of the heart chambers. In these instances a transesophageal echocardiography may be used, wherein an ultrasonic probe is placed in the patient's esophagus or stomach to ultrasonically image the interior of the heart. A thoracoscopic ultrasonic probe may also be placed through access device 68 into the chest cavity and adjacent the exterior of the heart for ultrasonically imaging the interior of the heart.

An endoscope may also be employed having an optically transparent bulb such as an inflatable balloon or transparent plastic lens over its distal end which is then introduced into the heart. As disclosed in commonly assigned, co-pending U.S. patent application Ser. No. 08/425,179, filed Apr. 20, 1995, the balloon may be inflated with a transparent inflation fluid such as saline to displace blood away from distal end and may be positioned against a site such a lesion, allowing the location, shape, and size of cryolesion to be visualized.

As a further visualization alternative, an endoscope may be utilized which employs a specialized light filter, so that only those wavelengths of light not absorbed by blood are transmitted into the heart. The endoscope utilizes a CCD chip designed to receive and react to such light wavelengths and transmit the image received to a video monitor. In this way, the endoscope can be positioned in the heart through access port 67 and used to see through blood to observe a region of the heart. A visualization system based on such principles is described in U.S. Pat. No. 4,786,155, which is incorporated herein by reference.

Finally, the heart treatment procedure and system of the present invention may be performed while the heart remains beating. Hence, the trauma and risks associated with cardiopulmonary bypass (CPB) and cardioplegic arrest can be avoided. In other instances, however, arresting the heart may be advantageous. Should it be desirable to place the patient on cardiopulmonary bypass, the patient's right lung is collapsed and the patient's heart is arrested. Suitable techniques for arresting cardiac function and establishing CPB without a thoracotomy are described in commonly-assigned, co-pending U.S. patent application Ser. No. 08/282,192, filed Jul. 28, 1994 and U.S. patent application Ser. No. 08/372,741, filed Jan. 17, 1995, all of which are incorporated herein by reference. Although it is preferred to use the endovascular systems described above, any system for arresting a patient's heart and placing the patient on CPB may be employed.

As illustrated in FIG. 10, CPB is established by introducing a venous cannula 101 into a femoral vein 102 in patient P to withdraw deoxygenated blood therefrom. Venous cannula 101 is connected to a cardiopulmonary bypass system 104 which receives the withdrawn blood, oxygenates the blood, and returns the oxygenated blood to an arterial return cannula 105 positioned in a femoral artery 106.

A pulmonary venting catheter 107 may also be utilized to withdraw blood from the pulmonary trunk 108. Pulmonary venting catheter 107 may be introduced from the neck through the interior jugular vein 110 and superior vena cava 111, or from the groin through femoral vein 102 and inferior vena cava 103. An alternative method of venting blood from pulmonary trunk 108 is described in U.S. Pat. No. 4,889,137, which is incorporated herein by reference. In the technique described therein, an endovascular device is positioned from the interior jugular vein in the neck through the right atrium, right ventricle, and pulmonary valve into the pulmonary artery so as to hold open the tricuspid and pulmonary valves.

For purposes of arresting cardiac function, an aortic occlusion catheter 113 is positioned in a femoral artery 106 by a percutaneous technique such as the Seldinger technique, or through a surgical cut-down. The aortic occlusion catheter 113 is advanced, usually over a guidewire (not shown), until an occlusion balloon 115 at its distal end is disposed in the ascending aorta 116 between the coronary ostia and the brachiocephalic artery. Blood may be vented from ascending aorta 116 through a port 120 at the distal end of the aortic occlusion catheter 113 in communication with an inner lumen in aortic occlusion catheter 113, through which blood may flow to the proximal end of the catheter. The blood may then be directed to a blood filter/recovery system 121 to remove emboli, and then returned to the patient's arterial system via CPB system 104.

When it is desired to arrest cardiac function, occlusion balloon 115 is inflated until it completely occludes ascending aorta 116, blocking blood flow therethrough. A cardioplegic fluid such as potassium chloride (KCl) is preferably mixed with oxygenated blood from the CPB system and then delivered to the myocardium in one or both of two ways. Cardioplegic fluid may be delivered in an anterograde manner, retrograde manner, or a combination thereof. In the anterograde delivery, the cardioplegic fluid is delivered from a cardioplegia pump 122 through an inner lumen in aortic occlusion catheter 113 and the port 120 distal to occlusion balloon 115 into the ascending aorta upstream of occlusion balloon 115. In the retrograde delivery, the cardioplegic fluid may be delivered through a retroperfusion catheter 123 positioned in the coronary sinus from a peripheral vein such as an internal jugular vein in the neck.

With cardiopulmonary bypass established, cardiac function arrested, and the right lung collapsed, the patient is prepared for surgical intervention within the heart H. At this point in the procedure, whether cardiac function is arrested and the patient is placed on CPB, or the patient's heart remains beating, the heart treatment procedure and system of the present invention remain substantially similar. The primary difference is that when the procedure of the present invention is performed on an arrested heart, the blood pressure in the internal chambers of the heart is significantly less. Hence, it is not necessary to form a hemostatic seal between the device and the heart wall penetration to inhibit blood loss through the penetration thereby reducing or eliminating the need for purse-string sutures around such penetrations, as will be described below.

In the preferred embodiment, however, the procedure is conducted while the heart is still beating. Accordingly, it is necessary to form a hemostatic seal between the ablation device and the penetration. Preferably, purse-string sutures 58, 60, 61, 62 and 63 (FIGS. 3A and 3B) are placed in the heart walls at strategic or predetermined locations to enable introduction of the ablating probes into the heart while maintaining a hemostatic seal between the probe and the penetration.

As best viewed shown in FIG. 11A, in order to gain access to the right atrium of the heart, a pericardiotomy is performed using thoracoscopic instruments introduced through retractor access port 67. Instruments suitable for use in this procedure, including thoracoscopic angled scissors 130 and thoracoscopic grasping forceps 131, are described in commonly assigned U.S. Pat. No. 5,501,698, issued Mar. 26, 1996, which is incorporated herein by reference.

After incising a T-shaped opening in the pericardium 132 (about 5.0 cm in length across and about 4.0 cm in length down, FIG. 11A), the exterior of the heart H is sufficiently exposed to allow the closed-chest, closed-heart procedure to be performed. To further aid in visualization and access to the heart H, the cut pericardial tissue 133 is retracted away from the pericardial opening 135 with stay sutures 136 (FIG. 11C) extending out of the chest cavity. This technique allows the surgeon to raise and lower the cut pericardial wall in a manner which reshapes the pericardial opening 135 and retracting the heart H slightly, if necessary, to provide maximum access for a specific procedure.

To install stay suture 136, a curved suture needle 137 attached to one end of a suture thread 138 is introduced into the chest cavity through passageway 67 with of a thoracoscopic needle driver 140 (FIG. 11B). Once the suture needle 137 and thread 138 have been driven through the cut pericardial tissue, the suture thread 138 is snared by a suture snare device 141. This is accomplished by positioning a hooked end 142 of suture snare device 141 through at least one additional percutaneous intercostal penetration 143 positioned about the chest to enable penetration into the thoracic cavity. In the preferred arrangement, a trocar needle (not shown) is employed which not only forms the penetration, but also provides access into the thoracic cavity without snaring tissue during removal of the snare device.

Accordingly, both ends of the suture thread 138 are snared and pulled through the chest wall for manipulation of the stay suture from outside of the body cavity. The ends of the stay suture 136 are coupled to a surgical clamp (not shown) for angled manipulation and tension adjusting. While only two stay sutures are illustrated, it will be appreciated that more stay sutures may be employed as needed to further manipulate the pericardial opening.

Turning now to FIG. 11C, a first 4-0 purse-string suture 58, for example, is placed in the heart wall proximate the site at which it is desired to initiate the first heart wall penetration 146 (FIG. 11D). Again, this is accomplished by using a thoracoscopic needle driver to drive the suture needle through the heart wall to form a running stitch in a circular pattern approximately 1.0-3.0 mm in diameter. A double-armed suture may also be used, wherein the suture thread 145 (about 3 mm to about 10 mm in diameter) has needles (not shown) at both ends, allowing each needle to be used to form one semi-circular portion of the purse-string. Suture thread 138 is long enough to allow both ends of the suture to be drawn outside of the chest cavity once purse-string suture 58 has been placed. The suture needle is then cut from thread 145 using thoracoscopic scissors.

To tension the purse-string suture 58, the suture threads 145 are pulled upon gathering the stitched circular pattern of tissue together before commencement of the formation of a penetration through the heart wall within the purse-string suture. One or a pair of thoracoscopic cinching instruments 147, such as a Rumel tourniquet, may be employed to grasp a loop of purse-string suture 58. As best viewed in FIG. 11D, cinching instrument 147 comprises a shaft 148 with a slidable hook 150 at its distal end thereof for this purpose. Hook 150 may be retracted proximally to frictionally retain suture thread 145 against the distal end of shaft 148. By retracting or withdrawing the cinching instrument 147, the purse-string suture 58 is cinched tightly, thereby gathering heart wall tissue together to form a hemostatic seal.

The cinching instrument may be clamped in position to maintain tension on suture thread 145. Preferably, however, a slidable tensioning sleeve 151 (FIG. 11D), commonly referred to as a snugger, may be provided in which the suture threads are positioned through a bore extending therethrough. The snugger is then slid along the suture thread until it abuts against the epicardial surface 152 of the heart wall. The cinching instrument is then pulled proximally relative to tensioning sleeve 151 to obtain the desired degree of tension on suture thread 145. Tensioning sleeve 151 is configured to frictionally couple to suture thread 145 to maintain tension on the suture.

An incision device 153 is introduced through access device 68 into the chest cavity for piercing the heart H. A blade 155 positioned on the distal end of a manipulating shaft 156 is advanced to pierce the heart wall within the bounds of purse-string suture 58. The blade 155 is preferably about 5.0 mm in length and about 3.0 mm wide terminating at the tip thereof. FIG. 11D illustrates that as the incision device 153 is manually moved further into contact with the epicardial surface 152 of the heart wall, blade 155 will be caused to pierce therethrough to form a penetration of about 1.0-2.0 mm across.

In the preferred form, the blade 155 is rigidly mounted to shaft 156 for direct one-to-one manipulation of the blade. Alternatively, however, the incision device may employ a spring loaded mechanism or the like which advances the blade forwardly from a retracted position, retracted in a protective sleeve of the shaft, to an extended position, extending the blade outside of the sleeve and into piercing contact with the tissue. In this embodiment, a button or the like may be provided near the proximal end of the shaft for operation of the blade between the retracted and extended positions.

To facilitate formation of the penetration by the incision device, a thoracoscopic grasping instrument (not shown) may be employed to grasp the heart wall near purse-string suture 58 to counter the insertion force of blade 155 and incision device 153. As blade 155 penetrates the heart wall, incision device 153 is advanced to extend transmurally into the heart through the penetration 146 formed in heart wall.

As above-indicated in FIGS. 3A and 3B, the entire procedure is preferably performed through a series of only five purse-strings sutures 58, 60, 61, 62 and 63, and the corresponding cardiac penetrations 146, 157, 158, 160 and 161 of which two penetrations 158, 160 are strategically positioned in the right atrium RA; one penetration 161 is positioned in the left atrium LA; and two penetrations 158, 160 are positioned near the pulmonary vein trunk 108. Such small incisions are significantly less traumatic on the heart tissue muscle than the elongated transmural incisions of the prior MAZE techniques.

Referring now to FIGS. 3A, 12A-12C and 13, the system and procedure of the present invention will be described in detail. Preferably, the first series of lesions is formed on the right atrium RA to form a posterior longitudinal right atrial lesion 50 and a tricuspid valve annulus lesion 51. It will be appreciated, however, that the transmural lesions can be formed in any order without departing from the true spirit and nature of the present invention.

By strategically placing the first heart wall penetration 146 of first purse-string suture 58 at the base of the right atrial appendage RAA where the anticipated intersection between the longitudinal right atrial lesion 50 and the tricuspid valve annulus lesion 51 are to occur (FIG. 12C), these two lesions can be formed through a series of three independent ablations. As best viewed in FIG. 12A, the upper section segment 162 (half of the longitudinal right atrial lesion 50) is formed using a right angle probe 163 (FIG. 24) having a first elbow portion 166 positioned between the generally straight elongated shaft 66 and the generally straight ablating end. The first elbow portion has an arc length of about 85.degree. to about 95.degree. and a radius of curvature of about 3.2 mm to about 6.4 mm. The ablating end 70 is preferably about 2.0 mm to about 4.0 mm in diameter, and about 2.0 cm to about 6.0 cm in length. In this configuration, the ablating surface 65 extends, circumferentially, from a distal end 165 thereof to just past an elbow portion 166 of the right angle probe 163.

Initially, the probe ablating end 70 and the shaft 66 of probe 163 is introduced into the thoracic cavity through the retractor 68 by manipulating a handle (not shown) releasably coupled to fitting 71. To facilitate location of the first penetration with the probe, the distal end 165 is guided along the shaft 156 of incision device 153 (FIG. 11D) until positioned proximate the first penetration 146. Subsequently, the blade 155 of incision device is withdrawn from the first penetration whereby the distal end of the probe is immediately inserted through the first penetration. Not only does this technique facilitate insertion of the probe but also minimizes loss of blood through the penetration.

Once the distal end 165 of the right angle probe 163 has been inserted and negotiated through the first penetration, the first purse-string suture may require adjustment to ensure the formation of a proper hemostatic seal between the penetration and the shaft of the probe. If the loss of blood should occur, the purse-string suture can be easily tightened through either a Rumel tourniquet or tensioning sleeve 151.

FIG. 12A best illustrates that the right angle probe 163 is preferably inserted through the penetration 146 until an elbow portion 166 thereof just passes through the penetration. Although the angular manipulation of the end of the right angle probe is limited due to the access provided by the retractor, the insertion should be easily accommodated since the heart wall tissue of the right atrium is substantially resilient and flexible. Again, a thoracoscopic grasping instrument (not shown) may be employed to grasp the heart wall near the first purse-string suture 58 to counter the insertion force of right angle probe 163 through the first penetration 146. Once the ablating end is inserted to the desired depth and through the assistance of either direct viewing or laparoscopic viewing, the elongated ablating end 70 is oriented to position a longitudinal axis thereof generally parallel to the right atrioventricular groove. This upper section segment 162 of the longitudinal right atrial lesion 50 extends generally from the first penetration 146 to the orifice of the superior vena cava 111. By retracting the probe rearwardly out of the passageway of the retractor 68 generally in the direction of arrow 167, the ablating surface will be caused to sufficiently contact the right atrial endocardium.

As mentioned above, the probe may use any method to ablate the heart tissue. When using a cryogenic ablating system, the cryogen stored in a Dewar vessel or pressurized cylinder is selectively released where it passes into the boiler chamber 75 of the device 163, thereby cooling the probe ablating surface for localized ablation of heart tissue. As previously stated, to warrant proper transmural ablation of the interior wall of the right atrium, continuous contact of the ablating surface therewith should occur for about 2-4 minutes. Visually, however, transmural cryosurgical ablation of the tissue is generally represented by a localized lightening or discoloration of the epicardial surface 168 of the ablated heart tissue which can be directly viewed through the access port 67 of access device 68. This method of determining cryoablation of the tissue can be used in combination with the timed probe contact therewith. As a result, the upper section segment 162 of the longitudinal right atrial lesion 50 will be formed.

Once the desired elongated portion of heart tissue has been ablated, caution must be observed before the ablating surface 65 probe can be separated from the contacted endocardial surface of the heart tissue. Due to the extremely low temperatures of the ablating surface (i.e., about −50.degree. to about −80.degree.) and the moistness of the heart tissue, cryoadhesion can occur. Accordingly, the probe tip must be properly thawed or defrosted to enable safe separation after the tissue has been properly ablated.

For example, after sufficient transmural cryoablation of the heart tissue, thawing is commenced by halting the flow of cryogen through the probe and maintaining continuous contact between the probe ablating surface and the cryoablated tissue. After about 10-20 seconds, and preferably about 15 seconds, the conductive and convective heat transfer or heat sink effect from the surrounding tissue and blood is sufficient to reverse the cryoadhesion. Of course, it will be appreciated that such heat transfer is more efficient when the procedure is performed on a beating heart as opposed to an arrested heart. Alternatively, the system may also be provided with a defrost mode which serves to warm the tissue to room temperature. This may be accomplished by raising the pressure of the cryogen adjacent the ablating surface such that its temperature increases, for example, by restricting the exhaust gas flow.

Furthermore, to facilitate thawing of the exterior surface of the ablated tissue, a room temperature or slightly heated liquid may be wetted or impinged upon the exterior surface of the ablated area. In the preferred embodiment, such liquid may include saline or other non-toxic liquid introduced into the thoracic cavity through the retractor passageway 67.

Generally, multiple lesions can be formed through a single purse-string suture either through the use of assorted uniquely shaped ablating devices or through the manipulation of a single ablating device. Accordingly, while maintaining the hemostatic seal between the probe shaft and the penetration, the respective ablating device can be manipulated through the respective penetration to strategically contact the corresponding elongated ablating surface with another selected portion of the interior surface of the muscular wall for transmural ablation thereof. For instance, without removing the right angle cryoprobe from the first penetration, the ablating surface 65 is rotated approximately 180.degree. about the longitudinal axis to re-position the distal end generally in a direction toward the orifice of the inferior vena cava 103. As shown in FIG. 12B, such positioning enables the formation of the remaining lower section segment 170 of the longitudinal right atrial lesion 50. However, since the lower section segment 170 of the lesion is shorter in length than that of the upper section segment, the length of the elongated ablating surface contacting the interior wall of right atrium must be adjusted accordingly. This length adjustment is accomplished by partially withdrawing the probe ablating surface 65 from the first penetration 146 by the appropriate length to ablate the lower section segment 170. Due to the substantial flexibility and resiliency of the heart tissue, such maneuverability of the probe and manipulation of the tissue is permissible.

Similar to the formation of the upper section segment 162 of the longitudinal right atrial lesion 50, the right angle probe 163 is retracted rearwardly, generally in the direction of arrow 167, causing the ablating surface 65 of the probe to sufficiently contact the endocardium of the right atrium. After the cryogen has continuously cooled the elongated ablating surface 65 of the probe for about 2-4 minutes, the remaining lower section segment of the longitudinal right atrial lesion 50 will be formed. Thereafter, the probe is defrosted to reverse the effects of cryoadhesion. It will be understood that while it is beneficial to employ the same right angle probe to perform both the upper and lower section segments of the longitudinal right atrial lesion, a second right angle probe having an ablating surface shorter in length than that of the first right angle probe could easily be employed.

Utilizing the same first penetration, the tricuspid valve annulus lesion 51 can be formed employing one of at least two probes. Preferably, the right angle probe 163 may again be used by rotating the elongated ablating surface 65 about the probe shaft longitudinal axis to reposition the distal end transpericardially, generally in a direction across the lower atrial free wall and toward the tricuspid valve 171 (FIGS. 12C and 13). The distal end of the probe ablating surface 65, however, must extend all the way to the tricuspid valve annulus 172. Hence, in some instances, due to the limited maneuvering space provided through the retractor passageway, the formation of the tricuspid valve annulus lesion 51 with the right angle probe may be difficult to perform.

In these instances, a special shaped tricuspid valve annulus probe 173 (FIGS. 13 and 25) is employed which is formed and dimensioned to enable contact of the probe ablating surface 65 with appropriate portion of the right atrium interior wall all the way from the first penetration 146 to the tricuspid valve annulus 172 to form the tricuspid valve annulus lesion 51. The ablating end 70 and the shaft 66 of this probe cooperate to form one of the straighter probes 57 of the set shown in FIG. 4.

FIG. 25 best illustrates the tricuspid valve annulus probe 173 which includes an elongated shaft 66 having a first elbow portion 166 positioned between a generally straight first portion 175 and a generally straight second portion 176 having a length of about 2.0 cm to about 6.0 cm. The first elbow portion has an arc length of about 20.degree. to about 40.degree. and a radius of curvature of about 13.0 cm to about 18.0 cm. Further, a second elbow portion 177 is positioned between the second portion 176 and a third portion 178 of the shaft, angling the third portion back toward the longitudinal axis of the first portion 175 of the elongated shaft 66. The third portion 178 includes a length of about 2.0 cm to about 6.0 cm, while the second elbow portion has an arc length of about 5.degree. to about 20.degree. and a radius of curvature of about 15.0 cm to about 20.0 cm. The ablating end 70 is relatively straight and is coupled to the distal end of the third portion 178 of the elongated shaft 66 in a manner angling the ablating end back away from the longitudinal axis and having an arc length of about 5.degree. to about 20.degree. and a radius of curvature of about 13.0 cm to about 18.0 cm. The ablating end 70 is formed to extend from the first penetration and to the rim 172 of the tricuspid valve 171 from outside of the body cavity. For this probe, the ablating surface 65 is preferably about 2.0 cm to about 6.0 cm in length. It will be understood that while the illustrations and descriptions of the probes are generally two dimensional, the configurations of the shaft and ablating end combinations could be three dimensional in nature.

Using the insertion technique employed by the right angle probe 163 during the formation of the longitudinal right atrial lesion 50, upon withdrawal of the right angle probe from the first penetration 146, the distal end of the tricuspid valve annulus probe 173 is immediately inserted therethrough to facilitate alignment and minimize the loss of blood.

Regardless of what instrument is employed, once the probe ablating surface 65 is strategically oriented and retracted to contact the endocardial surface, the cryogen is selectively released into the boiler chamber to subject the desired tissue to localized cryothermia. Due to the nature of the transmural ablation near the tricuspid valve annulus, the need for dividing all atrial myocardial fibers traversing the ablated portion is effectively eliminated. Thus, the application of the nerve hook utilized in the prior MAZE procedures is no longer necessary.

As illustrated in FIG. 13, the distal end of the probe must extend to the base of the tricuspid valve annulus 172. This lesion is difficult to create since the right atrial free-wall in this region lies beneath the atrioventricular groove fat pad (not shown). To facilitate orientation of the ablating end of the probe relative the valve annulus and to better assure the formation of a lesion which is transmural in nature, an alternative tricuspid valve clamping probe 180 (FIG. 26) may be employed rather than or in addition to the tricuspid valve annulus probe 173.

This probe includes a primary shaft 66 and ablating end 70 which are cooperatively shaped and dimensioned substantially similar to the tricuspid valve annulus probe 173. A clamping device 181 of clamping probe 180 includes a mounting member 179 providing an engagement slot 182 formed for sliding receipt of a pin member 184 coupled to primary shaft 66. This arrangement pivotally couples the clamping device 181 to the primary shaft 66 for selective cooperating movement of a clamping jaw portion 183 of the clamping device 181 and the ablating end 70 between a released position, separating the clamping jaw portion from the ablating end 70 (phantom lines of FIG. 26), and a clamped position, urging the clamping jaw portion against the ablating end 70 (solid lines of FIG. 26).

The clamping jaw portion 183 is shaped and dimensioned substantially similar to the corresponding ablating end 70 to enable clamping of the heart tissue therebetween when the tricuspid valve clamping probe 180 is moved to the clamped position. At the opposite end of the clamping jaw portion 183 is a handle portion 185 for manipulation of the jaw portion between the released and clamped positions in a pliers-type motion.

To perform this portion of the procedure using the tricuspid valve clamping probe 180, the clamping jaw is moved toward the released position to enable the distal end of the ablating end to be negotiated through the first penetration 146. Using direct viewing through the retractor or visually aided with an endoscope, the ablating end is moved into contact with the predetermined portion of the right atrium interior wall all the way from the first penetration 146 to the tricuspid valve annulus 172. Subsequently, the clamping jaw portion is moved to the clamped position, via handle portion 185, to contact the epicardial surface 168 of the heart wall opposite the tissue ablated by the probe. This arrangement increases the force against the ablating surface 65 to facilitate contact and heat transfer. Cryogen is then provided to the boiler chamber to cool the ablating surface 65 thereby forming the tricuspid valve annulus lesion 51. Once the probe is removed from the first penetration 146, the first purse-string suture 58 is further tightened to prevent blood loss.

The engagement slot 182 of mounting member 179 is formed to permit release of the pin member 184 therefrom. Hence, the clamping device 181 can be released from primary shaft 66 of the clamping probe 180. This arrangement is beneficial during operative use providing the surgeon the option to introduce the clamping probe 180 into the thoracic cavity as an assembled unit, or to first introduce the ablation end 70 and primary shaft 66, and then introduce of the clamping device 181 for assembly within the thoracic cavity.

Turning now to FIG. 14, a second 4-0 purse-string suture 59 is placed in the right atrial appendage RAA proximate a lateral midpoint thereof in the same manner as above-discussed. This portion of the heart is again accessible from the right side of the thoracic cavity through the first access device 68. A second penetration 157 is formed central to the second purse-string suture wherein blood loss from the second penetration is prevented through a second tensioning sleeve 186. Subsequently, the distal end of a right angle probe or a right atrium counter lesion probe 187 (FIGS. 15 and 27), is inserted through second penetration 157 and extended into the right atrial appendage chamber. Second purse-string suture 59 may then be adjusted through second tensioning sleeve 186, as necessary to maintain a hemostatic seal between the penetration and the probe.

The right atrium counter lesion probe 187 includes an elongated shaft 66 having a first elbow portion 166 positioned between a relatively straight first portion 175 and a generally straight second portion 176, whereby the first elbow portion has an arc length of about 85.degree. to about 95.degree. and a radius of curvature of about 1.9 cm to about 3.2 cm. The second portion is preferably about 2.0 cm to about 6.0 cm in length. Further, a second elbow portion 177 is positioned between the second portion 176 and a generally straight third portion 178 of the shaft which is about 2.0 cm to about 6.0 cm in length. The second elbow portion has an arc length of about 40.degree. to about 70.degree. and a radius of curvature of about 3.2 cm to about 5.7 cm, angling the third portion 178 back toward the longitudinal axis of the first portion 175 of the elongated shaft 66. The ablating end 70 is coupled to the distal end of the third portion 178 of the elongated shaft 66, and includes an arc length of about 85.degree. to about 95.degree. and a radius of curvature of about 6.0 mm to about 19.0 mm to curve the distal end thereof back toward the longitudinal axis of the first portion 175 of the shaft 66. Thus, this equates to an ablating surface length of preferably about 4.0 cm to about 8.0 cm in length.

This configuration enables the ablating end 70 of probe 187 to access the right lateral midpoint of the atrial appendage RAA where the second penetration 157 is to placed. FIGS. 14 and 15 best illustrate that the position of this second penetration 157 is higher up than the first penetration, relative the heart, when accessed from the predetermined intercostal penetration 92. Upon insertion of the distal end of the probe through the second penetration 157, the ablating end 70 is inserted into the right atrium chamber to the proper depth. The handle (not shown) of the probe 187 is manipulated and oriented from outside the thoracic cavity to position the distal end of the ablating surface 65 in a direction generally toward the first purse-string suture 58. The probe is retracted rearwardly out of the retractor passageway, generally in the direction of arrow 167 in FIG. 14, to urge the ablating surface 65 of the probe into contact with the endocardial surface of the interior wall of the right atrial appendage RAA. As a result, the perpendicular lesion 53 of the right atrial appendage is transmurally formed.

The next lesion to be created is the anteromedial counter lesion 55 which is to be formed through the second penetration 157. This lesion is positioned just anterior to the apex of the triangle of Koch and the membranous portion of the interatrial septum. Without removing the right atrium counter lesion probe 187 from the second penetration 157, the elongated ablating surface 65 is urged further inwardly through the second penetration 157 toward the rear atrial endocardium of the right atrial appendage RAA (FIG. 15). Upon contact of the ablating surface 65 with the rear atrial wall, the probe 187 is slightly rotated upwardly in the direction of arrows 191 in FIG. 15 to exert a slight force against the rear endocardial surface. Again, this ensures ablative contact therebetween to enable formation of the anteromedial counter surgical lesion 55. Subsequently, the probe is properly defrosted and withdrawn from the second penetration 157 whereby the second purse-string suture 59 is cinched tighter to prevent blood loss therefrom. It will be understood that since these two lesions are formed through cryothermic techniques, the need for atrial retraction and endocardial suturing employed in connection with the formation of the transmural incision of the MAZE III procedure can be eliminated.

The next step in the procedure is an atrial septotomy to from an anterior limbus of the fossa ovalis lesion 192. The formation of this lesion will likely be performed without direct or laparoscopic visual assistance since the ablation occurs along internal regions of the interatrial septum wall 193. Initially, as best illustrated in FIGS. 16-18, two side-by-side purse-string sutures 61 and 62 are surgically affixed to an epicardial surface 168 proximate the pulmonary trunk 108 using the same techniques utilized for the first and second purse-string sutures. The third purse-string suture 61 is positioned on one side of the septum wall 193 for access to the right atrium chamber, while the fourth purse-string suture 62 is positioned on the opposite side of the septum wall for access to the left atrium chamber.

FIG. 17 further illustrates that the introduction of thoracoscopic instruments and access to the third and fourth purse-strings are preferably provided through the retractor 68. After the third and fourth tensioning sleeves 195, 196 have been mounted to the respective suture threads, an incision device (not shown) is introduced into the thoracic cavity to incise the penetrations central to the respective purse-string sutures. Due to the angle of the upper heart tissue surface relative the retractor 68, the incision device may incorporate an angled end or blade for oblique entry through the heart wall tissue in the direction of arrow 197 to form the third and fourth penetrations 158, 160 (FIG. 18). Alternatively, the incision device may include a blade end which is capable of selective articulation for pivotal movement of the blade end relative the elongated shaft. Use of a thoracoscopic grasping instrument facilitates grasping of the epicardium near the pulmonary trunk 108 to counter the insertion force of the angled blade during formation of the respective penetrations 158, 160.

To create the lesion across the anterior limbus of the fossa ovalis lesion 192, a special atrial septum clamping probe 198 (FIGS. 17 and 28) is provided having opposed right angled jaw portions 200, 201 formed and dimensioned for insertion through the corresponding third and fourth penetrations 158, 160 for clamping engagement of the anterior limbus of the fossa ovalis therebetween. As illustrated in FIG. 28, the atrial septum clamping probe 198 includes a primary clamping member 202 having a generally straight, elongated clamping shaft 66 with a first elbow portion 166 positioned between the clamping shaft 66 and a generally straight outer jaw portion 200 (ablating end 70), whereby the first elbow portion has an arc length of about 85.degree. to about 95.degree. and a radius of curvature of about 3.2 mm to about 6.4 mm. The ablating surface extends just beyond elbow portion 166 and is of a length of preferably about 2.0 cm to about 6.0 cm.

In accordance with the special atrial septum clamping probe 198 of the present invention, an attachment device 203 is coupled to the clamping shaft 205 which includes an inner jaw portion 201 formed and dimensioned to cooperate with the outer jaw portion 200 (i.e., the elongated ablating surface 65) of clamping member 202 for clamping engagement of the interatrial septum wall 193 therebetween (FIG. 17). Hence, the inner jaw portion and the outer jaw portion move relative to one another between a clamped condition (FIG. 17 and in phantom lines in FIG. 28) and an unclamped condition (FIG. 14A and in solid lines in FIG. 28). In the unclamped condition, the inner jaw portion 201 of the attachment device 203 is positioned away from the outer jaw portion 200 to permit initial insertion of the distal end 165 of the outer jaw portion 200 of the clamping probe 198 into the fourth penetration 160, as will be discussed.

The attachment device 203 is preferably provided by a generally straight, elongated attachment shaft 206 having a first elbow portion 207 positioned between the attachment shaft 206 and a generally straight inner jaw portion 201. FIG. 28 best illustrates that the first elbow portion of inner jaw portion 201 has an arc length and radius of curvature substantially similar to that of the outer jaw portion 200. Further, the length of the inner jaw portion is preferably about 2.0 mm to about 6.0 mm.

In the preferred form, the attachment shaft 206 is slidably coupled to the clamping shaft 66 through a slidable coupling device 208 enabling sliding movement of the inner jaw portion 201 between the clamped and unclamped conditions. Preferably, a plurality of coupling devices 208 are provided spaced-apart along the attachment shaft 206. Each coupling device includes a groove 210 (FIG. 29) formed for a sliding, snap-fit receipt of the clamping shaft 66 therein for sliding movement of the attachment device in a direction along the longitudinal axis thereof.

The coupling devices are preferably composed of TEFLON®, plastic, polyurethane or the like, which is sufficiently resilient and bendable to enable the snap-fit engagement. Further, such materials include sufficient lubricating properties to provide slidable bearing support as the clamping shaft 66 is slidably received in groove 210 to move inner jaw portion 201 between the clamped and unclamped conditions. Moreover, the coupling device configuration may permit rotational motion of the inner jaw portion 201 about the attachment shaft longitudinal axis, when moved in the unclamped condition. This ability further aids manipulation of the clamping probe 198 when introduced through the access device 68 and insertion through the corresponding fourth penetration 160.

In the clamped condition, the inner jaw portion 201 is moved into alignment with the outer jaw portion 200 of the clamping member 202 for cooperative clamping of the septum wall 193 therebetween. An alignment device 211 is preferably provided which is coupled between the clamping member 202 and the slidable attachment device 203 to ensure proper alignment relative one another while in the clamped condition. This is particularly necessary since the inner jaw portion 201 is capable of rotational movement about the clamping shaft longitudinal axis, when moved in the unclamped condition. In the preferred embodiment, FIG. 30 best illustrates that alignment device 211 is provided by a set of spaced-apart rail members 212, 212' each extending from the outer jaw portion 200 to the clamping shaft 66 of the clamping member 202. The rail members 212, 212' cooperate to define a slot 213 therebetween which is dimensioned for sliding receipt of an elbow portion 207 of the inner jaw portion 201.

To further facilitate alignment between the inner jaw portion and the outer jaw portion, the elbow portion 207 of the inner jaw portion 201 may include a rectangular cross-section dimensioned for squared receipt in the slot 213 formed between the rail members 212, 212'. Alternatively, alignment may be provided by the inclusion of a locking device positioned at the handle of the probe, or by indexing detents included on the clamping shaft.

Due to the relatively close spacing and placement of the third and fourth purse-string sutures 61, 62 in relation to the heart and the retractor 68, substantial precision is required for simultaneous insertion of the jaw portion distal ends 165, 215. This problem is further magnified by the limited scope of visualization provided by either direct viewing through the retractor and/or with the endoscope. Accordingly, the septum clamping probe 198 includes staggered length jaw portions which position the distal end 165 of the outer jaw portion 200 slightly beyond the distal end 215 of the inner jaw portion 201 to facilitate alignment and insertion through the penetrations 158, 160. In the preferred form, the right angled clamping member 202 is initially introduced through access device 68 for positioning of the distal end proximate the fourth purse-string suture 62. Upon alignment of the outer jaw distal end 165 with the fourth penetration 160, the clamping member 202 is manipulated in the direction of arrow 197 for insertion of the outer jaw portion partially into the left atrium chamber. The initial insertion depth of the tip is to be by an amount sufficient to retain the outer jaw portion 200 in the fourth penetration, while permitting the shorter length inner jaw portion 201 of the attachment device to move from the unclamped condition toward the clamped condition (FIGS. 18A and 18B).

It will be understood that the slidable attachment device 203, at this moment, will either be unattached to the right angle probe or will be prepositioned in the unclamped condition. In the former event, the slidable attachment device 203 will be introduced through the access device 68 and slidably coupled or snap fit to the clamping shaft 66 of the clamping member 202 via coupling devices 208. As the inner jaw portion 201 is advanced in the direction of arrow 216 toward the clamped condition, the attachment shaft 206 is rotated about its longitudinal axis, if necessary, until the elbow portion 207 is aligned for receipt in the slot 213 formed between the spaced-apart rails members 212, 212'. In this arrangement, the inner jaw portion 201 will be aligned co-planar with the outer jaw portion 200 of the clamping member 202.

The length of the inner jaw portion 201 is preferably shorter than the length of the outer jaw portion 200 of clamping member 202 (preferably by about 5 mm). With the distal end 165 of the outer jaw portion 200 partially penetrating the fourth penetration 160 and the distal end 215 of the inner jaw portion 201 aligned with the third penetration 158 (FIG. 18B), the jaw portions are moved in the direction of arrow 197 to position the jaws through the penetrations, on opposite sides of the septum wall 193, and into the atrial chambers.

As shown in FIG. 17, the jaw portions 200, 201 are inserted to a desired depth whereby the clamping probe can be aligned to pass through the anterior limbus of the fossa ovalis. When properly oriented, the jaw portions can be moved fully to the clamped position exerting an inwardly directed force (arrows 216, 216') toward opposed sides of the interatrial septum wall 193. Subsequently, the cryogen is released into the boiler chamber of the outer jaw portion of the clamping member thereby cooling the ablating surface 65 and subjecting the septal wall to cryothermia.

Due in part to the substantial thickness of this heart tissue, to secure proper transmural ablation of the interior septal wall of the right atrium, continuous contact of the ablating surface 65 therewith should transpire for at least 3-4 minutes to create the anterior limbus of the fossa ovalis ablation. The clamping probe 198 and the septum wall are to be properly defrosted and subsequently withdrawn from the third and fourth penetrations 158, 160, whereby the third and fourth purse-string sutures 61, 62 are cinched tighter to prevent blood loss therefrom.

The length of the outer jaw portion is preferably between about 3 cm to about 5 cm, while the length of the inner jaw portion is generally about 5 mm less than the length of the outer jaw portion. Further, the diameter of the inner and outer jaw portions is preferably between about 2-4 mm. The determination of the diameter and/or length of the particular jaw portions and combinations thereof to be utilized will depend upon the particular applications and heart dimensions.

The clamping arrangement of this probe enables a substantial clamping force urged between the two opposed jaw portions for more efficient heat conduction. This configuration more effectively ablates the relatively thicker septum wall since greater leverage can be attained. Accordingly, in the preferred embodiment, only the outer jaw portion 200 (i.e., the ablating surface 65) of the clamping member 202 needs to be cooled to be effective. It will be appreciated, however, that the attachment device 203 may include the boiler chamber to cool the inner jaw portion as well for ablation of both sides of the septum wall 193.

In an alternative embodiment of the clamping probe 198, as shown in FIG. 31, the outer and inner jaw portions 200, 201 may cooperate to provide a gap 217 at and between the outer elbow portion 166 and the inner elbow portion 207. This gap 217 is formed to accommodate the typically thicker tissue juncture 218 where the septum wall 193 intersects the outer atrial wall 220. Hence, when the clamping probe 198 is moved to the clamped condition, the gap 217 is formed to receive this tissue juncture 218 so that a more constant compression force may be applied across the septum wall between the opposing jaws. This may be especially problematic when the tissue juncture is significantly thicker than the septum wall which, due to the disparity in thickness, may not enable the distal ends of the respective jaw portions to effectively contact the septum wall for transmural ablation thereof.

While FIG. 31 illustrates that the gap 217 is primarily formed through the offset curvature at the elbow portion 207 of inner jaw portion 201, it will be understood that the outer jaw portion 200 alone or a combination thereof may be employed to form the gap 217. Further, in some instances, the clamping probe 198 may be derived from the right angle probe set forth above.

After completion of the above-mentioned series of elongated lesions formed through the retractor, the right atrial appendage RAA may be excised along the direction of solid line 221 in FIG. 3 and broken line 222 in FIG. 19, to be described below. This excision is optional depending upon the particular circumstance since the risk of a fatal clot or thromboembolism is not as great as compared to left atrial appendage LAA. Should this excision be performed, the right atrial appendage RAA will, preferably, first be sutured closed along broken line 222 using conventional thoracoscopic instruments. This closure must be hemostatic to prevent blood loss when the right atrial appendage is excised. Once a hemostatic seal is attained, the appendage is excised using thoracoscopic scissors or an incision device.

While suturing is the preferred technique for hemostatically sealing the right atrial chamber, the right atrial appendage may first be surgically closed along broken line 222 using staples. In this procedure, a thoracoscopic stapling device would be inserted into the thoracic cavity through the retractor passageway 67 for access to the appendage. Moreover, the right atrial appendage may be conductively isolated by applying a specially designed cryoprobe clamping device (not shown) formed to be placed across the base of the appendage to engage the exterior surface thereof. This lesion will extend completely around the base along the line 221, 222 in FIGS. 3 and 19 which corresponds to the right atrial appendage excision in the prior surgical procedures.

The next series of lesions are accessed through the left atrium LA. Accordingly, a second access device 223, preferably the retractor 68, placed between the ribs on the left side of the patient P, usually in the third or fourth intercostal space, and most preferably the third intercostal space as shown in FIG. 11A. Again, this percutaneous penetration is positioned so that thoracoscopic instruments introduced through it may be directed toward the left atrium LA of the heart H. When additional maneuvering space is necessary, the intercostal space between the ribs may be through spreading of the adjacent ribs, or portions of the ribs can be easily removed to widen the percutaneous penetration. Further, the right lung will be re-inflated for use, while the left lung will be deflated to promote access while surgery is being performed. Other lung ventilation techniques may be employed such as high frequency ventilation without departing from the true spirit and nature of the present invention.

Subsequently, a pericardiotomy is performed to gain access to the left side of the heart H utilizing thoracoscopic instruments introduced through the retractor 68. Using the same technique mentioned above, a fifth 4-0 purse-string suture 63 is then formed in the atrial epicardium of left atrial appendage LAA proximate a lateral midpoint thereof. Through a fifth penetration 161 formed central to the fifth purse-string suture 63, the orifices of the pulmonary veins can be accessed to procure conductive isolation from the remainder of the left atrium LA.

In the preferred embodiment, the pulmonary vein isolation lesion 52 is formed using a two or more step process to completely encircle and electrically isolate the four pulmonary veins. In the preferred form, a four-step technique is employed initially commencing with the use of a C-shaped, probe 225. As best viewed in FIGS. 19A and 32, the probe includes an elongated shaft 66 and a C-shaped ablating end 70 mounted to the distal end of the shaft 66. The C-shaped ablating end 70 is shaped and dimensioned such that a distal end of the ablating end curves around and terminates in a region proximate the longitudinal axis extending through the shaft. The ablating end preferably includes an arc length of about 120.degree. to about 180.degree., and a radius of the arc between about 6.0 mm to about 25.0 mm. This equates to an ablating surface length of preferably about 3.0 cm to about 6.0 cm.

With the aid of a thoracoscopic grasping instrument (not shown in FIG. 19A), the distal end of probe 225 is inserted through fifth penetration 161 to a position past the semicircular ablating surface 65. A fifth tensioning sleeve 226 may be cinched tighter in the event to prevent blood loss therefrom.

To create the first segment 227 of the pulmonary vein isolation lesion 52, the distal end of the all-purpose probe is preferably positioned to contact the pulmonary endocardial surface 228 of the left atrium LA about 3-10 mm superior to the right superior pulmonary vein orifice 230. Through the manipulation of the probe handle from outside the body, a bight portion 232 of the ablating surface 65 is positioned about 3-10 mm outside of and partially encircling the right superior and left superior pulmonary vein orifices 230, 231. Once aligned, the ablating surface 65 of the probe is urged into ablative contact with the desired pulmonary endocardial surface 228 to form about ⅓ of the pulmonary vein isolation lesion 52 (i.e., the first segment 227).

Without removing the probe 225 from the fifth penetration 161, the probe 225 is rotated approximately 180.degree. about the longitudinal axis of the probe shaft 66 to reorient the ablating surface 65 to form the second segment 233 of the pulmonary vein isolation lesion 52. FIG. 19B best illustrates that the bight portion 232 of the probe is positioned on the other side of pulmonary trunk to contact the pulmonary endocardium about 3-10 mm just outside of and partially encircling the right inferior and left inferior pulmonary vein orifices 235, 236. To ensure segment continuity, the distal end of the probe is positioned to overlap the distal of the first segment 227 by at least about 5 mm. Once the probe bight portion 232 is aligned to extend around the pulmonary vein orifices, the ablating surface 65 thereof is urged into ablative contact with the desired pulmonary endocardium to form the second segment 233 of the pulmonary vein isolation lesion 52. After ablative contact and subsequent probe defrosting, the probe is retracted rearwardly from the fifth penetration 161 and removed from the second retractor 68. An articulating probe (not shown) may also be employed for this procedure which includes an ablating end capable of selected articulation of the ablating surface to vary the curvature thereof. In this probe, the articulation of the end may be manually or automatically controlled through control devices located at the handle portion of the probe. This probe may be particularly suitable for use in the formation of the pulmonary vein isolation lesion due to the anatomical access difficulties.

Immediately following removal of the probe 225, a right angle probe is to be inserted through the fifth penetration 161 of the left atrial appendage LAA, in the manner above discussed, to create a third segment 237 of the pulmonary vein isolation lesion 52. The formation of this segment may require a different right angle probe, having a shorter length ablating surface 65 (about 2.0 cm to about 6.0 cm) than that of the first right angle probe 163 utilized in the previous ablative procedures. As shown in FIG. 19C, the ablating surface 65 is oriented just outside the left superior pulmonary vein orifice 231 by at least about 5 mm. Again, to ensure proper segment continuity, it is important to overlap the distal end of the ablating surface 65 with the corresponding end of the lesion during the formation of the third segment 237 of the pulmonary vein isolation lesion 52. After the probe is manually urged into contact with the desired pulmonary endocardial surface 228, cryothermia is induced for the designated period to transmurally ablate the third segment 237 of the pulmonary vein isolation lesion 52. Subsequently, the right angle probe ablating surface 65 is properly defrosted to reverse cryoadhesion and enable separation from the tissue.

Similar to the use of the probe 225, without removing the right angle probe from the fifth penetration 161, the probe is rotated approximately 180.degree. about the longitudinal axis of the probe shaft to position the ablating surface 65 just outside the left inferior pulmonary vein orifice 236 by at least about 5 mm (FIG. 19D). Again, to ensure proper segment continuity, it is important to overlap both the distal end and the elbow portion of the ablating surface 65 with the corresponding ends of the second and third segments 233, 237 during the formation of the fourth segment 238 of the pulmonary vein isolation lesion 52. Fiberoptic visualization or the like is employed to facilitate proper continuity between the segments and placement of the probe. Once the probe is urged into contact with the desired left atrium interior surface, cryothermia is induced for the designated period to ablate the fourth segment of the pulmonary vein isolation lesion 52. After the right angle probe ablating surface 65 is properly defrosted, the probe is retracted rearwardly from the fifth penetration 161 and removed from the second retractor 68.

Formation of this last segment (i.e., fourth segment 238) completes the reentrant path isolation encircling the pulmonary veins (i.e., the pulmonary vein isolation cryolesion 52). It will be appreciated, of course, that the order of the segment formation which collectively defines the pulmonary vein isolation lesion 52 may vary. It is imperative, however, that there be continuity between the four segments. If the four-step procedure is performed properly, the opposed ends of the four segments should all overlap and interconnect to form one unitary ablation transmurally encircling the pulmonary trunk 108.

In accordance with the system and procedure of the present invention, an alternative two-step endocardial procedure may be performed to isolate the pulmonary veins. As shown in FIGS. 20A and 33, an S-shaped end probe 240 is provided having a uniquely shaped, opened-looped ablating surface 65 formed to substantially extend around or encircle the pulmonary vein orifices. The S-shaped probe 240 includes an elongated shaft 66 having a substantially straight first portion 175 and a C-shaped second portion 176 mounted to the distal end of the first portion and terminating at a position proximate the longitudinal axis of the first portion 175 of shaft 66. Mounted to the distal end of the C-shaped second portion 176 is a C-shaped ablating end 70 which curves back in the opposite direction such that the two C-shaped sections cooperate to form an S-shaped end. This unique shape enables the ablating surface 65 of ablating end 70 to have an arc length of between about 290.degree. to about 310.degree., with a radius of curvature of about 1.2 cm to about 3.0 cm.

FIG. 33 illustrates that the C-shaped ablating end 70 is shaped and dimensioned such that a distal end of the ablating end curves around and terminates in a region proximate the longitudinal axis extending through the shaft. Consequently, the ablating end 70, having a radius of about 12.0 mm to about 25.0 mm, can then extend substantially around the endocardial surface of the pulmonary vein trunk. This is accomplished by providing the C-shaped second portion 176 having a radius of curvature of at least bout 5 mm to about 7 mm which enables the unimpeded flow of cryogen through the delivery tube of the shaft 66. The elimination or substantial reduction of this C-shaped second portion 176 positioned just before the C-shaped ablating end 70 would create such an acute angle that the flow of cryogen about that angle may be impeded.

Using thoracoscopic grasping instruments, the distal end of this probe is carefully inserted through the fifth purse-string suture penetration 161. Due in part to the unique near-circular shape of the ablating surface 65, initial insertion through the fifth penetration may be one of the most difficult and problematic portions of this procedure.

As shown in FIG. 20A, after the ablating surface 65 of the probe 240 is successfully inserted through the fifth penetration 161, the looped ablating surface 65 is aligned and positioned to substantially encircle the pulmonary vein orifices. Through manipulation of the probe handle from outside the thoracic cavity, the probe ablating surface 65 is urged into contact with the pulmonary endocardial surface 228 about 3-10 mm just outside of the pulmonary vein orifices. Upon proper alignment and ablative contact with the epicardial tissue, a first segment 241 of this technique is formed (FIG. 20B) which preferably constitutes at least about ¾ of the pulmonary vein isolation lesion. After proper defrosting, the loop probe is removed from the fifth penetration and withdrawn through the retractor.

To complete this alternative two-step procedure, an alternative right angle probe, above-mentioned, is inserted through the fifth penetration 161 upon removal of the S-shaped probe 240. FIG. 20B illustrates that both the distal end and the elbow portion of the probe ablating surface 65 are aligned to overlap the corresponding ends of the first segment 241 during the formation of a second segment 242 of the pulmonary vein isolation lesion 52. This ensures continuity between the two connecting segments.

It will be understood that other shape probes may be employed to isolate the pulmonary trunk. The particular customized shape may depend upon the individual anatomical differences of the patient, especially since atrial fibrillation patients often have enlarged or distorted atria.

It may be beneficial to access and perform portions of either the four-step procedure or the two-step procedure through the right side of the thoracic cavity. In these instances, access may be achieved through the first access device 68 and the fourth penetration 160 of the fourth purse-string suture 62. Moreover, due to the arduous nature of the formation, placement and alignment between these segments composing the endocardial pulmonary vein isolation lesion in either the two or four segment procedure, it may be necessary to ablate an epicardial lesion 243 in the epicardial surface 168 encircling the pulmonary trunk 108 to ensure effective transmural tissue ablation for pulmonary vein isolation. Referring to FIGS. 21 and 33, an epicardial pulmonary vein loop probe 240, substantially similar to the probe employed in the procedure of FIG. 20A, is provided for introduction through the passageway of the retractor. This probe instrument includes an open-looped ablating surface 65 defining an opening 245 (FIG. 33) formed for passage of the pulmonary trunk 108 therethrough. Using thoracoscopic grasping instruments, the probe 240 is situated under the pulmonary veins wherein the pulmonary trunk 108 is urged through the opening 245 in the looped ablating surface. Once the ablating surface 65 is aligned to contact a pulmonary epicardial surface 168 of the pulmonary trunk 108 at a position opposite the epicardial pulmonary vein isolation lesion 52, cryogenic liquid is introduced into the boiler chamber of the loop probe 240 for cryogenic cooling of the ablating surface 65. After contact for the designated period (2-4 minutes) and proper probe defrosting, the loop probe is separated from the pulmonary trunk and retracted rearwardly out of the retractor 68.

Alternatively, this pulmonary epicardial surface isolation may be performed from the right side of the thoracic cavity through the first access device 68 (not shown). In this alternative method, the open-looped ablating surface 65 of the loop probe 240 is positioned behind the superior vena cava 111, across the anterior surface of the right pulmonary veins, and underneath the inferior vena cava 103. Once properly positioned, the epicardial surface 168 of the pulmonary trunk 108 can be ablated.

Turning now to FIG. 22, formation of the left atrial anteromedial lesion 246 will be described in detail. This lesion 246 is relatively short extending only about 5-7 mm from the anteromedial portion of the left atrial appendage LAA to the pulmonary vein isolation lesion 52 proximate a central portion between the left superior and inferior pulmonary vein orifices 231, 236. Due to the position of this lesion and the flexible nature of the appendage tissue, any one of a number of probes already mentioned, such as the probes illustrated in FIG. 32, the right angle probe (FIG. 24) or the pulmonary vein to mitral valve probe (FIG. 34), can be employed for this task. Typically, the probe device 247 of FIG. 34 is employed which includes an elongated shaft 66 having a first elbow portion 166 positioned between a relatively straight first portion 175 and a generally straight second portion 176. The first elbow portion has an arc length of about 45.degree. to about 65.degree. and a radius of curvature of about 3.2 cm to about 5.7 cm. Further, a second elbow portion 177 is positioned between the second portion 176 and the ablating end 70, angling the ablating end back toward the longitudinal axis of the first portion 175 of the elongated shaft 66. The ablating end 70 preferably includes the second elbow portion 177, having an arc length of about 80.degree. to about 100.degree., and a radius of curvature of about 6.0 mm to about 1.9 mm. This translates to an ablating surface of about 2.0 cm to about 6.0 cm in length.

One of the above-mentioned probes will be introduced through the second retractor 68 where the distal end of the probe will be inserted through the same fifth penetration 161 central to the fifth purse-string suture 63. Once the selected probe 247, as shown in FIG. 22, is properly aligned, the ablating surface 65 is urged into contact with the atrial endocardial surface of the left atrial appendage LAA for localized ablation. Subsequently, the left atrial anteromedial lesion 246 will be formed.

Since the left atrial wall at the anteromedial portion thereof is exceedingly thin, this transmural ablation could be performed from outside the heart H. Hence, upon contact of the ablating surface of a selected probe (not shown) with the atrial epicardial surface of the left atrial appendage LAA, localized, transmural cryothermia may be applied externally/epicardially to form this left atrial anteromedial lesion 246.

The last lesion to be performed through the fifth penetration 161 is the posterior vertical left atrial lesion 248, also known as the coronary sinus lesion (FIG. 23), extending from the pulmonary vein isolation lesion 52 to the annulus 250 of the mitral valve MV. This lesion may be critical since improper ablation may enable atrial conduction to continue in either direction beneath the pulmonary veins. This may result in a long macro-reentrant circuit that propagates around the posterior-inferior left atrium, the atrial septum, the anterior-superior left atrium, the lateral wall of the left atrium beneath the excised left atrial appendage, and back to the posterior inferior left atrium.

Therefore, it is imperative that the coronary sinus be ablated circumferentially and transmurally in the exact plane of the atriotomy or lesion. Proper transmural and circumferential ablation near the coronary sinus effectively eliminates the need for dividing all atrial myocardial fibers traversing the fat pad of the underlying atrioventricular groove.

In the preferred embodiment, a modified probe 251 (FIG. 35) is employed to ablate this critical coronary sinus lesion 248. This probe 251 includes an elongated shaft 66 having a first elbow portion 166 positioned between a generally straight first portion 175 and a generally straight second portion 176. The first elbow portion has an arc length of about 30.degree. to about 50.degree. and a radius of curvature of about 1.2 cm to about 3.0 cm. Mounted at the distal end of the second portion 176 is the ablating end which is substantially similar in shape to the ablating end of the probe of FIG. 32. The ablating end 70 curves back toward the longitudinal axis of the first portion 175 of the elongated shaft 66.

Again, this interior region of the heart H is accessed through the fifth penetration 161, via the second access device 223. The distal end of the probe 251, is positioned through the penetration in the same manner as previous ablations. The unique curvature of this probe 251 enables manipulation of the ablating surface 65 from outside the thoracic cavity into proper alignment. FIG. 23 best illustrates that ablating surface 65 is moved into contact with the endocardial surface of the left atrial wall atrium for localized ablation extending from the pulmonary vein isolation lesion 52 to the mitral valve annulus 250. Particular care, as mentioned above, is taken to assure that this lesion extends through the coronary sinus for circumferential electrical isolation thereof. After contact for the designated period of 2-4 minutes, the ablating surface 65 of the probe is properly defrosting and the probe 251 is retracted rearwardly from the fifth penetration 161 for removal from the retractor. Subsequently, the fifth penetration 161 is further cinched to prevent blood lose through the fifth purse-string suture 63.

Due to the criticality of the circumferential ablation of the coronary sinus during formation of the pulmonary vein to mitral valve annulus lesion 248, an epicardial ablation may be performed on a portion of the outside heart wall opposite the endocardial ablation of the coronary sinus. Thus, the placement of this additional lesion (not shown) must be in the same plane as the coronary sinus lesion 248 (i.e., to the mitral valve annulus lesion) to assure circumferential ablation of the coronary sinus. This is performed by introducing a standard probe through the retractor 68, and strategically contacting the epicardial surface at the desired location opposite the coronary sinus lesion.

Upon completion of the above-mentioned series of elongated lesions, the left atrial appendage LAA is excised along the direction of broken line 252 in FIG. 23, similar to that of the prior procedures. This excision is considered more imperative than the excision of the right atrial appendage RAA since the threat of thromboembolism or clotting would more likely be fatal, induce strokes or cause other permanent damage. In the preferred form, this excision is performed in the same manner as the excision of the right atrial appendage (i.e., through suturing or stapling. After hemostatic closure is attained, the left atrial appendage LAA is excised using thoracoscopic scissors or an incision device. This left appendagectomy will extend completely around the base of the left atrial appendage along the solid line 252 in FIG. 3 or the broken line 253 in FIG. 23, which corresponds to the left atrial appendage excision in prior procedures.

Alternatively, the probes may be formed and dimensioned for contact with the epicardial surface 168 of the heart H. In these instances, no purse-string suture may be necessary for elongated transmural ablation. As an example, as best viewed in FIG. 36, a right-angle clamp type probe 255 is provided having an outer clamping portion 256 coupled to and formed to cooperate with a right angle probe or inner clamping portion 257 for transmural ablation of the heart wall through contact with epicardial surface 168 of the heart H. In this embodiment, an outer jaw portion 258 of outer clamping portion 256 is relatively thin (about 0.5 mm to about 2.0 mm in diameter) and preferably needle shaped to facilitate piercing of the heart wall at puncture 260. At the end of the needle-shaped outer clamping portion 256 is a pointed end 261 which enables piercing of the heart wall without requiring an initial incision and subsequent purse-string suture to prevent blood loss through the puncture 260.

Similar to clamping probe 198, when properly positioned, the outer and inner jaw portions 258, 262 of inner clamping portion 257 are moved inwardly in the direction of arrows 216, 216' (the outer jaw portion 258 contacting endocardial surface 228, and the inner jaw portion 262 contacting epicardial surface 168) to clamp the heart wall therebetween. FIG. 36 illustrates that inner jaw portion 262 includes ablation end 70 having ablation surface 65 which contacts epicardial surface 168 for ablation. Upon withdrawal of the needle-shaped outer jaw portion 258 from the heart wall, the puncture 260 may be closed through a single suture (not shown).

In these embodiments, an alignment device 263 is provided which cooperates between the outer and inner clamping portions 256, 257 for operating alignment between the outer jaw portion 258 and the inner jaw portion 262. This alignment device may be provided by any conventional alignment mechanism such as those alignment devices employed in the clamping probe 198.

To ensure transmural ablation, the needle-shaped outer jaw portion 258 may incorporate a temperature sensor 265 (FIG. 36) embedded in or positioned on the outer jaw portion to measure the temperature of the endocardial surface. Measurement of the proper surface temperature will better ensure transmural ablation. These temperature sensors may be provided by a variety of conventional temperature sensors.

Referring to FIGS. 37-40, another probe 280 is shown. A cryogen delivery tube 282 is positioned within an outer tube 284. A tip 286 seals an end of the outer tube 284. The delivery tube 282 is coupled to the source of cryogen (not shown) for delivering the cryogen to a boiler chamber 288. The cryogen is exhausted from the boiler chamber 288 through the annular area between the delivery tube 282 and outer tube 284. The delivery tube 282 has an end cap 290 which receives first and second tubes 292, 294 for delivery of cryogen to the boiler chamber 288 from the delivery tube 282. The first tube 292 has an exhaust port 296 which extends further into the boiler chamber 288 than an exhaust port 298 of the second tube 294 so that the cryogen is distributed throughout the boiler chamber 288. Although FIG. 38 depicts only the first and second outlet tubes 292, 294, any number of tubes may be provided.

Ablating surface 300 of the outer tube 284 is preferably made of a highly thermally conductive material such as copper. Referring to the end view of FIG. 40, the ablating surface 300 preferably has a ribbed inner surface 302 for enhanced thermal conduction between the boiler chamber 288 and the ablating surface 300. The probe 280 may take any of the configurations described herein.

Referring to FIGS. 41 and 42, another probe 306 is shown which has a device for adjusting the delivery rate of cryogen. The delivery tube 308 includes an inner tube 310 and an outer tube 312. The inner and outer tubes 310, 312 have holes 314, 316 therein through which the cryogen is delivered to boiler chamber 318. The outer tube 312 is slidable relative to the inner tube 310 and can be locked relative to the inner tube 310 at a number of discrete positions where the holes 314 in the inner tube 310 are aligned with the holes 316 in the outer tube 312. The holes 314 in the inner tube 310 are larger than holes 316 in the outer tube 312 so that when the outer tube 312 is in the position of FIG. 41 a larger amount of cryogen is delivered than when the outer tube 312 is in the position of FIG. 42. Thus, the amount of cryogen delivered, and therefore the rate of ablation and temperature of the probe 306, can be changed by moving the outer tube 312 relative to the inner tube 310. The delivery tube 308 may be used in the manner described above with any of the probe configurations described herein.

Referring to FIGS. 43 and 44, still another probe 318 is shown which includes suction ports 320 for ensuring intimate contact between the ablating surface 322 and the tissue. The suction ports 320 are coupled to a longitudinal channel 324 which is coupled to a vacuum source for applying suction. A cryogen delivery tube 326 delivers cryogen to boiler chamber 328 in the manner described herein.

Referring to FIGS. 45-47, a probe 330 having a malleable shaft 332 is shown. A malleable metal rod 334 is coextruded with a polymer 336 to form the shaft 332. A tip 338 having a boiler chamber 340 is attached to the shaft 332. The rod 334 permits the user to shape the shaft 332 as necessary so that the tip 338 can reach the tissue to be ablated. The tip 338 has fittings 342 which are received in a cryogen exhaust path 344 and a cryogen delivery path 346 in the shaft 332. The rod 334 is preferably made of stainless steel and the polymer 336 is preferably polyurethane. The tip 338 may be made of a suitable thermally conductive material such as copper. Cryogen is delivered through ports 348 in a delivery tube 350 and is expanded in the boiler chamber 340. The cryogen is then withdrawn through the exhaust path 344.

Finally, as set forth in the parent application incorporated herein by reference, access devices may be placed in the heart walls to enable the passage of the probes through the wells of the access devices.

While the present invention has been primarily directed toward ablation from the endocardial surfaces of the atria, it will be understood that many lesions or portions of the lesions may be created through ablation of the endocardial surfaces of the atria employing the present probes. While the specific embodiments of the invention described herein will refer to a closed-chest surgical procedure and system for the treatment of medically refractory atrial fibrillation, it is understood that the invention will be useful in ablation of other tissue structures, including surgical treatment of Wolfe-Parkinson-White (WPW) Syndrome, ventricular fibrillation, congestive heart failure and other procedures in which interventional devices are introduced into the interior of the heart, coronary arteries, or great vessels. The present invention facilitates the performance of such procedures through percutaneous penetrations within intercostal spaces, eliminating the need for a median stemotomy or other form of gross thoracotomy. However, as will be apparent although not preferred, the system and procedure of the present invention could be performed in an open-chest surgical procedure as well.

What is claimed is:

1. A device for ablating tissue, the device comprising:
a clamping device having an end and a clamping jaw at said end; and
a malleable shaft coupled to the clamping device and having an ablating end,
wherein the clamping jaw and the ablating end are movable between a released position, wherein the clamping jaw is separated from the ablating end, and a clamped position, wherein the clamping jaw is urged against the ablating end; and
wherein the clamping device may be locked into place relative to the malleable shaft in the clamped position.

2. The device according to claim 1, wherein the ablating end comprises an ablating element selected from the group consisting of cryogenic ablating elements, RF ablating elements, ultrasound ablating elements, microwave ablating elements, laser ablating elements, chemical ablating elements, biological ablating elements, and resistive heating ablating elements.

3. The device according to claim 1, wherein the clamping jaw and the ablating end are substantially similarly shaped and dimensioned.

4. The device according to claim 1, further comprising a handle configured to manipulate the clamping jaw and the ablating element between the released and clamped positions.

5. The device according to claim 1, wherein the shaft and clamping device are pivotally coupled.

6. The device according to claim 1, wherein the shaft and clamping device are releasably coupled.

7. A device for ablating tissue, the device comprising:
an outer jaw portion located at an end of a clamping shaft;
an inner jaw portion located at an end of an attachment shaft; and
an ablating end on at least one of the inner and outer jaw portions,
wherein the clamping shaft and the attachment shaft are coupled to each other such that the inner and outer jaw portions are movable relative to each other between a clamped condition and an unclamped condition, wherein the clamping shaft may be locked into place relative to the attachment shaft in the clamped condition, and
wherein at least one of the clamping shaft and the attachment shaft is malleable.

8. The device according to claim 7, wherein the clamping shaft and the attachment shaft are slidably coupled.

9. The device according to claim 7, wherein the clamping shaft and the attachment shaft are releasably coupled.

10. The device according to claim 7, wherein the clamping shaft and the attachment shaft are rotatably coupled.

11. The device according to claim 7, further comprising an alignment device adapted to align the inner and outer jaw portions about cardiac tissue.

12. The device according to claim 7, further comprising a second ablating end on the other of the inner and outer jaw portions.

13. The device according to claim 7, wherein the inner and outer jaw portions extend substantially orthogonally from the attachment shaft and the clamping shaft, respectively.

14. The device according to claim 7, wherein the inner and outer jaw portions define between them a tissue gap when in the clamped condition.

15. The device according to claim 7, wherein the at least one ablating end comprises at least one ablating element selected from the group consisting of cryogenic ablating elements, RF ablating elements, ultrasound ablating elements, microwave ablating elements, laser ablating elements, chemical ablating elements, biological ablating elements, and resistive heating ablating elements.

16. The device according to claim 7, wherein the inner and outer jaw portions are formed and dimensioned to cooperatively clamp cardiac tissue therebetween.

17. A method of treating cardiac arrhythmia, the method comprising the steps of:
providing a tissue ablating device, the device comprising:
a clamping shaft having an end;
an outer jaw portion located at the end of the clamping shaft;
a malleable attachment shaft having an end;
an inner jaw portion located at the end of the attachment shaft; and
an ablating end on at least one of the inner and outer jaw portions,
wherein the clamping shaft and the attachment shaft are coupled to each other such that the inner and outer jaw portions are movable relative to each other between a clamped condition and an unclamped condition, and
wherein the clamping shaft may be locked into place relative to the malleable attachment shaft in the clamped condition;
introducing the tissue ablating device into a body cavity of a patient;
clamping tissue to be ablated between the inner and outer jaw portions; and
applying ablating energy to the tissue via the ablating end.

18. The method according to claim 17, wherein the step of applying ablating energy to the tissue via the ablating end comprises applying ablating energy selected from the group consisting of RF energy, microwave energy, heat energy, cryogenic energy, laser energy, and ultrasound energy.

19. A device for ablating tissue, comprising:
at least one malleable shaft having a distal end;
a first jaw and a second jaw, at least one of the first jaw and the second jaw being located at the distal end of the at least one malleable shaft, wherein the first jaw and the second jaw are movable relative to each other between a released position and a clamped position, wherein the first jaw may be locked into place relative to the second jaw in the clamped condition; and
at least one ablating surface on at least one of the first jaw and the second jaw.

20. The device according to claim 19, wherein the at least one malleable shaft comprises a first malleable shaft and a second malleable shaft, the first jaw being located at a distal end of the first malleable shaft and the second jaw being located at a distal end of the second malleable shaft.

21. The device according to claim 20, wherein the first malleable shaft is movably coupled to the second malleable shaft.

22. A device for ablating tissue, comprising:
a first member adapted to contact a first tissue surface;
a second member adapted to contact a second tissue surface; and
at least one ablating surface on at least one of the first member and the second member, the ablating surface adapted to deliver ablating energy to the tissue,
wherein at least one of the first member and the second member comprises at least one malleable segment, and
wherein the first member and the second member are movable relative to each other between a released position, wherein the first member is separated from the second member, and a clamped position, wherein the first member is urged against the second member, and wherein the first member may be locked into place relative to the second member in the clamped position.

23. The device according to claim 22, wherein each of the first member and the second member comprises at least one malleable segment.

24. The device according to claim 22, wherein the at least one ablating surface is attached to the at least one malleable segment.

25. The device according to claim 22, wherein the first member is movably coupled to the second member.

26. The device according to claim 25, wherein the first member is slidably coupled to the second member.

27. The device according to claim 25, wherein the first member is pivotably coupled to the second member.

28. A method of treating cardiac arrhythmia, comprising the steps of:
providing an ablation device having a first member, a second member movable relative to the first member, and at least one ablating surface on at least one of the first member and the second member, at least one of the first member and the second member including at least one malleable segment,
wherein the first member may be locked into place relative to the second member;
shaping the at least one malleable segment;
introducing the ablation device into the patient's body;
bringing one of the first member and the second member into contact with a first surface of a cardiac tissue to be ablated and the other of the first member and the second member into contact with a second surface of a cardiac tissue to be ablated, the first member and the second member thereby being in opposing relation across the cardiac tissue to be ablated, and the at least one ablating surface being positioned to form a lesion in the cardiac tissue; and
ablating the cardiac tissue to form the lesion in the cardiac tissue.

29. The method according to claim 28, wherein the step of shaping the at least one malleable segment comprises shaping the at least one malleable segment such that, when the first member and the second member are brought into contact with the cardiac tissue to be ablated, the at least one ablating surface is positioned at a preselected lesion location.

30. The method according to claim 28, wherein the at least one ablating surface is attached to the at least one malleable segment, and wherein the step of shaping the at least one malleable segment comprises shaping the at least one malleable segment into a preselected lesion configuration.

31. The method according to claim 28, wherein the step of bringing one of the first member and the second member into contact with a first surface of a cardiac tissue to be ablated and the other of the first member and the second member into contact with a second surface of a cardiac tissue to be ablated comprises:
bringing the one of the first member and the second member into contact with an epicardial surface of the cardiac tissue to be ablated; and
bringing the other of the first member and the second member into contact with an endocardial surface of the cardiac tissue to be ablated.

* * * * *